United States Patent
Hu et al.

(10) Patent No.: US 7,575,881 B2
(45) Date of Patent: Aug. 18, 2009

(54) MODULATION OF NITRIC OXIDE SIGNALING THROUGH SIGNALING THROUGH SPECIFIC REGULATION BY ARGINYLATION AND THE N-END RULE PATHWAY

(75) Inventors: Rong-Gui Hu, Pasadena, CA (US); Jun Sheng, Pasadena, CA (US); Yong Tae Kwon, Wexford, PA (US); Anna Kashina, Newtown Square, PA (US); Alexander Varshavsky, La Canada, CA (US)

(73) Assignee: California Institute of Technology, Pasadena, CA (US)

( * ) Notice: Subject to any disclaimer, the term of this patent is extended or adjusted under 35 U.S.C. 154(b) by 222 days.

(21) Appl. No.: 11/228,157

(22) Filed: Sep. 16, 2005

(65) Prior Publication Data
US 2006/0084097 A1    Apr. 20, 2006

Related U.S. Application Data

(63) Continuation-in-part of application No. 10/394,765, filed on Mar. 21, 2003, now abandoned, and a continuation-in-part of application No. 10/395,048, filed on Mar. 21, 2003, now abandoned.

(60) Provisional application No. 60/366,218, filed on Mar. 21, 2002, provisional application No. 60/366,207, filed on Mar. 21, 2002.

(51) Int. Cl.
*G01N 33/53*     (2006.01)
*G01N 33/573*    (2006.01)
*C12Q 1/48*      (2006.01)

(52) U.S. Cl. .............. 435/7.21; 435/7.71; 435/7.72; 435/7.92; 435/7.93; 435/7.95; 435/8; 435/69.7; 435/69.8; 435/252.2; 435/252.8; 435/254.11; 530/329; 530/350

(58) Field of Classification Search .............. None
See application file for complete search history.

(56) References Cited

U.S. PATENT DOCUMENTS 6,979,551 B2 * 12/2005 Issakani et al. ............ 435/7.92
7,262,005 B1   8/2007 Stack et al.

FOREIGN PATENT DOCUMENTS

WO    98/23283    6/1998
WO    99/13077    3/1999

OTHER PUBLICATIONS

Stryer et al, in Biochemistry, Third edition, W H Freeman Company, New York, pp. 31-33, 1998.*
Kwon et al, Science 297: 96-99, 2002.*
Davydov et al, J Biol Chem 275(30): 22931-22941, 2000.*
Baker et al, Proc Nat Acad Sci USA 88: 1090-1094, 1991.*
Gonda et al., "Universality and Structure of the N-end Rule", *The Journal of Biological Chemistry*, 264(28):16700-16712 (1989).

* cited by examiner

*Primary Examiner*—Phuong Huynh
(74) *Attorney, Agent, or Firm*—DLA Piper LLP (US)

(57) ABSTRACT

Screening assays that allow for the identification of agents that modulate the activity of the arginylation branch of the N-end rule pathway are provided. Also provided are method of using an agent that modulate the activity of the arginylation branch of the N-end rule pathway to increase or decrease protein degradation in a cell, and to modulate physiologic and pathologic associated with N-end rule pathway mediated arginylation.

36 Claims, 8 Drawing Sheets

```
                        SEQUENCE LISTING

<160> NUMBER OF SEQ ID NOS: 11

<210> SEQ ID NO 1
<211> LENGTH: 7
<212> TYPE: PRT
<213> ORGANISM: Artificial sequence
<220> FEATURE:
<223> OTHER INFORMATION: Synthetic construct

<400> SEQUENCE: 1

Cys His Ser Gly Ala Trp Leu
1               5

<210> SEQ ID NO 2
<211> LENGTH: 8
<212> TYPE: PRT
<213> ORGANISM: Artificial sequence
<220> FEATURE:
<223> OTHER INFORMATION: Synthetic construct

<400> SEQUENCE: 2

Cys His Gly Ser Gly Ala Trp Leu
1               5

<210> SEQ ID NO 3
<211> LENGTH: 7
<212> TYPE: PRT
<213> ORGANISM: Artificial sequence
<220> FEATURE:
<223> OTHER INFORMATION: Synthetic construct

<400> SEQUENCE: 3

His Gly Ser Gly Ala Trp Leu
1               5

<210> SEQ ID NO 4
<211> LENGTH: 21
<212> TYPE: DNA
<213> ORGANISM: Artificial sequence
<220> FEATURE:
<223> OTHER INFORMATION: Primer

<400> SEQUENCE: 4
aatggagacc ccccagagaa t                                          21

<210> SEQ ID NO 5
<211> LENGTH: 20
<212> TYPE: DNA
<213> ORGANISM: Artificial sequence
```

```
<220> FEATURE:
<223> OTHER INFORMATION: Primer

<400> SEQUENCE: 5
tccaggagag tgtccactgc                                                  20

<210> SEQ ID NO 6
<211> LENGTH: 20
<212> TYPE: DNA
<213> ORGANISM: Artificial sequence
<220> FEATURE:
<223> OTHER INFORMATION: Primer

<400> SEQUENCE: 6
acgcttgggt cttgttcact                                                  20

<210> SEQ ID NO 7
<211> LENGTH: 20
<212> TYPE: DNA
<213> ORGANISM: Artificial sequence
<220> FEATURE:
<223> OTHER INFORMATION: Primer

<400> SEQUENCE: 7
gtctctgggt cctctggtca                                                  20

<210> SEQ ID NO 8
<211> LENGTH: 20
<212> TYPE: DNA
<213> ORGANISM: Artificial sequence
<220> FEATURE:
<223> OTHER INFORMATION: Primer

<400> SEQUENCE: 8
aagacaaggc agcggtggaa                                                  20

<210> SEQ ID NO 9
<211> LENGTH: 20
<212> TYPE: DNA
<213> ORGANISM: Artificial sequence
<220> FEATURE:
<223> OTHER INFORMATION: Primer

<400> SEQUENCE: 9
gcaggggaca ggaaatagtt                                                  20

<210> SEQ ID NO 10
<211> LENGTH: 21
<212> TYPE: DNA
<213> ORGANISM: Artificial sequence
<220> FEATURE:
<223> OTHER INFORMATION: Primer

<400> SEQUENCE: 10
catcaccatc ttccaggagc g                                                21

<210> SEQ ID NO 11
<211> LENGTH: 21
<212> TYPE: DNA
<213> ORGANISM: Artificial sequence
<220> FEATURE:
<223> OTHER INFORMATION: Primer

<400> SEQUENCE: 11
gaggggccat ccacagtctt c                                                21
```

US 7,575,881 B2

MODULATION OF NITRIC OXIDE SIGNALING THROUGH SIGNALING THROUGH SPECIFIC REGULATION BY ARGINYLATION AND THE N-END RULE PATHWAY

CROSS REFERENCE TO RELATED APPLICATIONS

This application is a Continuation-in-Part of U.S. Ser. No. 10/394,765, filed Mar. 21, 2003, now abandoned and of U.S. Ser. No. 10/395,048, filed Mar. 21, 2003, now abandoned each of which claims the benefit of priority under 35 U.S.C. § 119(e) of U.S. Ser. No. 60/366,207, filed Mar. 21, 2002, and of U.S. Ser. No. 60/366,218, filed Mar. 21, 2002, the entire content of each of which is incorporated herein by reference.

GRANT INFORMATION

This invention was made with government support under Grant No. GM 31530 awarded by the National Institutes of Health. The United States government has certain rights in this invention.

BACKGROUND OF THE INVENTION

1. Field of the Invention

The invention relates generally to intracellular metabolism and catabolism, and more specifically to a nitric oxide (NO) sensor comprising the N-terminal cysteine amino acid residue sequence motif of a polypeptide, which is subject to oxidation by NO, to methods of identifying agents that modulate the activity of the arginylation branch of the N-end rule pathway, to methods of modulating protein degradation in a cell via the arginylation branch of the N-end rule pathway, and to methods of ameliorating physiological and/or pathological conditions associated with N-end rule pathway-mediated arginylation.

2. Background Information

The N-end rule relates the in vivo half-life of a protein to the identity of its N-terminal residue (1-4; citations can be found following the Examples). The corresponding ubiquitin (Ub)-dependent proteolytic pathway, called the N-end rule pathway, recognizes a set of degradation signals (degrons) that includes the signals called N-degrons. An N-degron includes a destabilizing N-terminal residue of a protein and an internal Lys residue, which is the site of formation of a protein-linked poly-Ub chain. The N-end rule has a hierarchic structure. N-terminal Asn and Gln are tertiary destabilizing residues that function through their deamidation, by N-terminal amidohydrolases, to yield the secondary destabilizing residues Asp and Glu. The activity of N-terminal Asp and Glu requires their conjugation, by ATE1-encoded isoforms of Arg-tRNA-protein transferase (R-transferase), to Arg, a primary destabilizing residues (11, 12). N-terminal arginylated Glu and Asp are recognized by the E3 Ub ligases of the N-end rule pathway. A polyubiquitinylated substrate is processively degraded by the 26S proteasome. The known functions of the N-end rule pathway include the control of peptide import (through conditional degradation of the import repressor), the maintenance of chromosome stability (through degradation of a conditionally produced cohesin fragment), and the regulation of apoptosis (through degradation of a caspase-processed inhibitor of apoptosis), as well as regulation of meiosis, cardiovascular development, and leaf senescence in plants.

Nitric oxide (NO) is produced in eukaryotes primarily by NO synthases. This compound and its derivatives play a role, as either stressors or regulators, in a vast range of functions, including cardiovascular homeostasis, immunity, neurotransmission, ion conductance, glycolysis, apoptosis, and many other processes. Biological effects of NO are mediated by its covalent modifications of proteins, either of their prosthetic groups or amino acid residues, particularly Cys and Tyr. The reactivity of these residues toward NO is modulated by sequence contexts of these residues in a protein. NO converts Cys residues into S-nitrosothiols, a process that can involve oxygen ($O_2$) or its derivatives. S-nitrosylation modulates protein functions either directly or after additional (often oxygen-dependent) chemical transformations that yield oxidized Cys derivatives such as Cys-sulphinic acid ($CysO_2H$) or Cys-sulphonic acid ($CysO_3H$).

In mammals, the set of N-end rule's destabilizing residues that function through arginylation includes Asp, Glu, and Cys, the latter of which is a stabilizing (unarginylated) residue in the yeast Saccharomyces cerevisiae. An N-degron is produced from pre-N-degron through a proteolytic cleavage. Methionine aminopeptidases (MetAPs), which remove Met from the N-termini of newly formed proteins, act if, and only if, the residue at position 2, to be made N-terminal after cleavage, has a small enough side chain (2, and refs. therein). Consequently, among the 13 destabilizing residues of the mammalian N-end rule, only Cys can be exposed at the N-terminus of a nascent protein through the cleavage by MetAPs. Note that any destabilizing residue, including Cys, can be made N-terminal through internal cleavages of proteins by other intracellular proteases such as separases, caspases, and calpains. Previous work showed that Cys at position 2 of the in vivo-arginylated RGS4 protein was $CysO_3H$, rather than Cys, suggesting that oxidation of N-terminal Cys may precede arginylation, and may be required for it. However, the factors involved in the oxidation of cysteine by NO have not been described.

SUMMARY OF THE INVENTION

The present invention is based, in part, on the discovery that nitric oxide (NO) is directly involved in the oxidation of N-terminal cysteine residue of a polypeptide, thus rendering the N-terminal cysteine residue a substrate for arginylation by arginine-tRNA protein transferase (R-transferase), followed by the N-end rule pathway-mediated degradation of a polypeptide substrate. Whereas some specific internal cysteine residues, in certain specific proteins, have previously been found to be modified by NO, the discovery that N-terminal cysteine in a polypeptide is the target for modification by NO is unprecedented, and is one of the seminal discoveries underlying the present invention. The present invention is further based, in part, on the discovery that the arginylation branch of the N-end rule pathway is involved in various physiological and pathological conditions, including, for example, conditions as diverse as angiogenesis and other aspects of cardiovascular health in mammals, and in leaf senescence and susceptibility of plants to infection by pathogens. Accordingly, the present invention, through the discovery that the N-terminal cysteine of a polypeptide is a key, NO-dependent, arginylation-dependent determinant of the in vivo stability of proteins that possess N-terminal cysteine, and through independent evidence for a multiple physiological role of the arginylation of N-terminal cysteine, provides a new approach to ameliorating disease through targeting either or both the NO-dependent and NO-independent N-dependent arginylation, and provides screening assays for identifying agents that modulate N-end rule pathway-mediated arginylation of a polypeptide, agents identified by such methods, and methods of modulating protein degradation by the arginylation branch of the N-end rule pathway, and further provides methods of ameliorating physiological and/or pathological conditions associated with N-end rule pathway mediated arginylation.

In one embodiment, the present invention relates to a method of identifying an agent that modulates N-end rule pathway-mediated arginylation of N-terminal cysteine (Cys) residues of a polypeptide. Such a method can be performed, for example, by contacting at least one (e.g., 1, 2, 3, 4, 5, or more) sample that includes a peptide having an N-terminal Cys-(basic amino acid residue) motif (e.g., N-Cys-Arg or N-Cys-Lys, or N-Cys-His) with at least one test agent, under conditions suitable for the N-terminal Cys of the peptide to act as a substrate for an N-end rule pathway reaction; and detecting a change in the N-end rule pathway substrate activity of the N-terminal Cys of the polypeptide in the presence of the test agent as compared to the absence of the test agent, wherein a change in the substrate activity identifies the test agent as an agent that modulates N-end rule pathway mediated arginylation of an N-terminal Cys residue of a peptide.

The previously known, multiple methods for regulating cellular and organismal physiology by altering the levels of NO (e.g., by inhibitors of NO synthases, or by scavengers of NO, or by chemical donors of NO) in an organism can now be complemented by the entirely different, previously unknown approach that makes possible to achieve at least some of the same beneficial medical effects not by altering the levels of NO, as the current approaches do, but by altering, instead, the levels of arginylation of NO-modified N-terminal cysteine in a polypeptide, the latter aim achieved by devising specific inhibitors or activators of R-transferase that arginylates the said N-terminal cysteine after its NO-dependent oxidation, which must occur for the arginylation to take place. Since only some of many different functions of NO involve modification of N-terminal cysteine in polypeptides (NO's other functions involve modifications of polypeptides' prosthetic groups, internal cysteines, and tyrosines, etc.), an inhibitor of R-transferase would interfere with a small subset of NO functions, the one specific to N-terminal cysteine. This subset has already been demonstrated to be of physiological relevance. Thus, the present invention, through the uncovering of NO-dependent oxidation of N-terminal cysteine, provides an alternative, new and more selective route to medically beneficial effects that are currently achieved through drugs that alter the levels of NO. Not all of NO functions would be impacted by altering the activity of R-transferase, but those (arginylation-mediated) functions of NO that would be impacted, may be modulated with greater physiological selectivity, and therefore fewer side effects.

The polypeptide containing the N-terminal Cys ("target polypeptide" or "target polypeptide") used in a method of the invention can be synthetic, or can be a naturally occurring protein. Further, the N-terminal Cys examined according to the present methods can constitute an internal residue of a polypeptide, wherein, upon cleavage (e.g., by a protease or chemical reagent), a proteolytic or other fragment is generated that comprises a polypeptide having an N-terminal Cys residue suitable for N-end rule pathway mediated arginylation. As such, where the target polypeptide having the N-terminal Cys comprises an internal peptide portion of a larger polypeptide, a method of the invention can include contacting the polypeptide with a protease or other reagent that cleaves the polypeptide to generate the peptide having the N-terminal Cys-(basic amino acid residue) motif suitable for arginylation.

By way of example, the target polypeptide used in the present methods can be a protein such as a regulator of G protein signaling (RGS) protein (e.g., RGS4 or RGS16). The target polypeptide also can be a synthetic peptide (e.g., a peptide having the amino acid sequence Cys-His-Ser-Gly-Ala-Trp-Leu; SEQ ID NO: 1), which can be used as an isolated polypeptide or can be a part of a fusion protein that comprises a second (or more) polypeptide(s). Where the peptide comprises a fusion protein, the peptide can be at the N-terminal portion of the fusion protein, or can be internal in the fusion protein, which can be cleaved such that the peptide, particularly the Cys residue, is at the N-terminus of a cleavage product (fragment) of the fusion protein. In a fusion protein comprising a target polypeptide having an N-terminal Cys residue, the second (or other) polypeptide component of the fusion protein, which can, but need not be positioned C-terminal to the target polypeptide component, can be, for example, a reporter polypeptide such as a selectable marker protein (e.g., an antibiotic resistance protein) or a detectable label (e.g., a fluorescent protein such as *Aequorea* green fluorescent protein, a luminescence generating protein such as luciferase, or other enzyme such as β-galactosidase). Further, the peptide having the N-terminal Cys residue, or a fusion protein comprising the peptide, can be contained in a cell (e.g., a test cell from which a sample is obtained), and can be expressed from a recombinant nucleic acid molecule introduced into the cell, including a recombinant nucleic acid molecule in which expression of the peptide (or fusion protein) is inducible.

A test agent examined according to the present methods can be any type of molecule, including a peptide or a polynucleotide, which contains naturally and/or non-naturally occurring subunits and/or bonds (e.g., D-amino acids or nucleotide analogs), a small organic molecule, a peptidomimetic, and the like. Further, as disclosed herein, the screening assays of the invention can be performed in a high throughput format using, for example, a plurality of samples, which can be the same or different and, independently, can be contacted with one or more test agents, which can be the same or different, including, for example, duplicate, triplicate, etc. samples, and/or control samples. As such, test agents can comprise two or more test agents of a library of test agents, for example, a combinatorial library of test agents, which can be a random library of test agent, a biased library of test agents, a variegated library of test agents, or a combination thereof.

An agent identified according to the present methods can modulate (e.g., can increase, or can reduce or inhibit) N-end rule pathway mediated arginylation in any of a variety of ways. For example, an agent identified by the present methods can alter (e.g., reduce or inhibit) NO mediated oxidation of the N-terminal Cys of the target polypeptide, for example, by reducing or inhibiting S-nitrosylation levels of the N-terminal Cys of the peptide or by reducing or inhibiting oxidation of an S-nitrosylated N-terminal Cys of the peptide. Alternatively, or in addition, the agent can alter arginylation of an oxidized N-terminal Cys of the peptide by an R-transferase (e.g., a mammalian R-transferase such as ATE-1). Further, an agent of the invention may alter the activity or level of R-transferase (e.g., ATE1) e.g., in cells and tissues.

In some cases, an R-transferase also can arginylate an N-terminal aspartic acid (Asp) residue of a peptide and/or an N-terminal glutamic acid (Glu) residue of a peptide. Where an R-transferase can arginylate an N-terminal Asp and/or Glu, the present methods can further identify an agent that alters only arginylation of an N-terminal Cys residue by the R-transferase, or an agent that alters arginylation of an N-terminal Cys of a peptide as well as an N-terminal Asp and/or Glu of another peptide(s). For example, an agent that modulates N-end rule mediated arginylation of an N-terminal Cys, but not an N-terminal Asp and/or Glu, of a peptide can be identified by contacting an agent that has been identified according to the present methods as having the ability to modulate N-end rule pathway mediated arginylation of an N-terminal Cys of a first target polypeptide with a second peptide comprising an N-terminal Asp residue and/or a second (or third) peptide comprising an N-terminal Glu residue, under conditions suitable for N-end rule mediated arginylation of the N-terminal Asp and/or Glu residue(s), and detecting no change in the N-terminal Asp and/or Glu in the presence of the agent as compared to the absence of the agent. Further, the method similarly can be performed using peptides having an N-terminal asparagine (Asn) and/or glutamine (Gln) residue, which can be converted by deamidation to Asp and/or Glu, respectively, and, therefore, act as a substrate for N-end rule pathway mediated arginylation.

A sample examined according to the screening assays of the invention can be a cell-free sample (e.g., a sample prepared using purified components), or can be a cell or a sample comprising a cell extract, wherein the sample includes components necessary and sufficient for examining N-end rule pathway mediated arginylation, or a step of the pathway (e.g., NO induced oxidation of an N-terminal Cys residue of a peptide, or deamidation of N-terminal Asn and/or Gln residues of a peptide to Asp and/or Glu, respectively). A cell sample can be prepared using any type of cell that exhibits, or can be modified to exhibit, the step or steps of the N-end rule pathway being examined. For example, the cell can be a plant cell or an animal cell (e.g., a mammalian cell such as a human cell) that naturally expresses an endogenous R-transferase or that is genetically modified to express an R-transferase from an exogenously introduced polynucleotide. Further, where a cell sample is used, the cell can be a normal cell (i.e., from an organism that is not exhibiting any signs or symptoms of any or a particular disease) or can be cell from an organism suffering from an abnormal or undesirable physiological and/or pathological condition such as a disease, a trauma, or the like. For example, a plant cell examined according to the present methods can be from a plant that is infected with a pathogen, wherein a test agent is examined in an effort to identify an agent that modulates N-end rule mediated arginylation so as to reduce the pathogenicity of the infecting agent or limit the pathogenic effect. Similarly, wherein an animal cell is obtained from an organism having a disorder associated with abnormal (e.g., increased) protein degradation due to N-end rule mediated arginylation, the test agent can be examined in an effort to identify an agent that modulates N-end rule mediated arginylation in the cell such that protein degradation is decreased to a more normal level characteristic of the same type of cell in an otherwise healthy animal. For example, the protein that is subject to abnormal degradation by the arginylation branch of the N-end rule pathway can be a caspase, wherein an agent that increases or decreases degradation of the caspase, or a proteolytic cleavage product of the caspase, can be used to decrease or increase, respectively, the caspase degradation to a level more normally characteristic of the particular cell type.

The ability of a test agent to modulate N-end rule mediated arginylation can be identified in any of various ways, including, for example, by detecting a change in NO mediated oxidation or arginylation of the N-terminal Cys of the peptide or by detecting a change in R-transferase activity. As such, a change in the N-end rule pathway substrate activity of the N-terminal Cys of the peptide can be detected, for example, by measuring S-nitrosylation levels of the N-terminal Cys of the peptide, or by measuring oxidation of the N-terminal Cys of the peptide, or by measuring arginylation of the N-terminal Cys. Such changes can be measured using any method convenient for detecting such changes, including, for example, mass spectroscopy or capillary electrophoresis. Accordingly, an agent that modulates N-end rule pathway mediated arginylation is provided, wherein the agent is identified by a screening assay of the invention.

The present invention also relates to a method of identifying an agent that modulates N-end rule pathway N-terminal arginylation activity. Such a method can be performed, for example, by contacting at least one test agent with at least a first cell that expresses a reporter protein comprising an N-terminal Asp, Glu, or Cys residue, wherein the half-life of the reporter protein is affected by arginylation of the N-terminal residue of the protein; and measuring the level of the reporter protein expressed in the presence as compared to the absence of the test agent, wherein a change in the level of reporter protein expressed is indicative of modulation of N-terminal arginylation activity, thereby identifying an agent that modulates N-terminal arginylation activity by the N-end rule pathway. The cell can be any type of cell that exhibits N-end rule pathway mediated arginylation, including, for example, a cultured mammalian cell, a yeast cell, or a bacterial cell. In one aspect, the reporter protein in the cell is expressed as a cleavable fusion protein, which comprises a reporter protein and a ubiquitin domain functionally linked to the reporter protein. In another aspect, the reporter protein is a selectable marker protein, a fluorescent protein, a luminescence generating protein, or an enzyme, and, optionally, can be inducibly expressed in the cell. The reporter protein generally has a half-life in the cell of less than about an hour in the absence of the test agent (e.g., less than about ten minutes in the absence of the test agent).

The method of identifying an agent that modulates N-terminal arginylation activity by the N-end rule pathway method can further include contacting at least a second cell that expresses a second reporter protein, wherein the half-life of the second reporter protein is affected by N-terminal arginylation of the protein, with at least one potential modulator of an R-transferase (e.g., ATE1) gene product activity; and measuring the level of second reporter protein expressed within the second cell relative to the level of reporter protein expressed within the first cell. In one aspect of this method, the first cell and the second cell are the same cell. An agent identified by the present methods can have any of various activities associated with the arginylation branch of the N-end rule pathway, including, for example, modulating cleavage and/or degradation of proteins involved in apoptosis (e.g., caspases), modulating angiogenesis, or modulating susceptibility of a plant to infection by a pathogen.

In another embodiment, the present invention relates to a method of modulating degradation of a protein by the N-end rule arginylation pathway in a cell. Such a method can be performed, for example, by contacting the cell (target cell) with an agent that that modulates N-end rule pathway mediated arginylation of an N-terminal Cys residue of a protein, or of a proteolytic cleavage product of a protein, wherein the agent alters arginine-tRNA protein transferase (R-transferase) activity in the cell, S-nitrosylation of the N-terminal Cys of the protein (or cleavage product) by NO, or oxidation of an S-nitrosylated N-terminal Cys of the protein (or cleavage product), thereby modulating degradation of the protein by the N-end rule arginylation pathway in the cell. In one aspect, the agent increases the R-transferase activity, S-nitrosylation of the N-terminal Cys, or oxidation of the S-nitrosylated N-terminal Cys. In another aspect, the agent reduces or inhibits the R-transferase activity, S-nitrosylation of the N-terminal Cys, or oxidation of the S-nitrosylated N-terminal Cys.

According to the present methods, the cell to be contacted can be a cell in culture, including, for example, a cell of a cell culture or cell line that has been adapted to growth in culture or a cell that is obtained from a living subject and placed into a culture or other suitable medium and contacted with the agent ex vivo. The cell to be contacted also can be a cell of a living subject, wherein contacting the cell with the agent is performed in vivo by administering the agent to the subject, for example, systemically, or locally to the site of the cell(s) to be contacted. The cell to be contacted, and in which protein degradation by the N-end rule pathway can be modulated, can be any type of cell having an N-end rule pathway arginylation branch. For example, the cell can be a cell of a plant that is infected with a pathogen, wherein it is desired to modulate protein degradation due to N-end rule mediated arginylation to reduce or inhibit the pathogenic effect of the pathogen. A plant cell can be contacted with agent useful for the present methods in any of various ways, including, for example, by watering the plant with a solution containing the agent, or by spraying the agent onto the plant.

A cell to be contacted with an agent for purposes of the present methods also can be an animal cell, including, for example, a mammalian cell such as a human cell. In various aspects, the cell can be a neuronal cell (e.g., a neuron, astrocyte, or glial cell), a smooth muscle cell (e.g., an endothelial smooth muscle cell), or a cardiac muscle cell. In one aspect, an animal cell is contacted with an agent that modulates protein degradation by the arginylation branch of the N-end rule pathway in order to ameliorate a condition in which such protein degradation contributes to undesirable signs and/or symptoms characteristic of the condition. The condition can be an undesirable physiological condition (e.g., erectile dysfunction or impotence), a pathological condition (e.g., cancer), or a condition associated with a wound, wherein the method is practiced to facilitate wound healing. In another aspect, the target cells are contacted by administering the agent to a subject, whereby the agent contacts the cell(s).

The present invention also relates to a method of modulating arginylation of a peptide by the N-end rule pathway in an organism. Such a method can be performed, for example, by administering to the organism an agent that that modulates N-end rule pathway mediated arginylation of an N-terminal Cys, Asp, and/or Glu residue of a peptide, whereby the agent alters N-end rule pathway activity in cells of the organism, thereby modulating arginylation of a peptide by the N-end rule pathway in the organism. The organism can be a plant or an animal, either of which endogenously expresses proteins of the N-end rule pathway arginylation branch (e.g., R-transferase), or expresses one or more heterologous proteins from an exogenously introduced recombinant nucleic acid molecule(s) encoding the protein(s), which can be expressed transiently (e.g., inducibly), constitutively, or at a particular developmental stage of the organism. In one aspect, the present method provides a means to decrease degradation of a protein, or proteolytic fragment thereof, having an N-terminal Cys in an organism by administering to the organism an agent that reduces or inhibits R-transferase levels or activity, S-nitrosylation of the N-terminal Cys of the peptide by NO, and/or oxidation of an S-nitrosylated N-terminal Cys of the peptide.

An agent useful for practicing the present methods can be any type of molecule, including, for example, a polypeptide, a polynucleotide, or a small organic molecule. For example, the agent can be a polynucleotide encoding an R-transferase, wherein administration of the agent comprises introducing the polynucleotide into a cell of the subject, whereby the R transferase is expressed. Such an agent increases R-transferase levels and activity in the cell and, therefore, increases arginylation of peptides having an N-terminal Cys residue. The agent can also comprise a small interfering RNA (siRNA) molecule specific for a polynucleotide encoding an R-transferase, wherein administration of the agent comprises introducing the siRNA molecule, or a polynucleotide encoding the siRNA, into a cell of the subject, whereby the siRNA reduces or inhibits expression of the polynucleotide encoding the R-transferase. Such an agent decreases R-transferase levels and activity in the cell and, therefore, decreases arginylation of peptides having an N-terminal Cys residue. An agent also can be a peptide (or peptidomimetic) that, for example, has the general structure of an N-end rule pathway substrate (e.g., a peptide having an N-terminal Cys-(basic amino acid) motif, and further includes a reactive group such that the peptide, upon interacting with a component of the pathway (e.g., an R-transferase) forms an irreversible bond with the component, thereby preventing the component from further interactions.

As disclosed herein, the arginylation branch of the N-end rule pathway is involved in various physiological and pathological conditions and, therefore, can be modulated in order to alter such conditions as desired. Accordingly, the invention provides a method of modulating angiogenesis in a subject. Such a method can be performed, for example, by administering to the subject an agent that modulates N-end rule pathway mediated arginylation of an N-terminal Cys, Asp, and/or Glu residue of a peptide, thereby modulating angiogenesis in the subject. The subject to be treated according to the present method can be a mammal, including, for example, a human, a dog, a cat, a sheep, a deer, or other wild, domestic and/or farm animal. The method can be used to increase angiogenesis, for example, to facilitate wound healing, or to ameliorate signs or symptoms associated with coronary artery disease or stroke, or can be used to reduce or inhibit angiogenesis, for example, to reduce the growth of a tumor (e.g., a malignant tumor).

The invention also provides a method of ameliorating a disorder associated with protein degradation due to N-end rule arginylation pathway activity in a subject. Such a method can be performed, for example, by administering to the subject an agent that modulates N-end rule pathway mediated arginylation of an N-terminal Cys, Asp, and/or Glu residue of a peptide, whereby protein degradation is altered, thereby ameliorating the disorder in the subject. The disorder can be any disorder in which protein degradation due to N-end rule pathway arginylation contributes to the etiology and/or signs or symptoms of the disorder, including, for example, comprises a nervous system disorder such as schizophrenia, a muscular disorder, angina, or impotence. In one aspect, the disorder is associated with apoptosis, wherein the method provides a means to modulate the proteolytic cascade characteristic of apoptosis (e.g., by inhibiting activation of or degradation of caspases).

In still another embodiment, the present invention relates to a method of modulating the severity of infection or susceptibility of a plant to infection by a pathogen. Such a method can be performed, for example, by the plant with an agent that modulates N-end rule pathway mediated arginylation of an N-terminal Cys, Asp, and/or Glu residue of a peptide, whereby the agent alters protein degradation in cells of the plant, thereby modulating susceptibility of the plant to infection by the pathogen. The pathogen is a bacterial pathogen or a viral pathogen, and generally is a pathogen produces a virulence factor, which induces a hypersensitivity response in the plant, wherein the agent reduces or inhibit the activity of the arginylation branch of the N-end rule pathway, for example, by reducing or inhibiting R-transferase activity, in the plant.

The present invention demonstrate that oxidation of N-terminal Cys is essential for its arginylation. Most importantly, we discovered that the in vivo oxidation of a protein's N-terminal Cys, prior to its arginylation, requires NO. This accounts for N-terminal Cys being a destabilizing residue in mammalian cells, which produce NO, but stabilizing in yeast, which lack NO synthases. We reconstituted the NO-dependent arginylation of N-terminal Cys in an in vitro system as well. This process prefers a basic residue at position 2 of a substrate but it is not an absolute requirement. The levels of regulatory proteins with this N-terminal motif (Cys-[basic residue]), such as RGS4, RGS5 and RGS16, are greatly increased in mouse ATE1$^{-/-}$ embryos that lack arginylation. RGS4, RGS5 and RGS16 are the first physiological substrates of mammalian N-end rule pathway. Given the involvement of these proteins in cardiovascular homeostasis and tubulogenesis, their stabilization may underlie the previously observed abnormal angiogenesis and heart defects in ATE1$^{-/-}$ embryos. A mammalian genome encodes approximately 30 proteins, including RGS4, RGS5 and RGS16, that contain the Met-Cys-[basic residue] N-terminal motif, which acts as a MetAP-cleaved, NO-dependent, arginylation-mediated, Cys-containing pre-N-degron. Together, our results identify the arginylation branch of the N-end rule pathway as a new sensor of NO in mammalian cells that functions through its ability to destroy specific regulatory proteins bearing N-terminal Cys, at the rates controlled by NO, and apparently by oxygen as well.

BRIEF DESCRIPTION OF THE DRAWINGS

FIG. 1*a*, The mammalian N-end rule pathway. N-terminal residues are indicated by single-letter abbreviations for amino acids. Yellow ovals denote the rest of a protein substrate. MetAPs, methionine aminopeptidases. The "cysteine" (Cys) sector, in the upper left corner, describes the main discovery of this work: the nitric oxide (NO)-mediated oxidation of N-terminal Cys, with subsequent arginylation of oxidized Cys by ATE1-encoded isoforms of Arg-tRNA-protein transferase (R-transferase). C* denotes oxidized Cys, either Cys-sulphinic acid (CysO$_2$(H)) or Cys-sulphonic acid (CysO$_3$(H)). Type 1 and type 2 primary destabilizing N-terminal residues are recognized by E3 Ub ligases of the N-end rule pathway, including UBR1 and UBR2. Through their other substrate-binding sites, these E3s also recognize internal (non-N-terminal) degrons in other substrates of the N-end rule pathway, denoted by a larger yellow oval. FIG. 1*b*, MetAPs remove Met from the N-terminus of a polypeptide if the residue at position 2 belongs to the set of residues shown. FIGS. 1*c-j*, N-terminal Cys must be oxidized prior to its arginylation. Three 8-residue peptides are denoted as X-p. Their N-terminal residues (X) were either Asp, Cys, or CysO$_3$H. X-p was incubated with mouse ATE1-1 R-transferase at pH 7.5 in the presence of ATP, *S. cerevisiae* Arg-tRNA synthetase and tRNAs, followed by analyses of peptide products, either by capillary electrophoresis (CE) (c-h) or by MALDI-TOF mass spectrometry (MS) (i, j). The x/y axes in CE patterns correspond, respectively, to the time of elution from CE column and OD$_{200}$. c, d, arginylation assay with Asp-p, for 0 min (c) and 60 min (d), followed by CE. e, f, same but with CysO$_3$H-p. g, h, same-but with Cys-p. Vertical arrows in e and f indicate electrophoretic position of the (separately run) marker Arg-Cys-p, a chemically synthesized arginylated Cys-p. i, MALDI-TOF of the sample in d. j, MALDI-TOF of the sample in f. The molecular masses in i and j are of ionized [+H$^+$] derivatives of the molecules indicated on these panels in their unionized form.

FIG. 2*a*, lanes 1 and 2, equal amounts of total protein in extracts from wild-type (+/+) and ATE1$^{-/-}$ E12.5 embryos were fractionated by 12% SDS-PAGE, followed by immunoblotting with anti-RGS4 antibody. FIG. 2*b*, same as in a but With extracts from indicated tissues of +/+and ATE1$^{-/-}$ E14.5 embryos. FIG. 2*c*, same as in a but with anti-RGS5 antibody and E14.5 embryos. FIG. 2*d*, same as in b but with anti-RGS5 antibody. FIG. 2*e*, same as in a but with anti-RGS16 antibody. FIG. 2*f*, same as in b but with anti-RGS16 antibody. FIG. 2*g*, 3T3$^{to\!f\!f}$RGS4$_{f\!h}$ cells expressing RGS4$_{f\!h}$ were grown in the presence of either ambient air (lane 1) or low (0.5%) oxygen (lane 2). Equal amounts of total protein in extracts were subjected to immunoblotting with antibody to RGS4. FIG. 2*h*, lanes 1-3, equal amounts of total protein in extracts from +/+ (lane 1), [UBR1$^{-/-}$UBR2$^{-/-}$] (lane 2), and UBR1/2$^{dnR2}$ (lane 3) cell lines were subjected to immunoblotting with antibody to RGS16. Lanes 4-6, same as, respectively, lanes 1-3, but immunoblotting with antibody to serine racemase. Lanes 7, 8, same as lanes 4-6, but with extracts from +/+ (lane 7) and ATE1$^{-/-}$ E12.5 embryos (lane 8). The bands of 23K RGS4 (apparent M$_r$≈28K), 20K RGS5 (apparent M$_r$≈21K), 23K RGS16 (apparent M$_r$≈25K), and 37K serine racemase are indicated.

FIG. 3 shows immunoassays identifying decreasing nitric oxide in vivo stabilizes RGS4 and RGS16. FIG. 3*a*, 3T3$^{to\!f\!f}$RGS4$_{f\!h}$ cells, expressing RGS4$_{f\!h}$, were either untreated or treated with compounds that decrease the levels of intracellular NO, followed by immunoblotting with antibody to RGS4. Lane 1, 3T3$^{to\!f\!f}$RGS4$_{f\!h}$ cells in the presence of doxycycline. Lane 2, same but in the absence of doxycycline. Lane 3, same as lane 2, except that cells were treated with CPTIO. Lane 4, same as lane 3, but treatment with LMMA. Lanes 5 and 6, same as lanes 2 and 3, respectively, but with parental $_3$T$_3$$^{to\!f\!f}$ cells lacking the RGS4$_{f\!h}$-expressing cassette. Lanes 7 and 8, same as lanes 2 and 3, respectively, but independent experiment, with independently grown 3T3$^{to\!f\!f}$RGS4$_{f\!h}$ cells. Lane 9, same as lane 2 but independent experiment. Lane 10, same as lane 9, but treatment with 0.5 mM N3411. Lane 11, same as lane 10 but treatment with 1 mM N3411. Also indicated is the band of 37K glyceraldehyde-3-phosphate dehydrogenase (GAPDH), a loading control, detected on the same membrane with antibody to GAPDH. In experiments of lanes 1-4 and 9-11, anti-RGS4 antibody detected two bands: the upper ban's position was the one expected for RGS4$_{f\!h}$, while the lower band was apparently a proteolytic fragment of RGS4$_{f\!h}$, since changes in its levels paralleled those of full-length RGS4$_{f\!h}$. The lower band was not observed in an otherwise identical but independent experiment (lanes 7, 8). In addition, the same anti-RGS4 antibody did not detect RGS4 in parental $_3$T$_3$$^{to\!f\!f}$ cells (lanes 5, 6), and detected one RGS4 band in ATE1$^{-/-}$ embryos (FIG. 2*a*). FIG. 3*b*, Determination, through Edman degradation, of N-terminal sequence of RGS4$_{f\!h}$ isolated from 3T3$^{to\!f\!f}$RGS4$_{f\!h}$ cells that had been treated as described in the diagram and main text. $C^{alk}$, alkylated Cys residue. The asterisk after N-terminal, posttranslationally conjugated Arg (R) residue indicates a "sequenceable" but unidentified residue, at the position of oxidized Cys residue in RGS4, in contrast to alkylated (identifiable) Cys ($C^{alk}$) at position 12. FIG. 3c, lanes 1 and 2, immunoblotting, with antibody to RGS16, of extracts from NIH-3T3 cells that were either untreated (lane 1) or treated with CPTIO (lane 2). Lanes 3 and 4, same as lanes 1 and 2 but with ATE1$^{-/-}$ EF cells[12] lacking arginylation. FIG. 3d, lane 1, $^{14}$C-labeled protein markers, of 66K, 45K, and 30K. Lanes 2-4, RGS4$_{fh}$-expressing 3T3$^{tofh}$RGS4$_{fh}$ cells were labeled for 10 min with $^{35}$S-methionine/cysteine and chased for 1 and 2 h, followed by immunoprecipitation of extracts with antibody to RGS4, SDS-PAGE, and autoradiography. Lanes 5-7, same as lanes 2-4, but with CPTIO-treated 3T3$^{tofh}$RGS4$_{fh}$ cells. Lanes 8 and 9, same as lanes 2 and 5, respectively, but with 3T3$^{tofh}$ (RGS4$_{fh}$-lacking) cells.

FIG. 5a, arginylation assay with Asp-p for 60 min, followed by CE. FIG. 5b, same but with CysO$_3$H-p. FIG. 5c, same but with Cys-p. Vertical arrow in c indicates electrophoretic position of the (separately run) marker Arg-Cys-p, a chemically synthesized arginylated derivative of Cys-p.

FIG. 6a, RGS4-specific Northern hybridization with RNA from +/+ and ATE-1$^{-/-}$ E12.5 embryos. The band of ~2.8 kb RGS4 mRNA is indicated (lanes 1, 2). Lanes 3 and 4, the corresponding ethidium-stained total RNA patterns (loading controls, shown at a different magnification). FIG. 6b, same as in a but RGS16-specific Northern hybridization. The band of ~2.4 kb RGS16 mRNA is indicated. FIG. 6c, lanes 1 and 2, equal amounts of total protein in extracts from +/+ and ATE-1$^{-/-}$ E14.5 embryos were immunoblotted with antibody to mouse R-transferase. Lanes 3, 5, 7, 9, same as lane 1 but with specific tissues of +/+ E14.5 embryos. Lanes 4, 6, 8, 10, same as lane 2 but with specific tissues of ATE1$^{-/-}$ embryos. The band of 59K ATE1 is indicated.

FIG. 7a, Lane 1, molecular size markers. Lanes 2-4, an amplified fragment, derived from NOS1 (nNOS) mRNA in mouse 3T3$^{tofh}$RGS4$_{fh}$ cells, $_3$T$_3$$^{tofh}$ cells, and NIH-3T3 cells, respectively. FIG. 7b, same but an amplified control fragment, of GAPDH mRNA. 3T3$^{tofh}$RGS4$_{fh}$ cells produced detectable but much lower levels of NOS2 (iNOS) mRNA, whereas NOS3 (eNOS) mRNA was undetectable by RT-PCR.

DETAILED DESCRIPTION OF THE INVENTION

Figure 1:
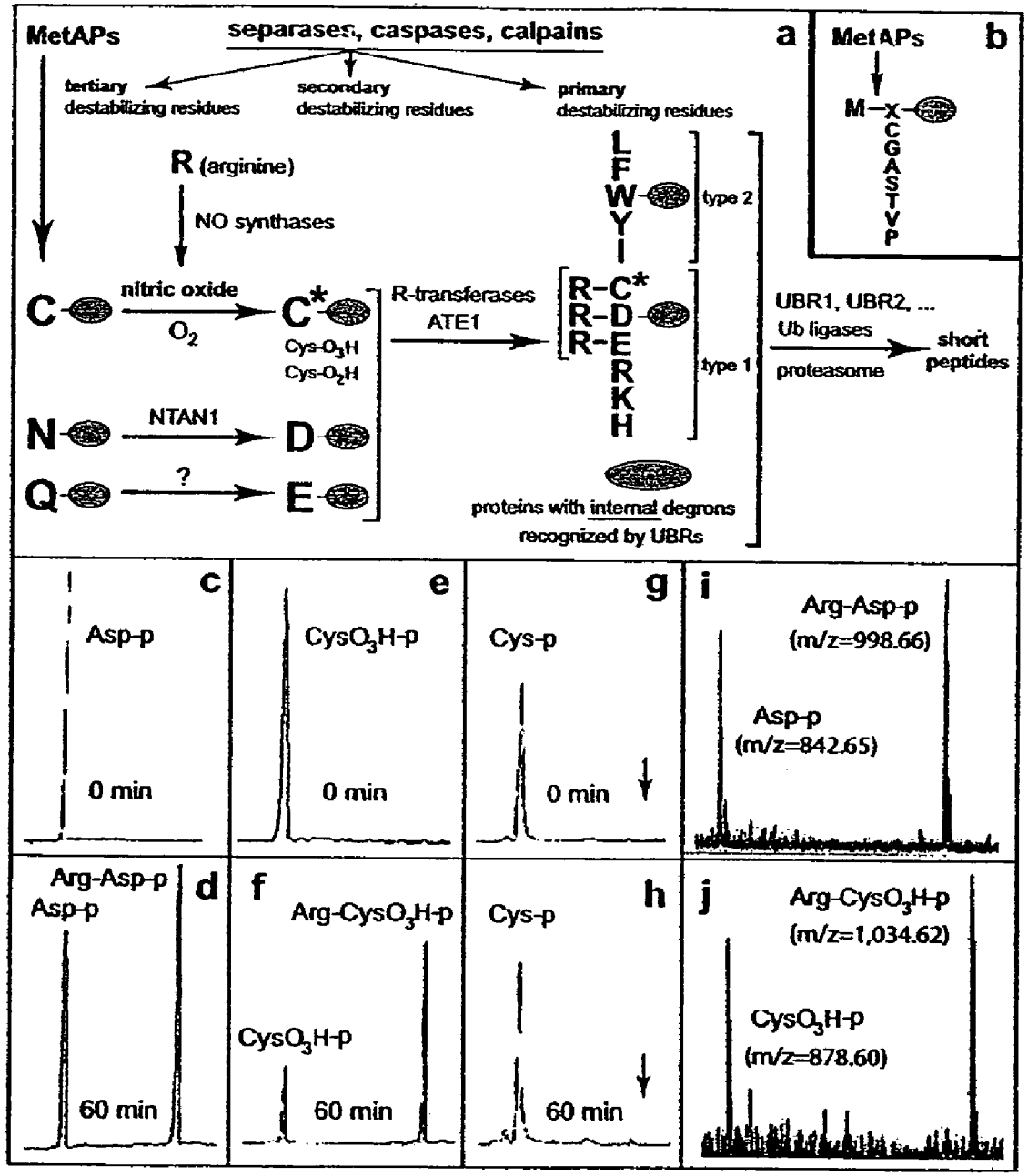
FIG. 1 is an illustration showing that N-terminal cysteine must be oxidized prior to its arginylation.

The conjugation of arginine to the N-termini of proteins is a part of the N-end rule pathway of protein degradation. Three N-terminal residues, aspartate (Asp), glutamate (Glu), and cysteine (Cys), are arginylated by arginine-tRNA-protein transferases (R-transferases). As disclosed herein, oxidation of N-terminal Cys is essential for its subsequent arginylation. Further, the in vivo oxidation of N-terminal Cys requires nitric oxide (NO), thus accounting for N-terminal Cys being a destabilizing residue in mammalian cells, which produce NO, but a stabilizing residue in yeast, which lack NO synthases. The levels of regulatory proteins bearing N-terminal Cys (e.g., RGS4 and RGS16) are greatly increased in mouse ATE1$^{-/-}$ embryos, which lack arginylation activity, and provide a link to abnormal angiogenesis and heart development in ATE1$^{-/-}$ embryos. The present results identify the arginylation branch of the N-end rule pathway as a NO sensor that functions through its ability to destroy specific regulatory proteins bearing N-terminal Cys, at the rates controlled by NO, and as a modulator of various physiological and pathological conditions.

As disclosed herein, oxidation of the N-terminal Cys residue in a polypeptide is required for the arginylation of Cys by ATE1-encoded Arg-tRNA-protein transferases (R-transferases) (see Example 1). Further, the arginylation branch of the N-end rule pathway (see FIG. 1) acts as a sensor of NO that destroys specific regulatory proteins bearing N-terminal Cys, at the rates controlled by NO. Previously, it was believed that regulation by NO was based on changes in the functional (e.g., enzymatic) activity of NO-modified proteins. In contrast, a Cys-based N-degron in a regulatory protein, as disclosed herein, enables the coupling of NO levels to the activity of regulator-containing signaling circuits such as those modulated by RGS4 and RGS16 (see Example 1) through NO-dependent degradation of this regulator by the N-end rule pathway. Such control by NO likely involves a number of other cytosolic and nuclear proteins that bear N-terminal Cys in a cognate downstream sequence context. In this respect, the Cys-(basic residue) motif preferred for NO-mediated oxidation of N-terminal Cys is present in RGS4, RGS5, and RGS16, as well as about 30 other proteins encoded by the mouse genome. Further, other cytosolic and nuclear proteins (or proteins translocated back to cytosol from the endoplasmic reticulum) can become substrates of the NO-dependent, Cys-specific branch of the N-end rule pathway if, for example, they are cleaved by proteases to yield C-terminal fragments bearing N-terminal Cys (see, e.g., Ref. 3; citations follow Examples).

The N-end rule substrates such as RGS4 and RGS16, which are targeted for degradation through NO-mediated oxidation of their N-terminal Cys residues, can also be modified, at the same position, by palmitoylation of the thiol side chain of Cys (39, 40). These two modifications are expected to be mutually exclusive, and can act in opposite ways. For example, palmitoylation increases the in vivo activity of RGS4 and RGS16 as down-regulators of their cognate G proteins (39, 40), whereas proteolytic destruction of RGS4 and RGS16 by the N-end rule pathway reduces their activity by decreasing their levels in a cell. RGS4 is targeted to membranes by its N-terminus-proximal amphipathic helix, then is palmitoylated at its N-terminal Cys. This initial palmitoylation stabilizes RGS4-membrane interactions, and also leads to palmitoylation of RGS4 at two other Cys residues (39, 40). Since palmitoylation takes place at membranes, the oxidation-dependent arginylation of RGS4, RGS16 and other N-terminal Cys-bearing N-end rule substrates can occur at the stage of newly formed proteins on their way to membranes, or with proteins that are stochastically and transiently membrane-free as a result of their enzymatic depalmitoylation. However, since NO has affinity for lipid bilayers, oxidation of N-terminal Cys also can take place at membranes. Since there are several splicing-derived isoforms of mouse R-transferase (11), some isoforms can have affinity for either membranes or membrane-associated proteins such that arginylation of oxidized N-terminal Cys can occur near membranes.

Mouse ATE1$^{-/-}$ embryos, which lack R-transferases, die before E17 with a variety of defects, primarily in angiogenic remodeling and heart development, including ventricular septal defects, hypoplasia of myocardium, and truncus arteriosis (failure to separate the aorta from pulmonary artery; see Ref. 12). Up-regulation of RGS4 expression is a molecular correlate of human heart failure (32). The present findings that the levels of RGS4 and RGS16 are greatly increased in the hearts and other organs of ATE1$^{-/-}$ embryos, and that NO is required for the proteolytic down-regulation of these RGS proteins (Example 1) can account, at least in part, for the role of NO in suppressing pathological changes in the heart (41). The functions of NO in cardiovascular homeostasis include stimulation of cGMP formation by guanylyl cyclase (41). In addition, NO regulates cardiac contractility, through S-nitrosylation of the calcium release channel (26) and through reaction with superoxide produced by xanthine oxidoreductase (42). The present results reveal another role of NO signaling in the heart and other organs—the control of regulatory proteins bearing N-terminal Cys through their NO-dependent, arginylation-mediated degradation by the N-end rule pathway. As such, pharmacological manipulation of the activities or expression of R-transferase isoforms can provide an alternative and more selective route to medically beneficial effects that are currently achieved by drugs that alter the levels of NO.

NO is a neural modulator that acts through spatiotemporally controlled modifications of proteins that contain transition-metal centers or Cys residues in cognate conformational or sequence contexts (22). Many functions of the brain are also regulated by the Ub system (43), and the Ub-dependent N-end rule pathway, including its arginylation branch, is active in neurons (44). The disclosed finding that NO mediates the targeting of proteins having an N-terminal Cys motif provides a means to manipulate specific functions of the N-end rule pathway in the nervous system. RGS4 and RGS16, which were determined to be in vivo N-end rule substrates whose proteolytic targeting requires both NO and arginylation (Example 1), are expressed in the brain. RGS4 has been implicated in the etiology of schizophrenia based on the identification of several RGS4-linked single-nucleotide polymorphisms outside the exons of RGS4 tend to segregate with this disease. In addition, RGS4 mRNA was under-expressed in the prefrontal cortex of schizophrenia patients (see Ref. 45).

The mammalian ATE1-encoded R-transferases are strong sequelogs (34) of the ATE1 R-transferase in the yeast (fungus) S. cerevisiae. However, while the inactivation of mouse ATE1 results in embryonic lethality (12), a deletion of S. cerevisiae ATE1 rendered yeast cells unable to degrade reporter substrates with N-terminal Asp or Glu but did not appear to cause any other abnormal phenotype (2, 33). The absence of NO synthases from yeast accounts for N-terminal Cys being a stabilizing residue in the N-end rule of S. cerevisiae. The present results suggest that arginylation can function in fungi and other organisms as a sensor of nitrosative/oxidative stress. Animals and plants employ NO in their defense against infections, and prokaryotic and eukaryotic pathogens have several anti-NO systems (46, 47), including those that involve protein degradation (48, 49). As such, the NO-mediated oxidation of N-terminal Cys of a "sentinel" protein of an invading pathogen results in arginylation and degradation of the protein by the N-end rule pathway, thereby initiating a protective response in the organism. Further, molecular oxygen ($O_2$) and its more reactive derivatives participate in the NO-dependent oxidation of proteins in vivo (23, 25, 26). As such, the N-end rule pathway, by virtue of its ability to degrade specific proteins through NO-mediated oxidation of their N-terminal Cys residues (FIG. 1), can function as an oxygen sensor as well, integrating the signaling by NO and $O_2$.

The present invention provides methods of identifying agents that modulate the arginylation branch of the N-end rule pathway. As used herein, the term "modulate" means change or alter. As such, an agent that modulates, for example, N-end rule pathway mediated arginylation of a protein can act, for example, to increase or to reduce or inhibit the activity of an R-transferase to arginylate an N-terminal Asp, Glu, or oxidized Cys residue of a protein. The terms "reduce" and "inhibit" are used together because it is recognized, for example, that an agent may reduce R-transferase activity below a level that is detectable by a particular assay being used and, therefore, that it may not be possible to determine from the assay whether the activity is completely inhibited. Nevertheless, the ability of an agent to reduce or inhibit the activity of the arginylation branch of the N-end rule pathway, including at any level of the pathway (e.g., oxidation of an N-terminal Cys; arginylation of an N-terminal Asp, Glu, or oxidized Cys; deamidation of an N-terminal Asn or Gln; or ubiquitinylation of the target polypeptide), will be readily apparent upon comparison of the particular activity in the presence and absence of the agent (or test agent).

The methods of the invention provide screening assays useful for determining whether a test agent can modulate the arginylation branch of the N-end rule pathway and, therefore, the rate or amount of protein degradation that occurs in a sample (e.g., a cell). As used herein, the term "test agent" means any compound that is being examined for the ability to modulate N-end rule pathway mediated arginylation. A test agent (and an agent that modulates arginylation) can be any type of molecule, including, for example a peptide, a polynucleotide, an antibody, a glycoprotein, a carbohydrate, a small organic molecule, or a peptidomimetic.

The term "polynucleotide" is used broadly herein to mean a sequence of two or more deoxyribonucleotides or ribonucleotides that are linked together by a phosphodiester bond. As such, the term "polynucleotide" includes RNA and DNA, which can be an isolated naturally occurring polynucleotide or portion thereof or a synthetic polynucleotide; can be single stranded or double stranded, as well as a DNA/RNA hybrid; and can encode one or more peptide(s) or can have (or encode a second polynucleotide) having an activity (e.g., an antisense molecule, a ribozyme, a small interfering RNA (siRNA), and the like). A polynucleotide agent (or test agent) can contain nucleoside or nucleotide analogs, or a backbone bond other than a phosphodiester bond. In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide also can contain nucleotide analogs, including non-naturally occurring synthetic nucleotides or modified naturally occurring nucleotides. Such nucleotide analogs are well known in the art and commercially available, as are polynucleotides containing such nucleotide analogs (Lin et al., *Nucl. Acids Res.* 22:5220-5234, 1994; Jellinek et al., *Biochemistry* 34:11363-11372, 1995; Pagratis et al., *Nature Biotechnol.* 15:68-73, 1997, each of which is incorporated herein by reference).

The covalent bond linking the nucleotides of a polynucleotide generally is a phosphodiester bond. However, the covalent bond also can be any of numerous other bonds, including a thiodiester bond, a phosphorothioate bond, a peptide-like bond or any other bond known to those in the art as useful for linking nucleotides to produce synthetic polynucleotides (see, for example, Tam et al., *Nucl. Acids Res.* 22:977-986, 1994; Ecker and Crooke, *BioTechnology* 13:351360, 1995, each of which is incorporated herein by reference). The incorporation of non-naturally occurring nucleotide analogs or bonds linking the nucleotides or analogs can be particularly useful where the polynucleotide is to be exposed to an environment that can contain a nucleolytic activity, including, for example, a tissue culture medium or upon administration to a living subject, since the modified polynucleotides can be less susceptible to degradation.

A polynucleotide agent (test agent) comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs into a polynucleotide and, therefore, can be used to produce such a polynucleotide recombinantly from an appropriate template (Jellinek et al., supra, 1995).

Peptides also can be useful as test agents. The term "peptide" is used broadly herein to refer to a molecule containing two or more amino acids or amino acid analogs (or modified forms thereof) linked by peptide bonds. As such, peptide test agents (or agents) can contain one or more D-amino acids and/or L-amino acids; and/or one or more amino acid analogs, for example, an amino acid that has been derivatized or otherwise modified at its reactive side chain. In addition, one or more peptide bonds in the peptide can be modified, and a reactive group at the amino terminus or the carboxy terminus or both can be modified. Peptides containing D-amino acids, or L-amino acid analogs, or the like, can have improved stability to a protease, an oxidizing agent or other reactive material the peptide may encounter in a biological environment. Further, the stability of a peptide agent (or test agent) can be improved by generating (or linking) a fusion protein comprising the peptide and a second polypeptide (e.g., an Fc domain of an antibody) that increases the half-life of the peptide agent in vivo. Peptides also can be modified to have decreased stability in a biological environment, if desired, such that the period of time the peptide is active in the environment is reduced. In this respect, it is recognized that certain screening assays of the invention can utilize a peptide having, for example, an N-terminal Cys residue (e.g., as an N-terminal Cys-(basic amino acid residue) motif). Such peptides can have any of the above-described characteristics (e.g., can contain one or more D-amino acid residues), provided the peptide maintains the ability to act as a substrate for a step of the N-end rule pathway being examined (e.g., as a substrate for NO mediated oxidation of Cys, R-transferase mediated arginylation, or ubiquitination).

Antibodies provide an example of peptides useful as test agents in a screening assay of the invention. As used herein, the term "antibody" is used in its broadest sense to include polyclonal and monoclonal antibodies, as well as antigen binding fragments of such antibodies. Antibodies are characterized, in part, in that they specifically bind to an antigen, particularly to one or more epitopes of an antigen. The term "binds specifically" or "specific binding activity" or the like, when used in reference to an antibody, means that an interaction of the antibody and a particular epitope has a dissociation constant of at least about $1\times10^{-6}$ M, generally at least about $1\times10^{-7}$ M, usually at least about $1\times10^{-8}$ M, and particularly at least about $1\times10^{-9}$ M or $1\times10^{-10}$ M or less. As such, Fab, $F(ab')_2$, Fd and Fv fragments of an antibody that retain specific binding activity are included within the definition of an antibody.

The term "antibody" as used herein includes naturally occurring antibodies as well as non-naturally occurring antibodies, including, for example, single chain antibodies, chimeric, bifunctional and humanized antibodies, as well as antigen-binding fragments thereof, such antibodies providing the advantage that they can be relatively small in size and, therefore, more conveniently made and/or used. Such non-naturally occurring antibodies can be constructed using solid phase peptide synthesis, can be produced recombinantly or can be obtained, for example, by screening combinatorial libraries consisting of variable heavy chains and variable light chains (see Huse et al., *Science* 246:1275-1281, 1989, which is incorporated herein by reference). These and other methods of making, for example, chimeric, humanized, CDR-grafted, single chain, and bifunctional antibodies are well known (Winter and Harris, *Immunol. Today* 14:243-246, 1993; Ward et al., *Nature* 341:544-546, 1989; Harlow and Lane, *Antibodies: A laboratory manual* (Cold Spring Harbor Laboratory Press, 1999); Hilyard et al., *Protein Engineering: A practical approach* (IRL Press 1992); Borrabeck, *Antibody Engineering*, 2d ed. (Oxford University Press 1995); each of which is incorporated herein by reference).

A screening assay of the invention can be practiced by contacting a sample that contains (or to which can be added) components that are necessary and sufficient for the one or more steps of the arginylation branch of the N-end rule pathway that is (are) being examined, including, for example, under conditions suitable for oxidation of an N-terminal Cys residue by NO and/or arginylation of an N-terminal Asp, Glu, and/or oxidized Cys residue by an R-transferase (e.g., a mammalian ATE-1). Such conditions are exemplified herein (see Example 1), and include, for example, appropriate buffer conditions (including pH), salt concentration (e.g., physiological), and other conditions, which can be selected based on whether the assay is performed in a cell free format or is performed in a cell based assay.

As disclosed herein, a screening assay of the invention can be performed in vitro (e.g., in a cell free system using purified or partially purified components) or in a cell (e.g., in a cell or tissue culture system). Where the method is performed in vitro, the components of the N-end rule pathway being examined (e.g., R-transferase) can be obtained, for example, from an extract of a cell expressing the R-transferase, or can be a synthetic R-transferase prepared, for example, using an in vitro translation or coupled transcription/translation reaction using a polynucleotide encoding the R-transferase (e.g., an ATE-1 gene sequence). Where the method is performed as a cell based assay, the sample can be a cell sample, wherein the component(s) of the arginylation branch of the N-end rule pathway is expressed in the cell. Further, the cell can be one in which the component(s) is expressed in nature in the cell (e.g., a muscle cell expressing an R-transferase), or can be a cell that has been genetically modified to express a polynucleotide encoding the component (e.g., a eukaryotic cell such as a yeast cell, a *Xenopus* oocyte, a mouse fibroblast, or the like).

In one aspect, the screening assays of the invention provide a means to identify an agent that modulates (e.g., reduces or inhibits) ATE1-mediated N-terminal arginylation. Such an assay can be performed using mammalian cells in culture or yeast (*S. cerevisiae*) cells in culture. In mammalian cells and yeast, the ATE1-encoded R-transferases are solely responsible for N-terminal arginylation. An advantage of a yeast-based screen is the ease of handling and analyzing yeast cell cultures. However, a disadvantage of yeast is that potential inhibitors of R-transferase that would be able cross the plasma membrane of mammalian cells may be incapable of gaining entry into yeast cells, given substantial differences in the permeability (and transport) properties of the plasma membrane between yeast and mammals. A mammalian cell-based screen avoids such a potential problem where the agent to be identified is be used in mammals. A mammalian (mouse or human) cell line can be used that is genetically modified to express a short-lived reporter whose ubiquitin-dependent degradation by the N-end rule pathway involves N-terminal arginylation. Such a reporter can be a protein, including, for example, a genetically selectable or a visually detectable reporter.

A number of classes of reporter proteins are suitable for use with the methods of the invention. For example, the reporter protein can be a genetically selectable marker protein, and the relative level of the reporter protein in the presence and absence of a test agent can accomplished indirectly through a selective genetic screen that requires the presence of said reporter protein for survival of the first cell. In such an example, an agent that modulates (e.g., inhibits) R-transferase activity, for example, would lengthen the half-life of the reporter protein. For example, the selectable marker protein can be an antibiotic resistance protein. In one such example, the reporter protein is designed to be short-lived in a cell, the cell will be relatively sensitive to the relevant antibiotic. By contrast, if the protein is made long-lived in vivo, for example through the inhibition of a proteolytic pathway (e.g., through inhibition of R-transferase activity) that normally destroys this protein, its steady-state level would increase, and the cell would become resistant to the same dose of antibiotic. This readout would enable a selection-based screen. A number of reporter proteins that confer antibiotic resistance are known to those skilled in the art.

Detection of the relative abundance of the reporter protein also can be accomplished by more direct means. For example, the reporter protein can be a screenable reporter protein. Such proteins include, but are not limited to, green fluorescent protein (GFP) and *E. coli* β-galactosidase (βgal), and, when expressed in a cell, can be detected either through their fluorescence (GFP) or their enzymatic activity (βgal). The suitable reporter protein can be expressed in the cell type used for the assay and has sufficient intensity or activity to be detected within the cell at the appropriate concentrations. Making a reporter of this class short-lived in vivo can strongly diminish its steady-state level in a cell. If degradation of such a short-lived reporter is inhibited, its steady-state level will rise, enabling the detection of reporter. The level of fluorescent protein can be determined using fluorescence detection, for example, using a fluorimeter or fluorescence microscope. The relative amount of fluorescence can be compared between cells treated with a test agent and untreated cells (or cells treated with a molecule that is similar to the test agent but otherwise known to be inactive). Additional reporter proteins include, for example, a light-generating protein such as luciferase, wherein the amount of light produced can be measured and compared in cells treated with a test agent and in untreated cells, which can be the same cells as those treated with the test agent, but examined prior to addition of the test agent.

The level of reporter protein present can also be determined enzymatically. For example, enzymes capable of making a calorimetric change in a substrate, can be detected indirectly. For example, *E. coli* β-galactosidase (βgal) can be detected through a calorimetric change it causes in the substrate X-gal (5-bromo-4-chloro-3-indolyl-β-D-galactosidase). Making a reporter of this class short-lived in vivo would strongly diminish its steady-state level in a cell. If degradation of such a short-lived reporter is inhibited, its steady-state level will rise, enabling the detection of the reporter protein (through an enzymatic reaction).

Test agents (e.g., of a library of test agents) and/or agents that are tentatively identified as having a desired modulating activity (e.g., reducing or inhibiting R-transferase activity) can be further examined, if desired, in control assays to confirm that they act by inhibiting N-terminal arginylation of an Asp, Glu, or oxidized Cys residue. One way to confirm such activity is to add the putative agent to an otherwise identical mammalian cell culture that expresses, for example, Arg-GFP, which is similar to an Asp-GFP reporter protein except for having an N-terminal Arg instead of Asp, wherein the Arg-GFP reporter is degraded by the N-end rule pathway in an arginylation-independent manner. A test agent (or previously identified agent) that inhibits degradation of the Asp-GFP reporter, but that does not significantly inhibit degradation of the Arg-GFP reporter, would be confirmed as being an R-transferase inhibitor.

Confirmation of inhibition of R-transferase can be obtained in any of several ways. For example, confirmation can be made using an in vivo system, by isolating Asp-GFP from cells treated with inhibitor versus control (untreated) cells, and N-terminally sequencing Asp-GFP from these two sources, to determine whether its N-terminal arginylation was, in fact, inhibited in vivo by the compound in question. Confirmation also can be made using a direct enzymatic assay with purified R-transferase, and testing the identified agent (identified by an initial screen) for inhibition of N-terminal arginylation of a model substrate in vitro.

Where a test agent is identified as N-end rule pathway modulating activity, a screening assay of the invention can further include a step of determining an amount by which the agent increases or decreases arginylation and/or protein degradation. For example, where an agent is identified that reduces or inhibits N-end rule pathway mediated arginylation activity in a cell, a method of the invention can further include determining an amount by which the agent decreases the activity below a desired level (e.g., below detection of the particular method used to measure the activity). Such an agent can be identified by measuring the amount of N-end rule pathway mediated arginylation of a substrate peptide having, for example, an N-terminal mediated Cys residue in a single sample both before adding the test agent and after adding the test agent, or can be identified for example, using two samples, wherein one sample serves as a control (no test agent added) and the other sample includes the test agent. As such, a method of the invention provides a means to obtain agents or panels of agents that variously modulate N-end rule pathway mediated arginylation activity, including protein degradation dependent on the pathway.

A screening assay of the invention also provides a means to determine an amount of a particular agent useful for effecting a desired level of activity of the arginylation branch of the N-end rule pathway. Such a method can be performed by contacting aliquots of a sample with different amounts of the same or different test agents or different amounts of the same or different agents previously identified as having N-end rule pathway modulating activity. As such, the methods of the invention can be used to confirm that an agent believed to have a particular activity, in fact, has the activity, thus providing a means, for example, to standardize the activity of the agent.

The screening method of the invention is readily adaptable to high throughput format, thus allowing for the screening, in parallel, of one or more test agents using one or more samples, wherein the agents and/or samples independently are the same or different. As such, the method allows for testing one or more concentrations of one or more test agents to identify a concentration of an agent particularly useful for modulating the activity of the arginylation branch of the N-end rule mediated pathway, including agents that act at various steps of the pathway (e.g., S-nitrosylation and/or oxidation of an N-terminal Cys of a substrate peptide, arginylation of a substrate peptide by an R-transferase, or ubiquitinylation of the substrate peptide). Further, the method allows for examining several same test agents on one or a plurality of same samples, thus providing a means to obtain statistically significant results. In various aspects, the high throughput format can be used for screening one or a plurality of cell sample(s), for example, samples taken from a subject having a physiological or pathological disorder associated with the arginylation branch of the N-end rule pathway (e.g., impotence, or schizophrenia), with one or a plurality of the same (e.g., different concentrations) or different test agents, to identify an agent and/or concentration of agent that is best suited for modulating the pathway and ameliorating the disorder.

When performed in a high throughput (or ultra-high throughput) format, the method can be performed on a solid support (e.g., a microtiter plate, a silicon wafer, or a glass slide), wherein samples to be contacted with a test agent are positioned such that each is delineated from each other (e.g., in wells). Any number of samples (e.g., 96, 1024, 10,000, 100,000, or more) can be examined in parallel using such a method, depending on the particular support used. Where samples are positioned in an array (i.e., a defined pattern), each sample in the array can be defined by its position (e.g., using an x-y axis), thus providing an "address" for each sample. An advantage of using an addressable array format is that the method can be automated, in whole or in part, such that reagents (e.g., test agents) can be dispensed in (or removed from) specified positions at desired times, and samples (or aliquots) can be monitored for the desired activity.

When used in a high throughput format, a method of the invention provides a means to conveniently screen combinatorial libraries of test agents, which can be a library of random test agents, biased test agents (see, for example, U.S. Pat. No. 5,264,563, which is incorporated herein by reference), or variegated test agents (see, for example, U.S. Pat. No. 5,571,698, which is incorporated herein by reference), in order to identify those agents that can modulate the activity of the arginylation branch of the N-end rule pathway. Methods for preparing a combinatorial library of molecules that can be screened for such modulating activity are well known in the art and include, for example, methods of making a phage display library of peptides, which can be constrained peptides (see, for example, U.S. Pat. No. 5,622,699; U.S. Pat. No. 5,206,347; Scott and Smith, *Science* 249:386-390, 1992; Markland et al., *Gene* 109:13 19, 1991; each of which is incorporated herein by reference); a peptide library (U.S. Pat. No. 5,264,563, which is incorporated herein by reference); a library of peptide derivative compounds such as a hydroxamate compound library, reverse hydroxamate compound library, a carboxylate compound library, thiol compound library, a phosphinic peptide library, or phosphonate compound library (see, for example, Dive et al., *Biochem. Soc. Trans.* 28:455-460, 2000; Ye and Marshall, "Peptides: The Wave of the Future" (Lebl and Houghten, ed.; American Peptide Society, 2001), each of which is incorporated herein by reference); a peptidomimetic library (Blondelle et al., *Trends Anal. Chem.* 14:83 92, 1995, which is incorporated herein by reference); a nucleic acid library (O'Connell et al., *Proc. Natl. Acad. Sci., USA* 93:5883-5887, 1996; Tuerk and Gold, Science 249:505-510, 1990; Gold et al., *Ann. Rev. Biochem.* 64:763-797, 1995; each of which is incorporated herein by reference); an oligosaccharide library (York et al., *Carb. Res.* 285:99-128, 1996; Liang et al., *Science* 274:1520 1522, 1996; Ding et al., *Adv. Expt. Med. Biol.* 376:261 269, 1995; each of which is incorporated herein by reference); a lipoprotein library (de Kruif et al., *FEBS Lett.* 399:232 236, 1996, which is incorporated herein by reference); a glycoprotein or glycolipid library (Karaoglu et al., *J. Cell Biol.* 130: 567 577, 1995, which is incorporated herein by reference); or a chemical library containing, for example, drugs or other pharmaceutical agents (e.g., small organic molecules having a molecular weight of about 1000 daltons (Da) or less; see, for example, Gordon et al., *J. Med. Chem.* 37:1385-1401, 1994; Ecker and Crooke, *BioTechnology* 13:351-360, 1995; each of which is incorporated herein by reference).

Modulation of the arginylation branch of the N-end rule pathway provides a means to manipulate the physiology of a subject and to ameliorate abnormal physiological conditions and/or pathologic conditions in the subject. Accordingly, agents that can modulate the arginylation branch of the N-end rule pathway, including agents identified by the screening assays of the invention, can be useful as a medicament for treating various physiological and pathological conditions in animals, including mammals (e.g., humans). The animal subject to be treated can be any organism that has a condition that can be manipulated by modulating the arginylation branch of the N-end rule pathway, and generally is a mammalian organism, particularly a human. Conditions amenable to treatment using an agent that modulates the arginylation branch of the N-end rule pathway can include, for example, conditions in which it is desired to increase or decrease angiogenesis (e.g., cancer and other tumor growth, including metastasis of cancer cells; rheumatoid arthritis, psoriasis, rosacea; coronary artery disease; stroke; and wound healing); conditions that are treated using drugs that have the effect of increasing or decreasing nitric oxide levels in the subject (e.g., impotence, which is treated, for example, with sildenafil citrate (Viagra®); and angina, which is treated with nitroglycerin); conditions characterized by abnormal levels of apoptosis (e.g., cancer); and other conditions characterized by altered levels or activities of N-end rule pathway components such as R-transferase levels or activity (e.g., schizophrenia, in which increased activity of the arginylation branch of the N-end rule pathway can cause the decreased levels of RGS4 associated with the disorder).

As disclosed herein, the arginylation branch of the N-end rule pathway is involved in various physiological and pathological conditions and, therefore, can be modulated in order to alter such physiological and/or pathological conditions as desired. As such, the invention provides methods of ameliorating a condition or disorder associated with the arginylation branch of the N-end rule pathway, including, for example, conditions associated with abnormal levels of protein degradation. As used herein, the term "ameliorate" means that signs and/or symptoms of a pathologic condition are reduced (lessened). Such a method can be performed by administering to the subject an agent that modulates the arginylation branch of the N-end rule pathway.

Amelioration of a condition can be identified using any assay generally used to monitor the clinical signs or the symptoms of the particular condition. For example, amelioration of a wound can be identified by monitoring closure or healing of the wound, and amelioration of a cancer can be identified by detecting reduced angiogenesis and/or vascularization of a tumor, or by detecting a change in the level of apoptosis occurring in the cancer cells following administration of the agent. In addition, amelioration can be identified by the subject indicating that the treatment with an agent is effective, for example, in treating impotence or angina.

Where the agent is to be used for a therapeutic method, it can be formulated in a form suitable for administration to a subject, for example, as a pill or a liquid, and can be administered, for example, orally, by injection, or via inhalation. Accordingly, compositions, including medicaments, useful for treating a subject having a condition amenable to treatment using an agent that modulates the activity of the arginylation branch of the N-end rule pathway are provided. A composition for administration to a living subject generally includes formulating the agent in a pharmaceutically acceptable composition. Such compositions are well known in the art and include, for example, aqueous solutions such as water or physiologically buffered saline or other solvents or vehicles such as glycols, glycerol, oils such as olive oil or injectable organic esters. The composition also can contain physiologically acceptable compounds that act, for example, to stabilize or to increase the absorption of the agent. Such physiologically acceptable compounds include, for example, carbohydrates, such as glucose, sucrose or dextrans, antioxidants, such as ascorbic acid or glutathione, chelating agents, low molecular weight proteins or other stabilizers or excipients.

One skilled in the art would know that the choice of a composition, including a physiologically acceptable compound, depends, for example, on the physico-chemical characteristics of the agent to be administered, and on the route of administration of the composition, which can be, for example, orally or parenterally such as intravenously, and by injection, intubation, inhalation, or other such method known in the art. The composition also can contain one or more additional reagents, including, for example, nutrients or vitamins or, where the composition is administered for a therapeutic purpose, a diagnostic reagent or therapeutic agent relevant to the disorder being treated.

The composition can be administered to a subject by any of various routes including, for example, orally or parenterally, such as intravenously, intramuscularly, subcutaneously, intraorbitally, intracapsularly, intraperitoneally, intrarectally, intracisternally or by passive or facilitated absorption through the skin using, for example, a skin patch or transdermal iontophoresis, respectively. Furthermore, the composition can be administered by injection, intubation, orally or topically, the latter of which can be passive, for example, by direct application of an ointment, or active, for example, using a nasal spray or inhalant, in which case one component of the composition is an appropriate propellant.

As disclosed herein, agents identified by the screening assays of the invention can be used in various aspects to modulate the susceptibility of plants to infection by pathogens or the severity of a pathogenic infection in plants. Accordingly, the invention provides methods of modulating the severity of infection or susceptibility of a plant to infection by a pathogen. Plant pathogens such as *Pseudomonas* and other bacteria inject, via the type III system, specific proteins, including proteases, into plant cells, which express resistance proteins ("R-proteins"). One such protease, AvrRpt2, upon injection into *Arabidopsis* plant cells, cleaves RIN4, which is an *Arabidopsis* R-proteins (see Chisholm et al., *Proc. Natl. Acad. Sci., USA* 102:2087-2092, 2005, which is incorporated herein by reference). Cleavage of RIN4 by the protease injected by the pathogen leads to rapid disappearance of the C-terminal fragment of RIN4, an event that contributes to the initiation of the hypersensitive (protective) response by the plant. As disclosed herein, the cleavage sites such as that generated upon cleavage of RIN4, produces secondary destabilizing N-terminal residue(s) in the RIN4 fragment, which can be arginylated by an R-transferase such as that encoded by ATE1. Chisholm et al. also report that there at least 20 additional plant proteins that can be cleaved by AvrRpt2. As disclosed herein, the N-terminal residues of cleavage products of several of these plant proteins include Glu, Asp, and Cys, which are destabilizing and subject to N-end rule pathway mediated arginylation, indicating that the short half-lives of the AvrRpt2-cleaved fragments, which is a property that is key to hypersensitive response, can be due to the arginylation branch of the N-end rule pathway. As such, the present invention provides a means to regulate the hypersensitive response circuit in plants by modulating N-end rule pathway mediated arginylation in plant cells that are infected, or susceptible to infection, with a pathogen.

The following examples are intended to illustrate but not limit the invention.

EXAMPLE 1

Oxidation of N-Terminal Cysteiene Redsidues by Nitric Oxide in the Presence of Oxygen This example demonstrates that nitric oxide, in the presence of oxygen, directly oxides an N-terminal cysteine residue in a peptide, thus converting the cysteine residue for arginylation in the N-end rule pathway or protein degradation.

Mammalian R-transferases are strong sequelogs[1] of yeast (fungal) ATE1 R-transferases. However, while the inactivation of mouse ATE1 results in embryonic lethality[2], a deletion of *S. cerevisiae* ATE1 renders cells unable to degrade reporters with N-terminal Asp or Glu but has not been found to cause any other abnormal phenotype[3,4]. Our findings suggest that one function of arginylation might be to serve as a sensor of nitrosative/oxidative stress. Animals and plants employ NO in their defense against infections. Both prokaryotic and eukaryotic pathogens have anti-NO systems[5,6]. Although prokaryotes lack Ub conjugation and Ub itself, many of them, including *E. coli,* have a version of the N-end rule pathway[7]. In one of possible models, the NO-mediated oxidation of N-terminal Cys in a "sentinel" protein of invading pathogen causes arginylation and degradation of this protein, thereby initiating a protective response. Remarkably, most proteobacteria (but not *E. coli*) contain sequelogs of eukaryotic (ATE1) R-transferases. Moreover, the substrate specificity of these prokaryotic enzymes has been found to be similar to that of yeast and mammalian ATE1.

Methods

Mouse Embryos, Immunoblotting, and Northern Hybridization

Heterozygous ATE1$^{+/-}$ mice of the mixed C75BL/6J-129SvEv background were maintained and mated at the Caltech's Transgenic Facility as described[2,8,12]. E12.5 and E14.5 embryos were collected with precautions to avoid contamination by maternal tissues 3. Given the embryonic lethality of the ATE1$^{-/-}$ genotype, only live (with beating hearts) embryos were selected for dissection and isolation of tissues such as head, liver, heart, and lungs. Genotyping of embryos was done using standard procedures[2,9,11]. Genotyped embryos of the same age and genotype were either pooled or used individually. Embryos or their specific tissues were lysed, with homogenization by a motorized pestle (Kontes), in LB1 buffer (1% Triton-X100, 0.4 M NaCl, 10% glycerol, 20 mM Tris-HCl (pH 8.0)) containing mammalian protease inhibitor cocktail (Sigma) and 2 mM phenylmethylsulfonyl fluoride (PMSF), from freshly prepared 0.5 M stock solution in isopropanol. The extracts were centrifuged at 16,000 g for 15 min at 4° C., and the supernatants were processed for immunoblotting (IB) with antibodies against several proteins (see below and the main text). Total protein concentrations for IB were determined using Bradford assay (BioRad). To further verify, and improve if necessary, the uniformity of total protein loads from lane to lane, proteins were stained with Ponceau-S after their electrophoretic transfer to PVDF membranes[11]. In addition, a polyclonal antibody to GAPDH (glyceraldehyde-3-phosphate dehydrogenase) (Santa Cruz) was used with some immunoblots (e.g., the main text, FIG. 3a, lanes-9-11) to verify the uniformity of loads. The membranes were incubated for 2 h with U1079 polyclonal antibody to a fragment of the rat RGS4 protein[14] (a gift from Dr. S. Mumby, University of Texas Southwestern Medical Center, Dallas, Tex., USA), or with a polyclonal antibody to the full-length mouse RGS16 protein[15] (a gift from Dr. C. K. Chen (University of Utah, Salt Lake City, Utah, USA) and Dr. M. Simon (Caltech, Pasadena, Calif., USA)), or with a polyclonal antibody to the full-length rat RGS5 protein[16] (a gift from Dr. M. T. Greenwood, McGill University, Montreal, Quebec, Canada). Antisera dilutions, with 5% fat-free milk, varied from 1:300 to 1:2000. Details of IB procedures were largely as described[17]. Other antibodies used in these analyses were to serine racemase (SRR) (BD Biosciences) and to mouse ATE1-1 R-transferase. The latter polyclonal, affinity-purified antibody was raised in rabbits against purified ATE1-1 (see below).

Northern hybridizations were carried out essentially as described[10,11]. Specifically, 15-µg samples of total RNA from +/+ and A TEF1$^{-/-}$ E12.5 embryos were fractionated by electrophoresis in formaldehyde-1% agarose gels, blotted onto Nytran SuPerCharge membranes (Schleicher & Schuell), and hybridized with $^{32}$P-labeled (PCR-produced) RGS4 or RGS16 cDNAs as probes (see the main text and Supplementary FIG. 6a, b).

3T3$^{toff}$RGS4$_{fh}$ Cells, UBR1/2$^{dnR2}$ Cells, and other Cell Lines, Treatments of Cells, Preparation of Extracts, Pulse-Chase, RT-PCR, and Determination of Nitric Oxide To construct a cell line expressing RGS4 from a tetracycline (Tet)-regulated promoter, mouse MEF/3T3 "Tet-off" cells, which expressed the tTA transcriptional activator (BD Biosciences), were transfected at 60-80% confluency, using Lipofectamin-Plus (InVitrogen), with the plasmid pTRE2hygRGS4flagHis6 encoding C-terminally epitope-tagged RGS4-flag-His$_6$ (denoted as RGS4$_{fh}$) downstream from a Tet-responsive promoter. This plasmid was constructed using pTRE2hyg vector (BD Biosciences). Hygromycin (0.25 mg ml$^-$) was added 24 h after transfection. Hygromycin-resistant colonies were expanded and tested, by immunoblotting with the monoclonal antibody M2 to the flag epitope (Sigma), for doxycyline-repressible expression of RGS4$_{fh}$. A cell line, termed 3T3$^{toff}$RGS4$_{fh}$, that was chosen for this study, was grown at 37° C. in 10% tetracycline-free fetal bovine serum (FBS) (BD Biosciences) plus DMEM (InVitrogen), in the presence of doxycycline (1 µg ml$^{-1}$). To express RGS4$_{fh}$, ~40% confluent cultures in 10-cm plates were washed twice with DMEM, then incubated for 12 h in DMEM plus 10% tetracycline-free FBS. The medium was replaced with the same but fresh medium (~9 ml per plate), and the cells were incubated for another 24 h before harvesting and preparation of extracts.

Treatments of 3T3$^{toff}$RGS4$_{fh}$ cells with NO scavenger 2-(4-carboxyphenyl)-4,5-dihydro-4,4,5,5-tetramethyl-1H-imidazolyl-1-oxy-3-oxide (CPTIO, at 0.2 mM; Calbiochem), N$^G$Monomethyl-L-arginine (LMMA, at 1 mM; Cayman Chemical), or the proteasome inhibitor MG132 (at 20 µM; Calbiochem) were carried out with 80-90% confluent cultures in 10-cm plates for 4 h, followed by preparation of extracts and IB with anti-RGS4 antibody. The procedures were identical to those used with embryos, except that cells were scraped off the plate and lysed, using a motorized pestle, in 0.05% Tween 20, 0.3 M NaCl, 10 mM 2-mercaptoethanol (2-ME), 20 mM imidazole, 50 mM K-phosphate (pH 8.0). Treatments of cells with L-N$^w$-Nitroarginine-2,4-L-diaminobutyric amide (Sigma: #N3411), a NOS inhibitor highly specific for NOS1 (nNOS)[18], were carried out at either 0.5 mM or 1 mM N3411 for 15 h, with changes of (inhibitor-containing) medium every 3 h.

Another mouse cell line, UBR1/2$^{dnR}$ cells, stably expressed UBR2$^{1041}$, the dominant-negative N-terminal half of the mouse UBR2 E3 Ub ligase, from the $P_{CMV}$ promoter. This line was constructed from a double-mutant [UBR-1$^{-/-}$ UBR2$^{-/-}$] EF cell line; the latter was produced as described in ref. 10 and the main text. The UBR1/2$^{dnR2}$ cells and the parental [UBR1$^{-/-}$UBR2$^{-/-}$] cell line were maintained in DMEM plus 10% FBS (Gibco). Other cell lines used were NIH-3T3 and ATE1$^{-/-}$ EF cells[2].

Pulse-chases were carried out with 3T3$^{toff}$RGS4$_{fh}$ cells, essentially as described for other mouse cell lines[2], using 10-min pulses with $^{35}$S-EXPRESS (Perkin-Elmer) and chases for 1 and 2 h, followed by extraction of proteins, immunoprecipitation with anti-RGS4 antibody, 15% SDS-PAGE, and autoradiography. CPTIO treatments of NIH-3T3 cells, ATE1$^{-/-}$ EF cells, and 3T3$^{toff}$RGS4$_{fh}$, cells were carried out as described above, except that 4 h before the end of 24-h incubation with CPTIO, the medium was replaced by fresh CPTIO-containing medium.

Low-oxygen growth (0.5% vs. 21% O$_2$) of 3T3$^{toff}$RGS4$_{fh}$ cells in the absence of doxycyline was carried out for 24 h, followed by SDS-PAGE and immunoblotting with antibody to RGS4, as described above. The gas for low-oxygen regimen was 0.5% O$_2$, 5% CO$_2$, 94.5% N$_2$. The incubation chamber was from Biospherix (USA).

RT-PCR with total RNA from cells indicated in the legend to FIG. S3 was carried out essentially as described[11,19], using previously described primers and protocols[20]. Mouse NOS1 (nNOS)-specific primers, for the 281 bp NOS1 fragment (nt 2,529-2,809), were 5'-AATGGAGACCCCCCAGAGAAT (sense) (SEQ ID NO:4) and 5'-TCCAGGAGAGTGTC-CACTGC (antisense) (SEQ ID NO:5). NOS2 (iNOS)-specific primers, for the 468 bp NOS2 fragment (nt 88-428), were 5'-ACGCTTGGGTCTTGTTCACT (sense) (SEQ ID NO:6) and 5'-GTCTCTGGGTCCTCTGGTCA (antisense) (SEQ ID NO:7). NOS3 (eNOS)-specific primers, for the 231 bp (nt 1,202-1,433) fragment, were 5'-AAGACAAGGCAGCG-GTGGAA (sense) (SEQ ID NO:8) and 5'-GCAGGGGA-CAGGAAATAGTT (antisense) (SEQ ID NO:9). GAPDH (control)-specific primers, for the 357 bp fragment, were 5'-CATCACCATCTTCCAGGAGCG (sense) (SEQ ID NO: 10) and 5'-GAGGGGCCATCCACAGTCTTC (antisense) (SEQ ID NO:11). For reverse transcription[11], 3 μg of total RNA from cell lines indicated in FIG. S3 were used in 20 μl of Retro-Transcription buffer with SuperScript-II reverse transcriptase (InVitrogen). Thereafter 3 μl were taken for either 27 cycles (GAPDH) or 35 cycles (NOS1-NOS3) of PCR in 50-μl samples containing 2.5 units of Taq polymerase. The primers were at 50 pM each[20].

Synthesis of Fmoc-L-Cysteic Acid ($CysO_3H$)

To a water solution (5 ml) of L-cysteic acid monohydrate (0.82 g, 4.38 mmol) were added, successively, 1 N NaOH (5.25 ml, 5.25 mmol) and 9-fluorenylmethyl succinimidyl carbonate (FmocOSu) (2.95 g, 8.76 mmol) in dioxane (25 ml). After stirring at room temperature overnight, the solution was concentrated in vacuo, followed by the addition of water (75 ml). The resulting mixture was washed with ethyl acetate (37.5 ml). The organic phase was extracted with water (25 ml), and the combined aqueous phases were washed with ethyl acetate(40 ml). The aqueous phase was concentrated in vacuo. The residue was co-evaporated with toluene in vacuo (3×50 ml), yielding a solid. Absolute ethanol (75 ml) was added, and the suspension was incubated for 1 h at 60° C., then cooled to room temperature. The white solid was collected by filtration and dried in vacuo, yielding 1.45 g of pure Fmoc-$CysO_3H$. MS: m/z 390.2 $[M-H]^-$. Calculated mass of $C_{18}H_{17}O_7NS$: 391.1.

Synthesis of Asp-Peptide, Cys-Peptide, and $CysO_3H$-Peptide

The 8-residue Asp-peptide (DHGSGAWL, SEQ ID NO:1 in single-letter abbreviations for amino acids) and the otherwise identical Cys-peptide (CHGSGAWL) (SEQ ID NO:2) were synthesized using standard methods[21], and purified by HPLC. The 7-residue HGSGAWL (SEQ ID NO:3) sequence that followed the varying N-terminal residue, was identical to the residues 2-8 of X-$e^K$βgal, a previously utilized, $E.\ coli$ β-galactosidase-based reporter substrate of the N-end rule pathway, with $e^K$ (extension (e) containing lysines (K)) denoting a 45-residue sequence that precedes the sequence of β-galactosidase[21]. Also synthesized and purified was the 7-residue peptide HGSGAWL (SEQ ID NO:3), which was then coupled to Fmoc-$CysO_3H$ as described below. Into one 2-ml microcentrifuge tube was placed the carrier resin linked to C-terminus of the HGSGAWL peptide (12.5 μmol) and 0.5 ml dimethylformamide (DMF), followed by stirring for 10 min at room temperature. Into another microcentrifuge tube were placed Fmoc-$CysO_3H$ (14.7 mg, 37.5 μmol), 0.2 ml DMF, 188 μl of 0.2 M HBTU in 0.2 M HOBt/DMSO/NMP solution (37.5 μmol HBTU and 37.5 μmol HOBt), and 188 μl of 0.4 M DIEA/DMSO/NMP (75 μmol DIEA, Applied Biosystems #401254). (0.2 M HBTU in 0.2 M HOBt/DMSO/NMP solution was made by dissolving 8 mmols HBTU (Applied Biosystems, #401278) in 40 ml 0.2 M HOBt/DMSO/NMP (Applied Biosystems, #401279).) The mixture was turbid at first, then it became clear. It was stirred for 10 min, then added to the carrier resin in DMF, and the suspension was stirred for 0.5 h at room temperature. The reaction mixture was washed 3 times with DMF, centrifuged, and the upper DMF layer was discarded. The resin was washed with stabilized THF twice, dried using Speedvac (Savant), deprotected with piperidine first, washed with DMF, then treated for 1 h at room temperature with 1.1 ml of trifluoroacetic acid (TFA), 62.5 μl 1,2-ethanedithiol, and 62.5 μl thiolanisole. Thereafter 12 ml of methyl tert-butyl ether were added, the mixture was vortexed, centrifuged at 15,000 g for 5 min, and the supernatant was discarded. The precipitate was washed twice with methyl tert-butyl ether. The precipitate was in two layers, with the $CysO_3H$-peptide and the resin beads forming the upper and lower layer, respectively. Water (2 ml) was added to dissolve $CysO_3H$-peptide, followed by filtration through a cotton-plugged pipette. The solution was dried under vacuum, and $CysO_3H$-peptide was purified by HPLC.

Recombinant Proteins

*S. cerevisiae* Arg-tRNA synthetase. The plasmid pTrc99-B, which expressed untagged *S. cerevisiae* Arg-tRNA synthetase (RRS1) in *E. coli*[21], was a gift from Dr. G. Eriani (Institut de Biologie Moleculaire et Cellulaire, Strasbourg, France). The protocol below was derived, in part, from unpublished procedures by Drs. M. G. Xu and E. D. Wang (Shanghai Institutes of Biochemistry and Cell Biology, PR China). Expression of RRS1 was induced in *E. coli* JM109 carrying pTrc99-B, using IPTG at 0.5 mM, as described[21]. The cells were lysed by sonication after digestion with lysozyme in lysis buffer A (50 mM K-phosphate, pH 7.5). The lysate were centrifuged at 15,000 g for 30 min at 4° C. in the RC-5B centrifuge (Sorvall). The supernatant was loaded onto a column of Cibacron Blue Sepharose (Sigma), which was then washed with 10 volumes of lysis buffer, followed by 5 volumes of washing buffer (0.15 M K-phosphate, pH 7.5). RRS was then eluted with 0.5 M K-phosphate, pH 7.5). Glycerol was then added to the final concentration of 50%. Multiple samples of RRS1 were stored at −80° C.

*S. cerevisiae* ATE1 Arf-tRNA-protein transferase (R-transferase)[3]. Yeast ATE1 C-terminally tagged with $His_6$ and denoted below as scATE1$h_6$, was expressed in *E. coli* BL21 (co-transformed with Arg-, Ile-, and Leu-tRNAs to increase expression of eukaryotic proteins) from the plasmid pPET-11d, constructed by Dr. F. Du (Yale University, New Haven, Conn., USA). The expression of scATE1$h_6$ was induced with 1 mM IPTG for 6 h at 30° C., followed by lysis (as described above for RRS1) in lysis buffer B (0.15 M NaCl, 5 mM 2-mercaptoethanol (2-ME), 20 mM imidazole, 20 mM Tris-HCl (pH 8.0)) and centrifugation at 15,000 g for 30 min at 4° C. The supernatant was loaded onto Ni-NTA-agarose (Qiagen). The column was washed with 10 volumes of lysis buffer B and 5 volumes of washing buffer B (0.3 M NaCl, 5 mM 2-ME, 20 mM imidaiole, 20 mM Tris-HCl, (pH 8.0)). scATE1$h_6$ was were then eluted with 2 volumes of elution buffer B (0.3 M NaCl, 5 mM 2-ME, 0.25 M imidazole, 20 mM Tris-HCl, (pH 8.0)). Imidazole was removed by three centrifugations in Centriplus (Millipore) equilibrated with 2× storage buffer (see below), followed by addition of glycerol to the final concentration of 50%. Multiple samples of scATE1$h_6$ were stored at −80° C. in 50% glycerol, 0.15 M NaCl, 2 mM dithiothreitol (DTT), 20 mM Tris-HCl (pH 8.0)).

Mouse ATE1-1 R-transferase. ATE1-1, one of mouse ATE1-encoded, splicing-derived isoforms of R-transferase[2,19], was C-terminally tagged with the "polyoma" and $His_6$ epitopes[11]. The resulting construct is denoted as mATE1-1p$h_6$. Construction of the corresponding open reading frame (ORF) was carried out using PCR (with verification by DNA sequencing), followed by subcloning into the BamHI/XhoI-cut baculovirus plasmid pBacPAK8 (BD-Clontech), a step that yielded the plasmid pBacPAK8-mATE1-1p$h_6$. mATE1-1p$h_6$ was expressed and purified at the Caltech's Protein Expression and Purification facility. The recombinant baculovirus was obtained after co-transfecting IPLB-SF9 cells with pBacPAK8-mATE1-1p$h_6$ and linearized viral DNA (Baculogold, Pharmingen). High-titer recombinant baculovirus was then employed to infect High-Five cells (InVitrogen), followed by incubation at 27° C. for 60-70 h. Cells were harvested by centrifugation at 300 g for 10 min at 4° C., and the steps below were also performed at 4° C. Cell pellets were resuspended and lysed by gentle vortexing in 10 volumes of lysis buffer C (1% NP-40, 0.1 M NaCl, 10 mM $MgCl_2$, 5 mM 2-ME, 20 mM Tris-HCl (pH 830)) containing protease inhibitor cocktail (Sigma). The lysate was then centrifuged at 13,000 g for 15 min at 4° C. The supernatant was retained. The pellet was rehomogenized in 5 volumes of lysis buffer C, centrifuged as above, and the supernatants, denoted as S 13, were combined. 1 M imidazole and 5 M NaCl were then added to S13 to the final concentrations of 10 mM and 0.3 M, respectively. Ni-NTA-agarose (Qiagen; 3 ml) pre-equilibrated with lysis buffer C, was added to S13, and the mixture was gently rotated for 2 h at 4° C. Ni-NTA beads were collected by centrifugation at 300 g for 5 min, then transferred to a plastic column (Pierce) and washed with 10 volumes of wash buffer C1 (0.05% NP-40, 0.3 M NaCl, 10 mM $MgCl_2$, 5 mM 2-ME, 20 mM imidazole, 20 mM Tris-HCl (pH 8.0)), followed by washes with 5 volumes of wash buffer C2 (0.1 M NaCl, 10 mM $MgCl_2$, 5 mM 2-ME, 20 mM imidazole, 20 mM Tris-HCl, (pH 8.0)). mATE1-1$ph_6$ was then eluted with 6 volumes of elution buffer C (0.1 M NaCl, 5 mM 2-ME, 0.25 M imidazole, 20 mM Tris-HCl, (pH 8.0)). Imidazole was then removed and multiple samples of mATE1-1 $ph_6$ were frozen as described above for scATE1$h_6$.

X-RGS4 proteins. Cys-RGS4, Asp-RGS4, and Val-RGS4 were produced using a version of the Ub fusion technique[4,22] developed by R. Baker and colleagues[23]. DNA fragments encoding C-terminally flag-tagged X-RGS4 proteins were cloned into SacII/KpnI-cut Ub-fusion-based *E. coli* vector pHUE (a gift from Dr. R. Baker, Australian National University, Canberra, Australia)[23]. Competent *E. coli* (BL21-Codon Plus (DE3)-RIL; Stratagene) were transformed with plasmids (verified by DNA sequencing) that encoded $His_6$-Ub-X-RGS4-flag (X=Cys, Asp or Val). Expression was induced with 0.5 mM IPTG (starting at $OD_{600}$ of 0.75) for 6 h at 25° C. The cells were harvested, and lysed with lysozyme, followed by a brief sonication in buffer C (0.5% Tween-20, 0.3 M NaCl, 10 mM 2-mercaptoethanol (ME), 20 mM imidazole, 50 mM K-phosphate (pH 8.0)) and mammalian protease inhibitor cocktail (Sigma). The lysate was clarified by centrifugation at 15,000 g at 4° C. for 20 min, and the supernatant was loaded onto Ni-NTA-agarose (Qiagen). The column was washed with 10 volumes of lysis buffer C and 5 volumes of washing buffer B (0.3 M NaCl, 5 mM 2-ME, 20 mM imidazole, 20 mM Tris-HCl (pH 8.0)). A $His_6$-Ub-X-RGS4-flag protein was eluted with 2 volumes of buffer B (0.3 M NaCl, 5 mM 2-ME, 0.25 M imidazole, 20 mM Tris-HCl (pH 8.0)). Imidazole was removed by three centrifugations in Centriplus (Millipore) equilibrated with 0.5×-buffer° C. The eluted protein were digested with purified $His_6$-USP2-cc deubiquitylating enzyme[23] (a gift from Dr. Z. Xia, Caltech, Pasadena, Calif., USA) for 8 h at 16° C. The yield of X-RGS4-flag was typically ~80%. Ni-NTA agarose beads were used to remove undigested $His_6$-Ub-X-RGS4-flag and the $His_6$-USP2-cc enzyme[23]. The resulting X-RGS4-flag proteins were more than 90% pure, as verified by 12% SDS-PAGE and staining with Coomassie.

Antibody to Mouse ATE1

Purified full-length mouse mATE1-1$ph_6$ (~1.5 mg; see above) was used to produce rabbit antisera (Covance, Berkeley, Calif., USA). After second bleeding, antisera were collected and mixed with 1/9 volume of 10× HBT buffer (0.1% Tween-20, 0.3 M NaCl, 20 mM HEPES (pH 7.5)). After centrifugation at 13,000 g, the supernatant was passed through a column of Affigel-10 (BioRad) containing an unrelated conjugated protein bearing $His_6$ tag. The flow-through fraction (10 ml) was then incubated with Affigel-10 beads conjugated to purified mATE1-1$ph_6$. After 2 hours at 4° C., with gentle rocking, the sample was loaded into 5-mi disposable columns, letting excess liquid flow from the beads. Each column was then washed with 20 bed volumes of HBT buffer, followed by 5 bed volumes of HBT buffer containing 0.5 M NaCl. Antibodies bound to the beads were then eluted with 0.2 M glycine (pH 2.8), with pH of eluted fractions adjusted to 8.0 with 1 M Tris immediately after elution. The first 5 0.75-ml fractions were pooled and dialyzed against PBS buffer (0.15 M NaCl, 50 mM K-phosphate, pH 7.5) followed by the addition of glycerol top 20% and storage at −20° C. The specificity of affinity-purified anti-ATE1 antibody is illustrated in FIG. S2c. For immunoblotting with anti-ATE1 antibody, pre-blocked PVDF membrane was incubated with anti-ATE1 diluted 1:2000 ($OD_{280}$ of ~0.2) in 5% nonfat milk, 0.1% Tween-20, and PBS) for 2-4 hours. The rest of immunoblotting procedure was as described above.

R-Transferase Assay, Capillary Electrophoresis (CE), and Mass Spectrometry (MS)

A sample for carrying out the arginylation of reporter peptides contained, in the total volume of 50 µl: 5 mM dithiothreitol (DTT), 25 mM KCl, 5 mM $MgCl_2$, 7.5 mM arginine-HCl, 10 mM ATP, 20 mM HEPES (pH 7.5); one of three 8-residue synthetic peptides, denoted as Asp-peptide, Cys-peptide, and $CysO_3$-peptide (see above and the main text), at 0.15 mM; a mixture of *S. cerevisiae* tRNAs, 20 µg (Sigma; it was further purified by phenol-chloroform extraction, ethanol-precipitated, and redissolved in 10 mM Tris-HCl (pH 7.5), using diethylpyrocarbonate-treated water; *S. cerevisiae* Arg-tRNA synthetase (RRS1; expressed in *E. coli* and purified as described above), 0.75 µg; and either the purified mouse ATE1-1 R-transferase or the purified *S. cerevisiae* ATE1 R-transferase, at 50 nM. Before the addition of R-transferase (the last component), a sample was incubated at 37° C. for 15 min to accumulate Arg-tRNA. Arginylation of an X-peptide was carried out 37° C. with mouse ATE1-1 and at 30° C. with yeast ATE1. Reactions were stopped by adding trifluoroacetic acid (TFA) to the final concentration of 0.2%. The resulting samples were mixed well and kept on ice for 15 min, then centrifuged at 16,000 g for 15 min at 4° C., and the supernatants were collected for isolation of peptides using Ziptip-C18 (Millipore), according to manufacturer's instructions. The peptide competition-based R-transferase assay was carried out as above (with either the scATE1$h_6$ or the mATE1-1$ph_6$ R-transferase at 50 nM), and with the following modifications: the pH of assay buffer was 9.0; the concentration of each of the three peptides in the mixture was 50 µM; the reaction time was 30 min.

For MS (MALDI-TOF) analysis, 0.5 µl of eluate from Ziptip-C 18 were mixed with 0.5 µl of α-cyano-4-hydroxycinnamic acid (α-CN) matrix solution (saturated solution in 0.5% TFA, 50% acetonitrile), and spotted onto plates of a 100-well gold-plated surface, followed by thorough air-drying. MALDI-TOF spectra were recorded using the Applied Biosystems (ABI) Voyager DE-PRO time-of-flight mass spectrometer. Mass spectra were recorded in reflector delayed extraction mode, with the accelerating voltage of 20 kV, and delay of 100 nsec. The low-mass cutoff gate was set to 500 Da, to prevent lower-mass, matrix-derived ions from saturating the detector. External calibration was employed, using peptide mixture in the mass range of interest (ABI). Raw spectra were acquired with an internal 2 GHz ACQIRIS digitizer and processed with Data Explorer software (ABI). For analysis by capillary electrophoresis (CE), 10 µl of eluate from Ziptip-C 18 were dried in Spin-Vac and redissolved in CE running buffer (16 mM Borate, 1.5% SDS, pH ~8.5). CE was carried out using Applied Biosystems CE model 270A, at 300 kV, recording optical density at 200 nm.

In Vitro Assay for NO-Dependent Arginylation of N-Terminal Cys Residue

The test proteins Cys-RGS4, Asp-RGS4 and Val-RGS4 (see the main text and FIG. 4) were expressed in E. coli as Ub fusions, followed by their in vitro cleavage and purification[23] as described above. Purified X-RGS4s were stored in 50% glycerol, 0.15 M NaCl, 2 mM dithiothreitol (DTT), 20 mM Tris-HCl (pH 8.0) at -80° C. Diglutathionyl-dinitroso-iron (DNIC-[GSH]$_2$) (2 mM, stabilized with 20-fold excess of Glutathione (GSH)) was a gift from Dr. Mulsch[24] and was stored at -196° C. before use. DETA-NO (2,2'-(hydroxynitrosohydrazino)bis-ethanamine) was from Cayman Chemical (USA).

Incubations with NO donors were carried out largely as described[25], with a few modifications. Prior to buffer exchange with S-nitrosylation buffer, 50 μl of TCEP-conjugated agarose beads (Pierce) were added to 1-ml samples of X-RGS4 proteins to preserve the reduced state of N-terminal Cys. Dialysis against S-nitrosylation buffer (50 mM K-phosphate, 0.2 M KCl, 1 mM EDTA (pH 6.9)), using minidialysis kit (mol. weight cutoff 1K; Amersham Biosciences) and one exchange of buffer during dialysis, was carried out for 6 h. TCEP-beads were removed by centrifugation after dialysis. X-RGS4 proteins at 2 μM in S-nitrosylation buffer were incubated without or with 0.1 mM DNIC-[GSH]$_2$) or, alternatively, with 0.3 mM DETA-NO for 1 h at 25° C., with mild rotary shaking on Thermomixer (Eppendorf). The duplicate samples of 0.15 ml were then dialyzed against S-nitrosylation buffer for 12 h at 4° C., with three buffer exchanges, and then dialyzed against arginylation buffer (25 mM KCl, 5 mM MgCl$_2$, 5 mM DTT, 7.5 mM arginine, 20 mM Na-HEPES (pH 7.5)). The dialyzed samples were centrifuged at 13,000 g for 5 min at 4° C. The supernatants were collected, and protein concentrations were determined using Bradford assay (Bio-Rad). Arginylation assay was carried out in 50-μl samples, with 28 nM of purified mATE1-1ph$_6$ and 2.8 μM (about 4 μg total) of either Cys-RGS4, Asp-RGS4, or Val-RGS4. The reaction mixtures contained 1 μM L-[2,3,4,5-$^3$H]arginine-HCl (Amersham, 58.0 Ci/mmole), 2.4 μM cold 1-arginine-HCl, 25 mM KCl, 5 mM MgCl$_2$, 10 mM ATP, 20 mM 5 mM DTT Na-HEPES (pH 7.5), E. coli tRNAs (1.2 μg μl$^-$), and E. coli aminoacyl tRNA synthetases (0.2 μg μl$^{-1}$). The reactions were carried out at 37.5° C. for 1.5 h. One third of the volume of 4×-SDS-PAGE sample buffer was then added, followed by heating at 95° C. for 5 min and 15% SDS-PAGE in a precast gel (BioRad). The gels were treated with $^3$H-Enhancer (Perkin Elmer) as described by the manufacturer, and dried gels were exposed to Kodak BioMax film at -80° C. The loading of equal amounts of X-RGS4 proteins was further verified by Coomassie staining of gels.

N-Terminal Protein Sequencing

A 12% polyacrylamide-SDS gel was cast and allowed to polymerize overnight to minimize amino acid-reactive free acrylamide. The gel was pre-electrophoresed at 80 V for 15 min in SDS-PAGE running buffer[11] containing 2 mM thioglycolic acid. To alkylate proteins (for detection of unmodified Cys residues), the samples were treated with 10 mM iodoacetamide (Sigma) at room temperature for 20 min in the dark, and the reaction was quenched with DTT added to the final concentration of 10 mM. The alkylated samples were heated in SDS-sample buffer[11] at 65° C. for 30 min before electrophoresis, with SDS-PAGE running buffer containing 2 mM thioglycolic acid. After electrophoresis, the gel was equilibrated in the transfer buffer (10% methanol, 10 mM CAPS (Sigma-Aldrich), pH 11) for 10 min before electroblotting onto PVDF membrane (Sequi-Blot, Bio-Rad) pre-equilibrated in the transfer buffer. Electroblotting was carried out at 100 mA overnight at 4° C. The PVDF membrane was washed with double-distilled water for 10 min, stained with Coomassie Blue R250 (0.1% R250 in 50% methanol) for 1 min, and destained in 50% methanol, 10% acetic acid. The relevant protein band was excised and analyzed by Edman degradation, using model 492 cLC protein microsequencer (ABI).

Results

Oxidation of Cysteine is Required for its Arginylation

Initial experiments were designed to determine whether the presence of CysO$_3$H (instead of Cys) at position 2 of purified, in vivo-arginylated RGS4 protein (12) reflected the requirement for oxidation of Cys prior to its arginylation, as distinguished, for example, from oxidation of Cys after its arginylation. Three otherwise identical 8-residue peptides were synthesized that bore either Asp, or Cys, or CysO$_3$H at the N-terminus. The 7-residue HGSGAWL (SEQ ID NO:3) sequence, which followed the varying N-terminal residue, was identical to the sequence at positions 2-8 of X-βgal, a β-galactosidase-based reporter substrate of the N-end rule pathway (6, 14, 16). The peptides were incubated with purified mouse ATE1-1 R-transferase (11) in the presence of ATP, S. cerevisiae tRNAs, and purified S. cerevisiae Arg-tRNA synthetase, then peptide products were analyzed either by capillary electrophoresis or mass spectrometry). At the approximately physiological pH 7.5, the Asp-peptide and the CysO$_3$H-peptide were efficiently arginylated, whereas the Cys-peptide was not arginylated, as determined by CE, and confirmed, in regard to the identities of products, by MALDI-TOF MS and by MS/MS peptide sequencing.

The side chains of N-terminal Asp and Glu, two efficacious substrates of R-transferase, are significantly ionized at pH 7.5. If arginylation by R-transferase requires an acceptor residue side chain to be an anion, this would account for both the activity of CysO$_3$H (side chain pK$_a$<2) and negligible activity of Cys (side chain pK$_a$ approx. 9.5). As such, an experiment was performed to determine whether R-transferase can arginylate the Cys-peptide at pH 9.0, which increases the fraction of Cys as a thiolate anion. CE analysis indicated that arginylation of Cys-peptide was undetectable even at pH 9.0, in contrast to arginylation of CysO$_3$H-peptide and Asp-peptide. Parallel MALDI-TOF MS analyses detected trace amounts of Arg-Cys-peptide (below the sensitivity of CE) in reactions with Cys-peptide carried out at pH 7.5 or 9.0, but the MS results were not quantitative, as compared to the CE results, in part because of large differences in the ionization/desorption efficiency among peptides of different sequences. An approximate MS-based comparison was carried out by mixing equimolar amounts of Asp-peptide, Cys-peptide and CysO$_3$H-peptide, followed by the in vitro arginylation assays at pH 9.0 and MS analysis of peptides. Under these, competition-based, conditions, Arg-Cys-peptide was no longer formed, even at levels detectable by MS, in contrast to Arg-Asp-peptide and Arg-CysO$_3$H-peptide.

The results demonstrated that N-terminal cysteine must be oxidized prior to its arginylation by R-transferase. Three 8-residue peptides with their N-terminal residues being either Asp, Cys, or CysO$_3$H, were incubated with the mouse ATE1-1 Arg-tRNA-protein transferase (R-transferase) at pH 7.5 in the presence of ATP, tRNAs, and S. cerevisiae Arg-tRNA synthetase, followed by analyses of peptide products, either by capillary electrophoresis (CE) or by MALDI-TOF mass spectrometry (MS). CE results were plotted with respect to the time of elution from CE column (x-axis) and absorbance at 200 nm (y-axis). Arginylation of each of the three peptides was examined at 0 min and after 60 min. Results were standardized by comparison to the electrophoretic position of a separately run marker, Arg-Cys-peptide and a chemically synthesized arginylated Cys-peptide. For MALDI-TOF analysis of the samples, the molecular masses of ionized [+H$^+$] derivatives were determined.

The same results were obtained when mouse ATE1-1 was replaced, in the above assays, with purified S. cerevisiae ATE1 R-transferase (33), a strong sequelog of mammalian R-transferases (11, 34). Yeast R-transferase efficiently arginylated CysO$_3$H-peptide, but not Cys-peptide. This result, together with the fact of Cys being a stabilizing residue in the yeast N-end rule (2), indicates that the bulk of N-terminal Cys in yeast is not oxidized. This result is in agreement with an earlier study that detected unmodified N-terminal Cys in a significant fraction of Cys-βgal reporter protein in yeast, with the rest of Cys-βgal molecules being unable to be sequenced by Edman degradation presumably because of N-terminal acetylation, or another blocking modification, of Cys (11).

These results demonstrate that the rate of arginylation of N-terminal Cys by mouse and yeast R-transferases is extremely low, and that Cys must be oxidized prior to its efficacious arginylation.

RGS4 and RGS16 Levels are Increased in ATE1$^{-/-}$Embryos

RGS4 is a GTPase-activating protein (GAP) for specific Gα subunits of heterotrimeric G proteins, and is a member of the family of RGS proteins that regulate G proteins (32, 35 to 37). Earlier work identified RGS4, which begins, as a nascent protein, with the sequence Met-Cys, as an arginylated substrate of the N-end rule pathway-in extracts from rabbit reticulocytes (38). Two other members of the mammalian RGS family, RGS5 and RGS16, also have an N-terminal Cys residue. RGS16 was shown to be an N-end rule substrate in a cell-free extract (38). However, in contrast to this in vitro evidence, a C-terminally tagged RGS4 transiently overexpressed in mouse L cells was moderately short-lived, but did not appear to be targeted by the N-end rule pathway (38). The levels of endogenous RGS4 could be strongly increased by proteasome inhibitors, indicating that RGS4 was targeted by the Ub-proteasome system (37). However, the specific pathway of RGS4 degradation in vivo was not previously identified.

A role of the N-end pathway in RGS4 degradation was investigated by using antibody to the untagged 23K RGS4 protein (37) and comparing the levels of endogenous RGS4 between 12.5 days old (E12.5) wild-type (+/+) mouse embryos and congenic ATE1$^{-/-}$ embryos, which lack R-transferases and, therefore, arginylation (12). ATE1$^{-/-}$ mice died as embryos throughout development, with all of them dying by E17 (12). Most ATE1$^{-/-}$ embryos appeared anatomically normal, albeit growth-retarded and under-vascularized, until about E15 (12).

Figure 6:
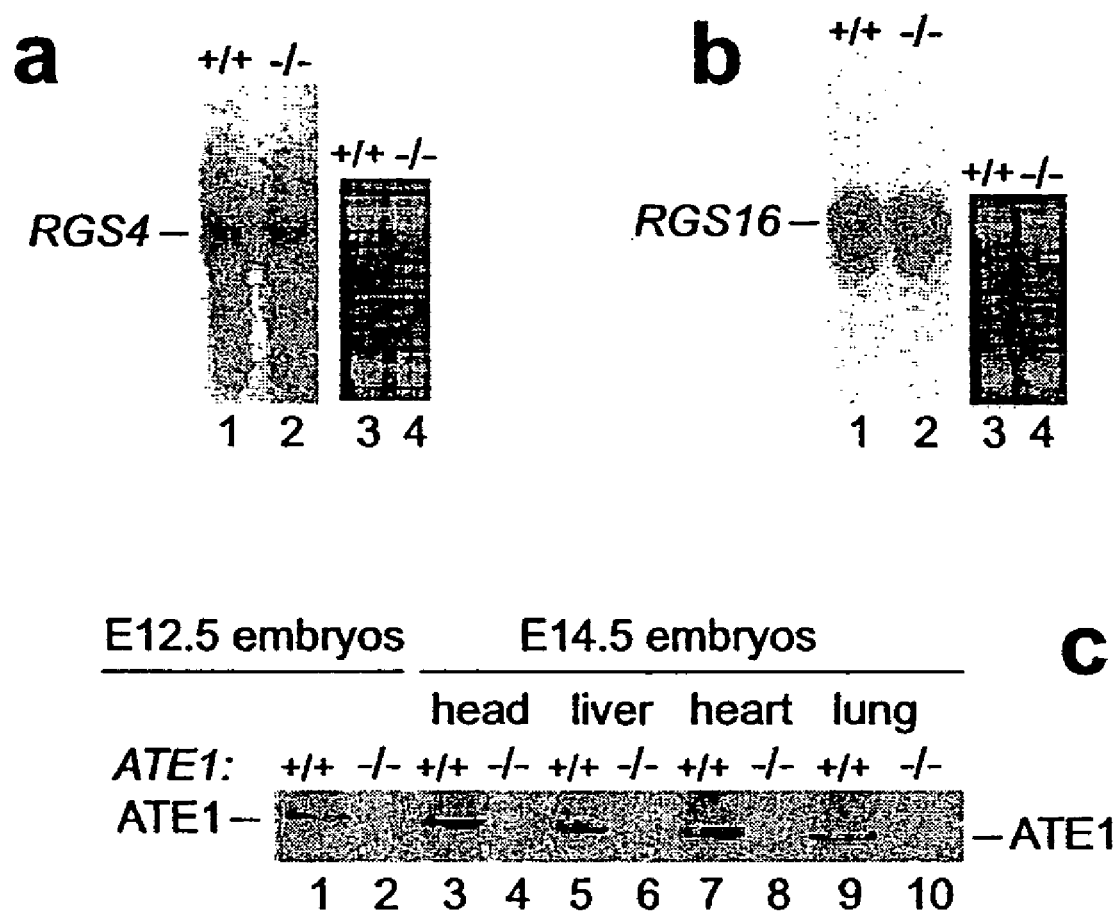
FIG. 6 shows a Northern hybridization and immunoblotting with antibody to ATE1.

We compared the levels of endogenous RGS4 between 12.5 days old (E12.5) +/+ mouse embryos and ATE1$^{-/-}$ embryos, which lacked R-transferases and therefore lacked arginylation. The level of RGS4 in E12.5 ATE1$^{-/-}$ embryos was strikingly higher than in E12.5 +/+ embryos (FIG. 2a). Similar results were obtained in pairwise comparisons of RGS4 in specific tissues from E14.5 +/+ and ATE1$^{-/-}$ embryos (FIG. 2b). Two other members of the RGS family, RGS5 and RGS16, also bear N-terminal Cys. Experiments analogous to those with RGS4 revealed strong increases of RGS5 and RGS16 in ATE1$^{-/-}$ embryos (FIG. 2c-f). These protein patterns (FIG. 2a-f) were not caused by increased levels of the corresponding mRNAs, as indicated by both cDNA microarray comparisons and Northern analyses (FIG. 6).

A more detailed comparison was carried out, using anti-RGS4 and immunoblotting with extracts from specific organs of older (E14.5) ATE1$^{-/-}$ embryos and their +/+ counterparts. The levels of RGS4 in the brains, hearts, and lungs of E14.5 ATE1$^{-/-}$ embryos were much higher than RGS4 levels in the same organs of E14.5 +/+ embryos. RGS4 levels were highest in the brain and lung of ATE1$^{-/-}$ embryos, intermediate in the heart, and lowest in the liver, where traces of RGS4 could be detected in the absence of ATE1, but not in its presence.

Analogous experiments were carried out with RGS16, another of the three mammalian RGS proteins (35, 36) that bear N-terminal Cys after the (cotranslational) removal of N-terminal Met. Using antibody to the untagged 23 kDa RGS16 (apparent M$_r$ approx. 25 kDa), a striking increase of RGS16 levels was observed in the absence of R-transferases. RGS16 could not be detected in E12.5 +/+ embryos (similarly to RGS4), but was readily detectable in littermate ATE1$^{-/-}$ embryos. Analyses of RGS16 in specific organs of El 4.5 ATE1$^{-/-}$ embryos versus +/+ embryos yielded results similar to those with RGS4, in that the levels of RGS16 were much higher in organs from ATE1$^{-/-}$ embryos, with strongest increases in the brain and lung. RGS16 was undetectable in +/+ hearts but readily detectable in ATE1$^{-/-}$ hearts. RGS16 could not be detected in either +/+ or ATE1$^{-/-}$ livers. Immunoblotting of the same samples with antibody to mouse ATE1 (R-transferase) confirmed the absence of ATE1 (59 kDa) from ATE1$^{-/-}$ embryos and their organs.

Extensive cDNA microarray-based comparisons of RNA isolated from +/+ and ATE1$^{-/-}$ embryos indicated that the relative levels of either RGS4 or RGS16 mRNAs were virtually the same between the two genotypes. Thus, the strongly elevated concentrations of the RGS4 and RGS16 proteins in ATE1$^{-/-}$ embryos were not caused by increased levels of the corresponding mRNAs in the absence of ATE1.

To address the above questions differently, the relative level of RGS16 in mouse cells that were near-null in the N-end rule pathway was determined. These cells, termed (UBR1$^{-/-}$UBR2$^{-/-}$)$^{PCMV-UBR2(1041)}$, were derived from a double-mutant (UBR1$^{-/-}$UBR2$^{-/-}$) embryonic fibroblast (EF) cell line that lacked two E3 Ub ligases of the N-end rule pathway. In contrast to S. cerevisiae, where this pathway is mediated by a single Ub ligase (2), UBR1, the mouse and human genomes encode, in addition to the highly similar UBR1 and UBR2 proteins (FIG. 1a; see, also, Refs. 4, 15), at least two other distinct N-recognins (i.e., Ub ligases that can recognize (bind to) destabilizing N-terminal residues in proteins and short peptides).

(UBR1$^{-/-}$UBR2$^{-/-}$) embryos (produced through compound heterozygous matings of single-mutant UBR1$^{-/-}$ and UBR2$^{-/-}$ mice; see Refs. 4, 15) died, with multiple defects, before E12. A double-mutant (UBR1$^{-/-}$UBR2$^{-/-}$) EF cell line, established from (UBR1$^{-/-}$UBR2$^{-/-}$) embryos, retained the N-end rule pathway, of reduced activity (Ref. 4), as would be expected given the multiplicity of mammalian N-recognins. A derivative of the (UBR1$^{-/-}$UBR2$^{-/-}$) EF cell line was constructed that stably expressed, from the P$_{CMV}$ promoter, an epitope-tagged N-terminal fragment, termed UBR2$^{1041}$, of the 200K mouse UBR2. Similarly to the previously described N-terminal half of the yeast UBR1 Ub ligase (13), the mouse UBR2$^{1041}$ fragment, which contained substrate-binding sites but was inactive as a Ub ligase, functioned as a dominant-negative inhibitor of the (residual) N-end rule pathway in (UBR1$^{-/-}$UBR2$^{-/-}$) cells, as determined with reporter N-end rule substrates. The resulting (UBR1$^{-/-}$UBR2$^{-/-}$)$^{PCMV-UBR2}$ (1041) cell line came closest, thus far, to a complete null of the N-end rule pathway in mammalian cells.

The levels of endogenous RGS16 were compared among +/+ EF cells, (UBR1$^{-/-}$UBR2$^{-/-}$) cells, and (UBR1$^{-/-}$UBR2$^{-/-}$)$^{PCMV-UBR2(1041)}$ cells. The level of RGS16 was negligible in +/+ cells, barely detectable in (UBR1$^{-/-}$UBR2$^{-/-}$) cells, and strikingly higher in (UBR1$^{-/-}$UBR2$^{-/-}$)$^{PCMV-UBR2}$ (1041) cells. This result confirmed, in a setting different from that of ATE1$^{-/-}$ cells, that RGS16 is an in vivo substrate of the N-end rule pathway.

Decreasing Nitric Oxide In Vivo Stabilizes RGS4 and RGS16

To examine the possibility that oxidation of N-terminal Cys might involve NO, we constructed a mouse cell line, termed 3T3$^{toff}$RGS4$_{fh}$, that expressed RGS4-flag-His$_6$ (RGS4$_{fh}$) from a doxycycline-repressible promoter. Treatment of 3T3$^{toff}$RGS4$_{fh}$ cells with LMMA, an inhibitor of NO synthases (NOSs), dramatically increased the in vivo level of RGS4 (FIG. 3a, lanes 2 vs. 4). When CPTIO, a cell-penetrating NO scavenger, was employed to reduce NO, the increase in RGS4 was even more striking (FIG. 3a, lanes 2 vs. 3, and lanes 7 vs. 8).

Figure 7:
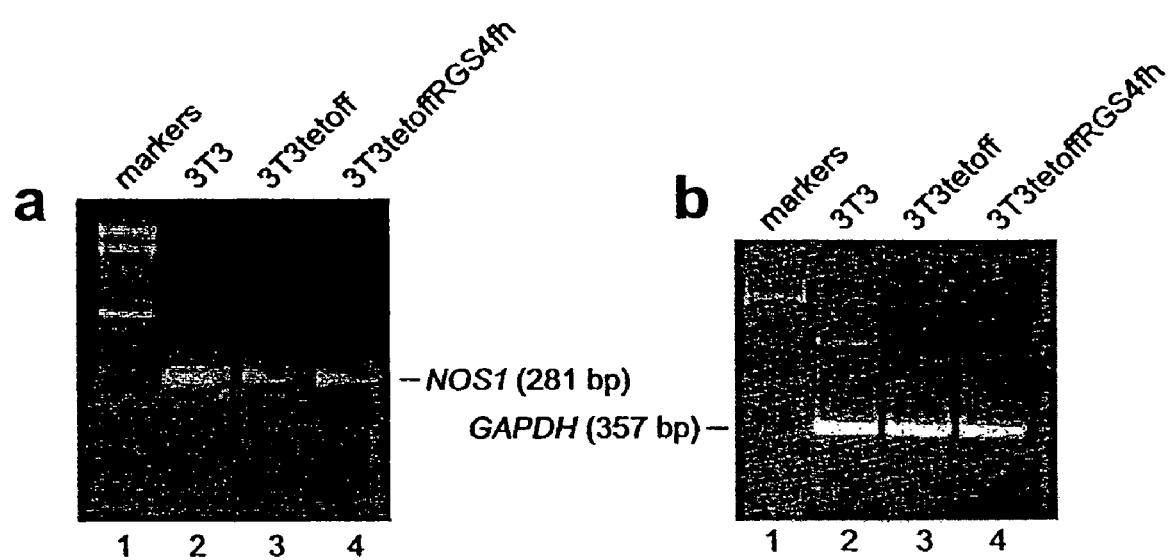
FIG. 7 shows RT-PCR of mRNAs encoding NO synthases.
Figure 8:
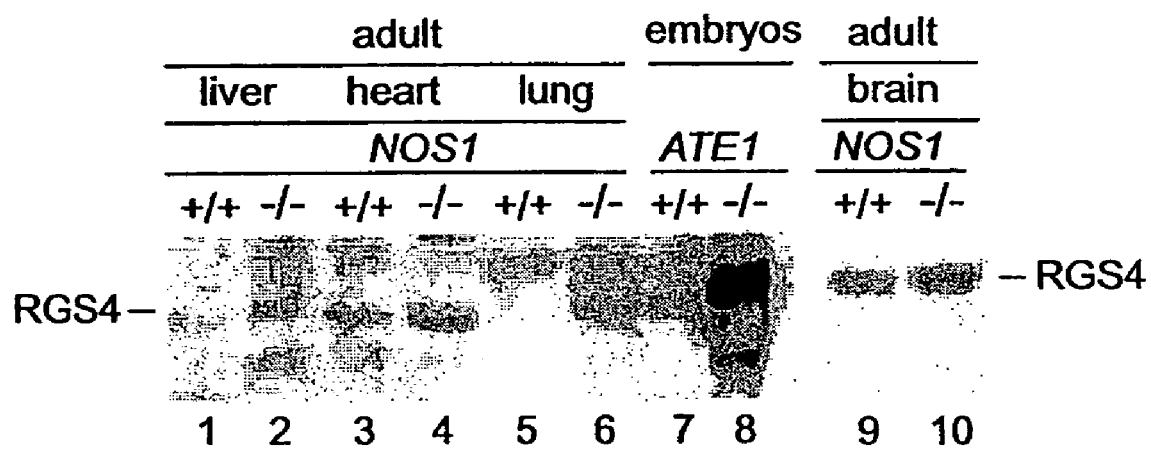
FIG. 8 shows the levels of RGS4 in NOS1$^{-/-}$ mice. Lanes 1-6, 9, 10, pairwise comparisons of the levels of RGS4 in organs of 7 months old +/+ mice and littermate NOS1$^{-/-}$ mice, which lack one of three NO synthases. Note a particularly significant difference in the lung (lane 5 vs. 6). Lanes 7, 8, the same immunoblotting analysis, but with +/+ and ATE1$^{-/-}$ E12.5 embryos.

RT-PCR showed that 3T3$^{toff}$RGS4$_{fh}$ cells expressed NOS1 (nNOS) mRNA but little if any NOS2 (iNOS) and NOS3 (eNOS) mRNAs (FIG. 7). Given these findings, we also used an NOS inhibitor (N3411) that is highly selective for NOS1 (nNOS). In agreement with other NO results (FIG. 3a, lanes 1-8), and despite the near-confinement of inhibition by N3411 to NOS 1, this inhibitor substantially increased the levels of RGS4 (FIG. 3a, lanes 9-11). We also asked whether RGS4 was elevated in NOS1$^{-/-}$ adult mice[24]. Despite the presence of NOS2 and NOS3 in these mice, RGS4 was strongly increased in the NOS1$^{-/-}$ lung, relative to +/+ lung, and to a lesser extent in other tissues as well (FIG. 8).

Nitric oxide (NO), which is known to react with specific internal Cys residues in proteins to form S-nitrosothiols that can undergo further chemical transformations to yield an oxidized Cys residue (e.g., CysO$_2$H or CysO$_3$H; see Refs. 21, 23, 25, 30), was examined to determine whether it was the source of the oxidation of N-terminal Cys that was required for arginylation by R-transferase. To address the possibility that degradation of N-end rule substrates bearing N-terminal Cys requires NO, a mouse cell line, termed 3T3$^{toff}$RGS4$_{fh}$, which expressed C-terminally tagged RGS4-flag-His$_6$ (RGS4$_{fh}$) from a doxycycline-repressible promoter, was constructed. After inducing the expression of RGS4$_{in}$ 3T3$^{toff}$RGS4$_{fh}$ cells by withdrawal of doxycycline, cultures either were left untreated or were treated for 24 hr with LMMA, a competitive inhibitor of NO synthases, followed by SDS-PAGE of extracted proteins and IB using an anti-RGS4 antibody.

Control (untreated) 3T3$^{toff}$RGS4$_{fh}$ cells expressing RGS4$_{fh}$ contained RGS4 at a detectable, but low, steady-state level. Treatment of these cells with LMMA dramatically increased the level of RGS4. Moreover, when endogenous NO was reduced through the use of CPTIO, a cell-penetrating NO scavenger, the increase in RGS4 was even greater than with LMMA. These results were reproducible in independent experiments. In one experiment, anti-RGS4 antibody detected two RGS4 bands, including an upper band at the position expected for a protein the size of RGS4$_{fh}$, and a lower band, which appeared to be a proteolytic fragment of RGS4$_{fh}$ because changes in its levels paralleled those of the full length RGS4$_{fh}$; the lower band was not observed in an otherwise identical independent experiment. In agreement with this interpretation, the anti-RGS4 antibody detected one RGS4 band in ATE1$^{-/-}$ embryos, but did not detect RGS4 in parental 3T3$^{toff}$ cells, which lack the RGS4$_{fh}$-expression cassette, either before or after treatment with CPTIO.

To further address the effect of NO on the levels of RGS4 in 3T3$^{toff}$RGS4$_{fh}$ cells, the ability of the NO scavenger CPTIO to alter the extent of arginylation of RGS4$_{fh}$ in 3T3$^{toff}$RGS4$_{fh}$ cells was examined by N-terminal sequencing of purified RGS4$_{fh}$. In these experiments, the in vivo destruction of RGS4$_{fh}$ by the N-end rule pathway was reduced by the proteasome inhibitor MG132. Edman sequencing of RGS4$_{fh}$ from control 3T3$^{toff}$RGS4$_{fh}$ cells showed it to be completely or nearly completely (>90%) arginylated in vivo. In contrast, the bulk of RGS4$_{fh}$ isolated from 3T3$^{toff}$RGS4$_{fh}$ cells that had been treated with CPTIO was unable to be sequenced by Edman degradation, suggesting that a blocking modification (e.g., acetylation, or palmitoylation) of N-terminal Cys in RGS4$_{fh}$ occurs in CPTIO-treated cells. Thus, RGS4$_{fh}$ from cells containing low amounts of NO was largely unarginylated and, therefore, not a target of the N-end rule pathway. This result is in agreement with the greatly increased levels of RGS4$_{fh}$ observed in cells treated with LMMA or CPTIO.

To verify that strong increases in the levels of RGS4 upon depletion of NO in 3T3$^{toff}$RGS4$_{fh}$ cells were caused at least in part by metabolic stabilization of RGS4, pulse-chase assays were performed using $^{35}$S-methionine/cysteine and antibody to RGS4, with control (doxycycline-off, untreated) 3T3$^{toff}$RGS4$_{fh}$ cells expressing RGS4$_{fh}$, and with otherwise identical cultures after treatment with NO scavenger CPTIO. The band of pulse-labeled RGS4$_{fh}$ from untreated 3T3$^{toff}$RGS4$_{fh}$ cells could be detected at the end of 10-min pulse only upon autoradiographic overexposure, and not at all during chase, indicating rapid degradation of RGS4$_{fh}$ during the pulse. In contrast, a strongly labeled band of RGS4$_{fh}$ was observed consistently, in independent experiments, with CPTIO-treated 3T3$^{toff}$RGS4$_{fh}$ cells at the end of 10-min pulse. While clearly stabilized in CPTIO-treated 3T3$^{toff}$RGS4$_{fh}$ relative to untreated cells, RGS4$_{fh}$ remained partially unstable even in the presence of CPTIO, in agreement with incomplete elimination of NO by CPTIO (see, also, Refs. 23 and 29, and references cited therein).

The degradation kinetics of pulse-labeled RGS4$_{fh}$ in CPTIO-treated cells revealed a significant decrease of RGS4$_{fh}$, 1 hr after the pulse, but little degradation over the next hour, indicating that newly formed RGS4$_{fh}$ molecules were degraded by the N-end rule pathway faster than their older counterparts. As described above, RGS4$_{fh}$ was barely detectable in untreated, control cells at the end of a 10 min pulse, and undetectable afterwards. Stabilization of RGS4$_{fh}$, that was caused by depletion of NO was confined to Cys-bearing substrates of the N-end rule pathway. Specifically, the degradation of Asp-nsP4, a short-lived reporter protein derived from Sindbis virus RNA polymerase and bearing N-terminal Asp (its targeting requires arginylation but not oxidation, see, also, Ref. 12) did not change between untreated and CPTIO-treated cells. In agreement with the IB data no RGS4 could be detected at the end of 10-min pulse in parental 3T3$^{toff}$ cells, which lack the RGS4$_{fh}$ expression cassette, either before or after treatment with CPTIO.

To address the above issues differently, advantage was taken of the fact that endogenous RGS16, but not RGS4, was expressed in NIH-3T3 cells and in EF cell lines derived from +/+ and ATE1$^{-/-}$ embryos. Anti-RGS16 antibody detected trace amounts of RGS16 in untreated 3T3 cells, whereas a strikingly higher level of RGS16 was observed when 3T3 cells were treated with NO scavenger CPTIO. This strong dependence of the level of RGS16 on the level of endogenous NO was nearly absent when the same experiment was carried out with ATE1$^{-/-}$ EF cells (12), which lack arginylation.

CPTIO treatment of ATE1$^{-/-}$ cells resulted in little or no increase of the RGS16 level, which was high even in the absence of CPTIO. These findings confirm, in a setting different from both pulse-chase and RGS4$_{fh}$-expressing 3T3$^{tof}$RGS4$_{fh}$ cells, that the degradation of RGS16 by the N-end rule pathway requires both NO and arginylation.

These results demonstrate that oxidation of the N-terminal Cys in RGS4 and RGS16 is mediated by NO in vivo. Although no mechanism for the oxidation is proposed, NO can act through S-nitrosylation of the uniquely located Cys residue to yield CysO$_2$H or CysO$_3$H (23, 25, 26), thereby converting the N-terminal Cys to a substrate for arginylation by an ATE1-encoded R-transferase. These results further identify the arginylation branch of the N-end rule pathway as a sensor of NO, and provide a basis to understand previously unexplained observations. For example, a mutation that converted the position-3 residue (position 2 after Met removal) of RGS4 from positively charged Lys to uncharged Ser completely stabilized the resulting RGS4K3S variant against degradation by the N-end rule pathway in reticulocyte extract, despite the retention of N-terminal Cys in RGS4K$_3$s, whereas the RGS$^4$K3R variant, in which Lys that normally follows N-terminal Cys was replaced by Arg (rather than Ser), continued to be degraded by the extract's N-end rule pathway (38). Furthermore, in contrast to wild-type RGS4, which was arginylated and bore CysO$_3$H at position 2 (see, also, Ref. 12), the RGS4K3S variant that was transiently overexpressed in L cells was found to have a blocked N-terminus upon purification and N-terminal sequencing. These results can now be accounted for because S-nitrosylation of Cys residues by NO in proteins or short peptides is known to depend on the identity of residues in the vicinity of Cys (23, 25, 30). In particular, a Cys-proximal basic residue, which facilitates the abstraction of H$^+$ from the thiol group of Cys, is expected to accelerate S-nitrosylation of Cys by NO. Thus, either Lys, Arg or His at position 2, but not Ser, would be expected to increase the reactivity of N-terminal Cys toward NO, thereby making possible the oxidation and subsequent arginylation of N-terminal Cys in RGS4.

In agreement with this explanation, the N-terminal sequence of RGS16, another arginylation-dependent in vivo N-end rule substrate, is Cys-Arg. To address this issue further, antibody to serine racemase (SRR; Ref. 22), a protein with the N-terminal sequence Cys-Ala, was used to determine whether the levels of racemase were increased in either ATE1$^{-/-}$ embryos, lacking the arginylation branch of the N-end rule pathway, or in (UBR1$^{-/-}$ UBR2$^{-/-}$)$^{PCMV-UBR2(1041)}$ cells, which were a near-null of this pathway (see above). In contrast to the findings with RGS4 and RGS16, no significant changes in the level of the racemase were observed, as would be expected from the requirement for a basic residue at position 2 for the efficacious NO-mediated oxidation of N-terminal Cys.

The present results demonstrate that oxidation of N-terminal Cys is essential for its arginylation. More specifically, the in vivo oxidation (and subsequent arginylation) of a protein's N-terminal Cys residue requires NO, and further prefers the presence of a basic amino acid residue at position 2. The levels of regulatory proteins with this Cys-(basic residue) N-terminal motif (e.g., RGS4 and RGS16) were strikingly increased in mouse ATE1$^{-/-}$ embryos lacking arginylation. Given the roles of RGS4 and RGS16 in cardiovascular homeostasis (32), this stabilization-mediated increase can be a contributing factor in the abnormal angiogenesis and heart development (12) observed in ATE1$^{-/-}$ embryos. A typical mammalian genome encodes approximately 200 proteins that are expressed as nascent polypeptides with N-terminal Met-Cys, and about 30 of these proteins, including RGS4, RGS5 and RGS16, contain the Met-Cys-(basic residue) N-terminal motif, which, as disclosed herein, provides a consensus sequence for the NO-dependent, arginylation-mediated, Cys-specific N-degron. Together, the present results identify the arginylation branch of the N-end rule pathway as a sensor of NO in mammalian cells that functions through its ability to destroy specific regulatory proteins bearing N-terminal Cys, at the rates controlled by NO, and possibly by oxygen as well (FIG. 1).

NO-Dependent Arginylation of RGS4 In Vitro

Figure 3:
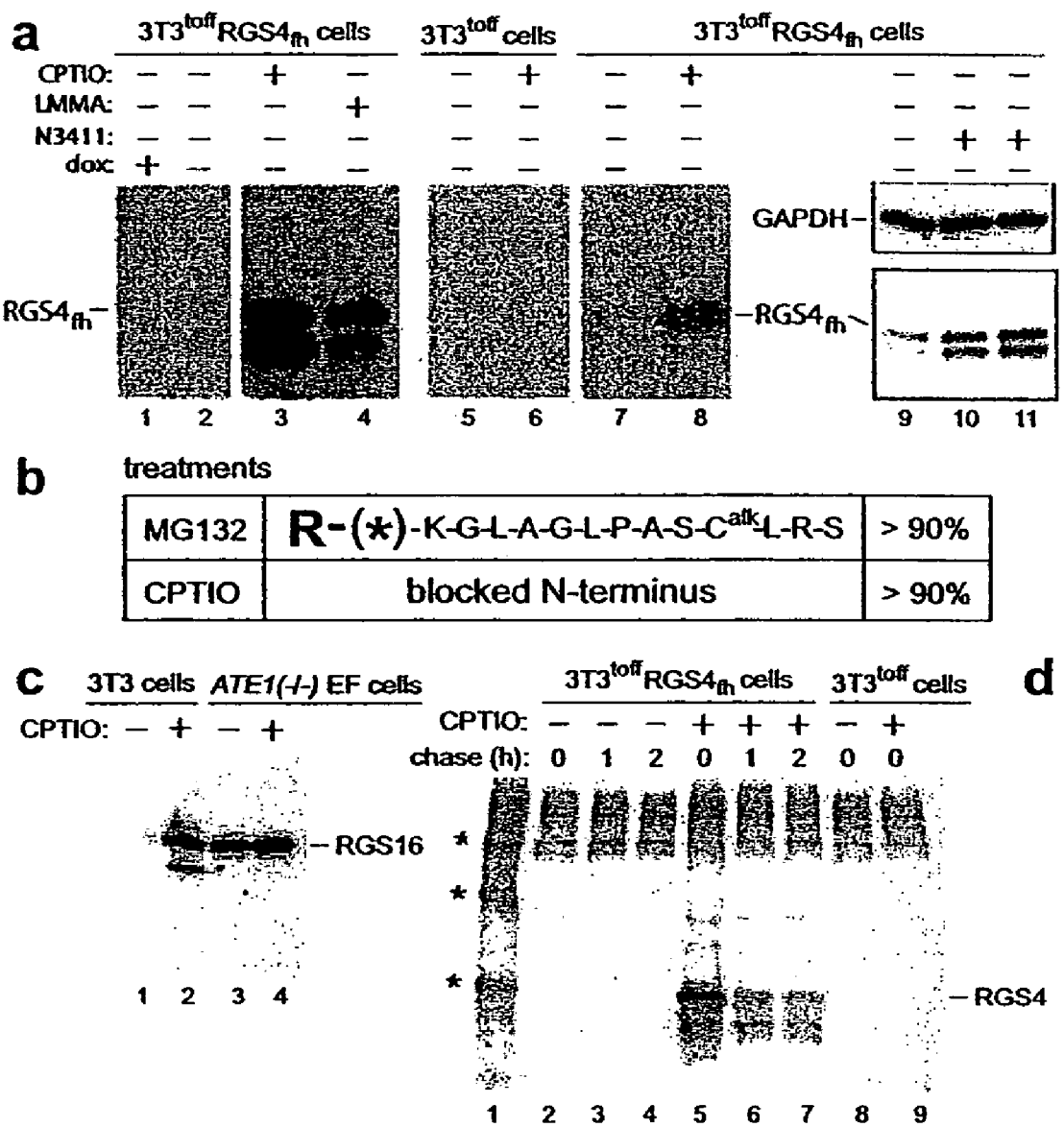
Figure 4:
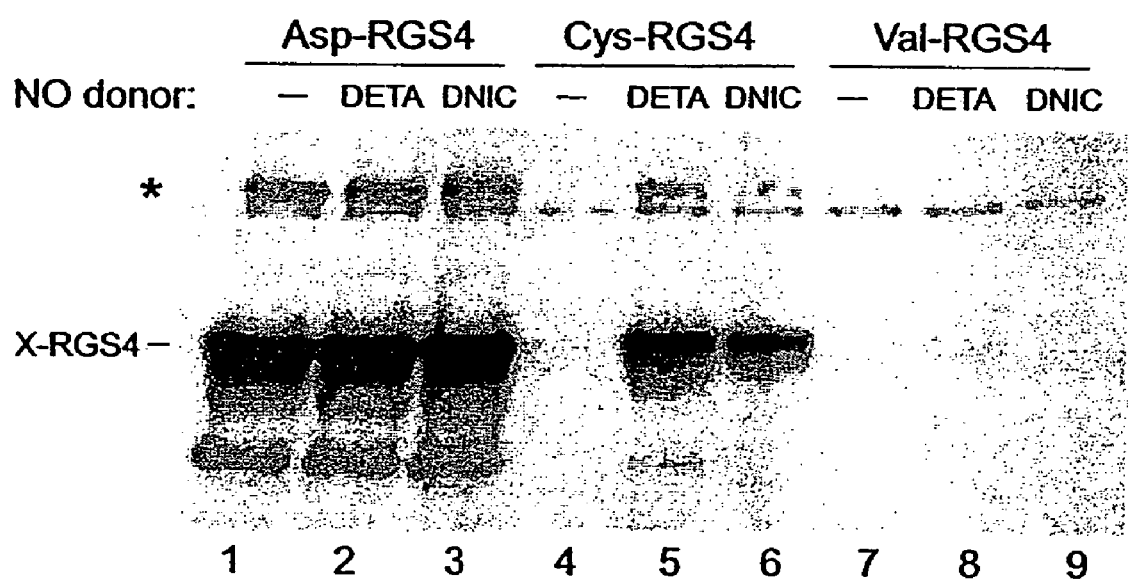
FIG. 4 shows an SDS-PAGE illustrating in vitro reconstitution of nitric oxide-dependent arginylation of RGS4. Purified Asp-RGS4 (lanes 1-3), Cys-RGS4 (lanes 4-6) and Val-RGS4 (lanes 7-9) were incubated with $^3$H-arginine under conditions of the arginylation assay (see the main text), followed by SDS-PAGE and fluorography. Lanes 1, 4, 7, no pretreatment of X-RGS4s. Lanes 2, 5, 8, pretreatment of X-RGS4s with DETA-NO. Lanes 3, 6, 9, pretreatment of X-RGS4s with DNIC-[GSH]$_2$. Asterisk denotes a minor $^3$H-labeled species whose apparent $M_r$ and relative levels suggest that it is a dimer of X-RGS4.
Figure 5:
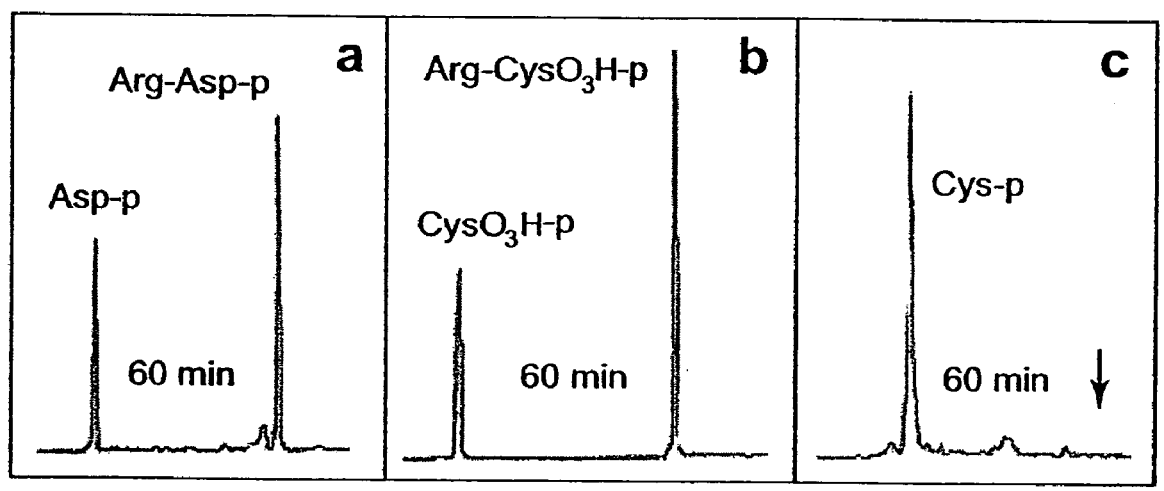
FIG. 5 shows N-terminal cysteine must be oxidized prior to its arginylation by S. cerevisiae R-transferase. Three 8-residue peptides, denoted as X-p, with their N-terminal residues (X) being either Asp, Cys, or CysO$_3$H, were incubated for 60 min with purified S. cerevisiae ATE1-1 R-transferase at pH 7.5 in the presence of ATP, S. cerevisiae Arg-tRNA synthetase, and tRNAs, followed by analyses of peptide products by capillary electrophoresis (CE). The x- and y-axes in CE patterns correspond, respectively, to the time of elution from CE column and absorbance at 200 nm (see also FIG. 1 and the main text).

Cys-RGS4, as well as otherwise identical Asp-RGS4 and Val-RGS4 (FIG. 1a), were produced in E. coli using the Ub fusion technique[2]. X-RGS4s were incubated with mouse ATE1-1 R-transferase in the presence of ATP, $^3$H-arginine, tRNA and other components of the analogous assay with 8-residue peptides (FIG. 1c-j), except that arginylation of X-RGS4 was detected by SDS-PAGE and fluorography. In addition to untreated controls, X-RGS4s were also preincubated with one of two NO donors, either diglutathionyl-dinitroso-iron (DNIC-[GSH]$_2$, a physiologically relevant NO carrier) or DETA-NO. The results indicated a virtually complete dependence of the in vitro arginylation of Cys-RGS4 on its prior exposure to a donor of NO (FIG. 4, lanes 4 vs. 5 and 6). (Dissolved oxygen and other gases were at levels that are normally present in buffers.) In contrast, Asp-RGS4 was efficiently arginylated irrespective of NO pretreatment, and Val-RGS4 was not arginylated (FIG. 4). Thus, the NO dependence of in vivo arginylation of proteins bearing N-terminal Cys (FIGS. 2 and 3) can be reconstituted in an in vitro system (FIG. 4).

Sequence Motif of NO-Dependent N-Degron

The above examples and FIGS. 1-4 accounted for the following, previously unexplained, observation: the conversion of position-3 residue of RGS4 (position 2 after Met removal) from basic Lys to uncharged Ser stabilized the resulting RGS4K3S against degradation in reticulocyte extract. In contrast, RGS4K3R, in which Lys-2 was replaced by Arg, remained short-lived. Moreover, in contrast to wild-type RGS4, which was arginylated and bore CysO$_3$H at position 2 (FIG. 3d), RGS4K3s that was transiently expressed in mouse cells was found to have a blocked N-terminus. These results can now be explained, because S-nitrosylation of internal (non-N-terminal) Cys by NO in polypeptides depends, in particular, on the presence of a Cys-proximal basic residue, which facilitates the abstraction of H+from the cysteine's thiol group[21,22]. In agreement with this explanation, the second residues of MetAP-processed RGS4, RGS5 and RGS16 are Lys, Lys and Arg, respectively. In a different examination of the consensus motif (N-terminal Cys-[basic residue]), we used an antibody to serine racemase (SRR)[20], a protein with Cys-Ala N-terminal sequence, to ask whether the levels of racemase were increased in ATE1$^{-/-}$ embryos or UBR1/2$^{dnR2}$ cells. In contrast to results with RGS4, RGS5 and RGS16, no significant changes in racemase levels were observed (FIG. 2h, lanes 4-8).

EXAMPLE 2

Generation of ATE1+/31 and ATE1$^{-/-}$ Mice

This example describes the generation of the mice lacking the ATE1 activity. These mice served as a model for the activity of an inhibitor of ATE1 activity (either an enzymatic inhibitor, or an inhibitor which lowers the level of expression of the ATE1 gene, for example, antisense oligonucleotides directed to the ATE1 mRNA).

Mouse ATE1 was isolated using screening, with an ATE1 cDNA fragment (nucleotides 638-1,491), of a BAC library (Genome Systems) from 129/SvJ ES mouse cells (see, also, U.S. Publ. No. 2004-0009538-A1, which is incorporated herein by reference; see FIG. 1B of U.S. Publ. No. 2004-0009538-A1). The exon/intron organization of the first ~20 kb of ATE1 was determined using exon-specific PCR primers to produce genomic DNA fragments flanked by exons. The targeting vector was linearized with HindIII and electroporated into CJ7 embryonic stem (ES) cells, followed by selection and identification of the correctly targeted $ATE_1^{+/-}$ ES cell clones with normal karyotype. Standard techniques were then used to produce chimeric and $ATE1^{-/-}$ mice. Phenotypes of $ATE1^{-/-}$ embryos were observed mainly with mice of the C57BL/6J-129SvEv (mixed) background, and confirmed in the 129SvEv (inbred) background. RT-PCR, Southern and northern blot analyses, and PCR-mediated genotyping of embryos and pups were performed.

Heterozygous ($ATE1^{+/-}$) mice were viable and apparently normal. Intercrosses of $ATE1^{+/-}$ mice yielded the expected frequencies of +/+ and $ATE1^{+/-}$ pups, but no $ATE1^{-/-}$ mice were recovered amongst either 954 $F_2$-generation pups of the C57BL/6J-129SvEv (mixed) background or 267 $F_2$-generation pups of the 129SvEv (inbred) background. Timed intercrosses of $ATE1^{+/-}$ mice were used to determine that $ATE1^{-/-}$ embryos were present at approximately the expected (25%) frequency up to ~E13.5, but virtually no $ATE1^{-/-}$ embryos were recovered alive by E17. Until E12.5, $ATE1^{-/-}$ embryos appeared to be morphologically normal; however, their growth stopped during E13.5-E15.5. By E14.5-E15.5, ~50% of $ATE1^{-/-}$ embryos were still alive, but growth-retarded. Live E14.5-E15.5 embryos were capable of opening their mouths and flexing their bodies, suggesting the absence of gross neuromuscular defects. Sections through E13.5 $ATE1^{-/-}$ embryos indicated the presence and apparently normal appearance of major organs, except for the phenotypes described below in Example 4.

EXAMPLE 3

Expression of $ATE1^-$ Allele

The $ATE1^-$ allele was marked with NLS-β-galactosidase (hereafter βgal), expressed from the ATE1 promoter. During E9.5-E12.5, the expression of ATE1 (βgal) was high in the neural tube, including the floor plate, motor neurons, and the neural fold. ATE1 was also expressed in dorsal root ganglia, sympathetic ganglia and notochord, and in neurons that regulate blood vessels; the latter examples included sympathetic trunks between midline dorsal aorta and subcardinal vein, and a ganglion near the primary head vein. ATE1 was also expressed in sharply delineated subsets of myotomal cells in each somite, in the mesonephric vesicles (kidney precursor), in the gut, in specific areas of the eye primordium, at the tips of limb buds, in the endodermal layer of the yolk sac (but not in its mesodermal layer), and in specific areas of embryonic heart, including trabeculae, endocardial cushion, aortic valve, and aorta.

EXAMPLE 4

Angiogenic Defects of $ATE1^{-/-}$ Mice $ATE1^{-/-}$ embryos (and yolk sacs) were pale in comparison to their +/+ and $ATE1^{+/-}$ littermates, had thinner blood vessels and frequent edemas of the skin, with extensive apoptosis of cells in edematous regions. About 40% of live E15.5 $ATE1^{-/-}$ embryos looked nearly normal, except for a significant growth retardation, thinner peripheral vessels and thinner vitelline vessels. The rest (~60%) of live E15.5 $ATE1^{-/-}$ embryos exhibited at least one of the following phenotypes: local hemorrhages, edemas, and abdominal ruptures. Hemorrhages, often massive, at various locations, predominantly in the abdominal cavity and the head, were a consistent feature of $ATE1^{-/-}$ embryos, and the likely proximal cause of their death by E15-E17. Transverse sections of hematoxylin/eosin-stained +/+ and $ATE1^{-/-}$ hearts of E14.5 embryos showed numerous defects. Amongst 13 $ATE1^{-/-}$ hearts (E13.5-E15.5) examined, ~85% had a ventricular septal defect (VSD). The atria of many $ATE1^{-/-}$ hearts were abnormally thin-walled, with sparse trabeculae and a large atrial septal defect (ASD). The right atria of $ATE1^{-/-}$ hearts were often enlarged, resulting in twisted ventricles. Amongst 22 $ATE1^{-/-}$ hearts examined (13 extensively and 9 less so), ~90% exhibited hypoplasia of both right and left ventricular myocardium, resembling thin myocardium syndrome. The compact zone (CZ) of left ventricular myocardium was typically 2-3 cells thick, in comparison to 7-10 cells in the myocardium of +/+ littermates. Furthermore, whereas the aorta and pulmonary artery were completely separated by E13.5 in +/+ hearts, ~70% of the examined $ATE1^{-/-}$ hearts (E13.5-E15.5) had persistent truncus arteriosus (PTA), with the common root of aorta and pulmonary artery straddling a large VSD. Formation of the two ventricular chambers involves proliferation and maturation of myocytes in the compact muscular layer, accompanied by trabeculation inside the chamber. The septum is formed through condensation of trabeculae at the interventricular groove, with the medial walls of expanding ventricles fusing together, growing inward, and forming the muscular portion of septum. The above defects of $ATE1^{-/-}$ hearts suggest that the loss of R-transferase activity inhibits proliferation of myocardial cells. In addition, the PTA defect occurs when too few of the neural crest-derived cells populate the cardiac outflow tract, resulting in a failure to separate the common truncal outflow vessel into the aorta and pulmonary artery. Since ATE1 is highly expressed in structures produced by cells originating in the neural crest, the PTA defect of $ATE1^{-/-}$ hearts suggests that the R-transferase activity is also required for migration and/or differentiation of neural crest-derived myocardial cells.

Vasculogenesis, the de novo formation of blood vessels that yields the primary capillary plexus at early stages of embryogenesis, was apparently normal in E9.5 $ATE1^{-/-}$ embryos, as assayed by staining endothelial cells with anti-PECAM antibody. Standard procedures were used for thin sectioning and staining with hematoxylin/eosin, X-Gal, or anti-PECAM-1 antibody (clone MEC 13.3, Pharmingen). In contrast, the process of subsequent angiogenic remodeling that produces a hierarchic network of mature capillaries and larger vessels, was perturbed in the absence of ATE1, as could be seen, for example, in the vasculature of E13.5 +/+ versus $ATE1^{-/-}$ yolk sacs. The vessels in $ATE1^{-/-}$ sacs often terminated prematurely, and many small vessels remained as a honeycomb-like meshwork of the primary-plexus capillaries, without angiogenic remodeling. The large collecting vessels of $ATE1^{-/-}$ yolk sacs were consistently smaller than their +/+ counterparts, and $ATE1^{-/-}$ microvilli were poorly developed. In addition, the angiogenesis-produced network of blood vessels that normally cross the dorsal midline and that normally sprout from intersegmental artery was suppressed in E9.5 $ATE1^{-/-}$ embryos. An example of impaired angiogenesis in older $ATE1^{-/-}$ embryos was the head's dorsal area at E13.5.

This area was a major site of hemorrhages in ATE$^{-/-}$ embryos. Amongst 13 extensively examined ATE1$^{-/-}$ embryos, only one appeared to have a normal heart; yet, similarly to other ATE-1-$^4$ embryos, it exhibited angiogenesis defects in the yolk sac, suggesting that abnormal angiogenic remodeling was not caused by the cardiogenic defects of ATE1$^{-/-}$ embryos. A rigorous deconvolution of causes and effects in this complex setting will require the understanding of molecular circuits involved.

Increased apoptosis, detected using the TUNEL assay, was found in the edematous area of E13.5 ATE1$^{-/-}$ embryo. The TUNEL assay was performed using a kit (Roche) and fluorescein-dUTP.

This example illustrates the importance of the ATE1 gene to the process of angiogenesis. The evidence that mice lacking the ATE1 gene shows that inhibitors of ATE1 can impact angiogenesis in an animal.

EXAMPLE 5

Arginyl Transferase Reactions

For R-transferase assays, Ub-X-βgal proteins were purified from *E. coli* carrying pKKUbXβgal plasmids. The R-transferase reaction (50 ml) contained S105 supernatant (0.5 mg of protein per ml) from either EF cells or whole embryos, prepared as described (30), Ub-X-βgal or α-lactalbumin (0.2 mg/ml), *E. coli* tRNA (1 mg/ml), *E. coli* aminoacyl-tRNA synthetases (50 mg/ml), puromycin (0.2 mM), bestatin (0.15 mM), 5 mM MG132 (proteasome inhibitor), 0.4 mM Lys-Ala dipeptide (inhibitor of post-arginylation steps in the N-end rule pathway), 1 mM ATP, 10 mM creatine phosphate, 0.1 M KCl, 5 mM MgCl$_2$, 50 mM β-mercaptoethanol, 50 mM Tris-HCl (pH 8.0) and 0.3 mM $^3$H-arginine (New England Nuclear). The reaction mixture was incubated for 3 hr (2 hr with embryo extracts) at 37° C. A 20 ml sample was precipitated with 10% TCA, and analyzed by SDS-12% PAGE and fluorography.

To measure the N-terminal arginylation directly, either purified Ub-X-βgal proteins (X=Met, Arg, Glu, Cys) or purified human α-lactalbumin (bearing N-terminal Glu) were added to +/+ and ATE1$^{-/-}$ EF cell extracts supplemented with ATP, total *E. coli* tRNA and a mixture of *E. coli* aminoacyl-tRNA synthetases. SDS-PAGE and fluorography were used to detect covalent conjugation of $^3$H-Arg to test proteins in these extracts. Ub-X-βgals are rapidly deubiquitylated in vivo and in cell-free extracts, yielding X-βgal test proteins. As expected, Asp-βgal, Glu-βgal and α-lactalbumin were arginylated in the extracts from +/+ EF cells, whereas Arg-βgal and Met-βgal, bearing a primary destabilizing and a stabilizing N-terminal residue, respectively, were not arginylated. No arginylation of Asp-βgal, Glu-βgal and α-lactalbumin could be detected in ATE1$^{-/-}$ EF extracts, even after prolonged fluorographic exposures (see U.S. Publ. No. 2004-0009538-A1; FIG. 2B). Identical results were obtained with extracts from +/+ and ATE1$^{-/-}$ embryos. In addition to being consistent with the conclusions from pulse-chase analyses in EF cells, these findings confirmed the absence of R-transferase activity from ATE1$^{-/-}$ embryos.

EXAMPLE 6

Assays in Mouse Embryonic Fibroblasts

Primary mouse EFs were established from E13.5 ATE1$^{-/-}$ and littermate +/+ embryos as described, and immortalized to increase transfection efficiency. Cells were transiently transfected with pcDNA3flagDHFRhaUbXnsP4flag, which expressed $^f$DHFR$^h$-UbR48-X-nsP4$^f$ from the PCMV promoter. Cells were labeled with $^{35}$S-EXPRESS (New England Nuclear) for 10 min at 37° C., followed by a chase for 0, 1, and 2 hr in the presence of cycloheximide, preparation of extracts, precipitation with anti-flag antibody, SDS-10% PAGE, autoradiography, and quantitation using PhosphorImager™ software. In other pulse-chase experiments, ATE1$^{-/-}$ EFs were co-transfected with a plasmid expressing X-nsP4$^f$ (fDHFRh-UbR48-X-nsP4 f) and either pCDNA3yATE1, expressing *S. cerevisiae* ATE1, or pCDNA3yATE1C23A, which expressed ATE1C23SA, bearing Cys→Ala mutation at position 23.

To examine the in vivo degradation of N-end rule substrates in ATE1$^{-/-}$ cells, immortalized embryonic fibroblast (EF) cell lines were established from ATE1$^{-/-}$ and littermate +/+ embryos. The EFs were transiently transfected with plasmids that expressed X-nsP4$^f$, a set of otherwise identical 69K flag-tagged Sindbis virus RNA polymerase proteins bearing different N-terminal residues. X-nsP4$^f$ proteins were expressed as parts of $^f$DHFR$^h$-Ub$^{R48}$-X-nsP4$^f$ fusions, the UPR (Ub/protein/reference) constructs, in which the reference moiety $^f$DHFR$^h$-Ub$^{R48}$ contained an epitope-tagged mouse dihydrofolate reductase (DHFR). DHFR$^h$-Ub$^{R48}$-X-nsP4$^f$ is cotranslationally cleaved by deubiquitylating enzymes (DUBs) at the Ub$^{R48}$-X junction, yielding the long-lived $^f$DHFR$^h$-Ub$^{R48}$ reference protein and a test protein X-nsP4$^f$. Through the presence of a "built-in" reference protein, the UPR technique increases the accuracy of pulse-chase assays, and in addition allows the detection of a test protein's degradation during the pulse.

R-transferase substrates were short-lived in +/+ EF cells: more than 90% of pulse-labeled Asp-nsP4$^f$ and Glu-nsP4$^f$ were degraded by 2 hr of chase. In contrast, both Asp-nsP4$^f$ and Glu-nsP4$^f$ were completely stabilized in ATE1$^{-/-}$ cells, whereas Arg-nsP4$^f$, bearing a primary (arginylation-independent) destabilizing N-terminal residue, remained short-lived in these cells. Strikingly, although the mouse ATE1-encoded R-transferases cannot arginylate N-terminal Cys, the normally short-lived Cys-nsP4$^f$ also became long-lived in ATE1$^{-/-}$ EF cells, indicating that ATE1 is required for the arginylation of N-terminal Cys, through a mechanism determined by the inventors to involve a catalytic oxidation of N-terminal cysteine residues.

EXAMPLE 7

Gene Circuits Involving ATE1

To begin a search for mouse genes whose expression is significantly altered in the ATE1$^{-/-}$ background, RT-PCR and Northern analyses were carried out with total RNA from +/+ and littermate ATE1$^{-/-}$ embryos proper, their yolk sacs, and their hearts, using mouse cDNA probes specific for genes that encode the following proteins: NTAN1, UBR1, UBR2 (components of the N-end rule pathway); eHand, ICAM2, GATA6, Nfarc 1, dHand, NF1, RXRα, FOG2, GATA4, MEF2c, Neuropilin 1, TEF1, N-myc, RARα, ErbB2 (proteins whose functions include heart development); TIE1, TIE2, FLK1, FLK2, FLT1, FLT4, βH1, GATA1, I1-3R, CD34, VEGF, VEGF-B, VEGF-C, VEGF-D, ANG1, ANG2, ANG3, EfnB1, EfnB2, EfnA1, EphB2 (proteins whose functions include vascular development). No significant differences were detected in the expression of these genes between the ATE1 $^{-/-}$ and +/+ genetic backgrounds, making it more likely that the absence of ATE1 impacted a previously undescribed circuit.

The N-end rule is implicated in a variety of physiological processes, including angiogenesis. Mice lacking the gene ATE1 were shown to have extensive defects in angiogenic development. Because of the importance of the arginylation pathway to angiogenesis, inhibitors of the N-terminal arginyl transferase activity can be used as anti-angiogenic compounds for the treatment of tumors, and particularly of solid tumors. Recent studies identified the mammalian Met-aminopeptidase MetAP2 as the target of fumagillin and related inhibitors of angiogenesis. Upon inhibition of MetAP2, some intracellular proteins partially retain their N-terminal Met residues. The N-terminal Met-Cys bond (but neither Met-Asp nor Met-Glu) can be cleaved by MetAP2. The results. suggest that metabolic stabilization of an arginylation-dependent N-end rule substrate(s) in mouse ATE1$^{-/-}$ cells causes angiogenic and cardiogenic defects. Fumagillin and related drugs may act by partially inhibiting the N-terminal Met-Cys cleavage and thereby partially stabilizing an otherwise short-lived repressor(s) of angiogenesis that bears a Cys-containing N-degron. If the repressor's half-life is normally short enough, even a small fraction of repressor molecules that retain Met-Cys and are, therefore, long-lived, would yield a strong increase in the repressor's steady-state level, thereby possibly accounting for the finding that even a partial inhibition of MetAP2 is sufficient to block proliferation of endothelial cells. Likewise, inhibition of the cysteine oxidase pathway and/or arginylation dependent pathway also is likely to block such proliferation.

EXAMPLE 8

Assays of Arginyl Transferase Activity

Mouse ATE1 was isolated and chimeric and ATE1$^{-/-}$ mice were generated as described above (see, also, U.S. Publ. No. 2004-0023311-A1, which is incorporated herein by reference). Phenotypes of ATE1$^{-/-}$ embryos were observed mainly with mice of the C57BL/6J-129SvEv (mixed) background, and confirmed in the 129SvEv (inbred) background. RT-PCR, Southern and northern blot analyses, and PCR-mediated genotyping of embryos and pups were performed. Standard procedures were used for thin sectioning and staining with hematoxylin/eosin, X-Gal, or anti-PECAM-1 antibody (clone MEC 13.3, Pharmingen). The TUNEL assay was performed using a kit (Roche) and fluorescein-dUTP. For R-transferase assays, Ub-X-βgal proteins were purified from E. coli carrying pKKUbXbgal plasmids. The R-transferase reaction (50 ml) contained S105 supernatant (0.5 mg of protein per ml) from either EF cells or whole embryos, Ub-X-βgal or α-lactalbumin (0.2 mg/ml), E. coli tRNA (1 mg/ml), E. coli aminoacyl-tRNA synthetases (50 mg/ml), puromycin (0.2 mM), bestatin (0.15 mM), 5 mM MG132 (proteasome inhibitor), 0.4 mM Lys-Ala dipeptide (inhibitor of post-arginylation steps in the N-end rule pathway), 1 mM ATP, 10 mM creatine phosphate, 0.1 M KCl, 5 mM MgCl$_2$, 50 mM β-mercaptoethanol, 50 mM Tris-HCl (pH 8.0) and 0.3 mM $^3$H-arginine (New England Nuclear). The reaction mixture was incubated for 3 hr (2 hr with embryo extracts) at 37° C. A 20 ml sample was precipitated with 10% TCA, and analyzed by SDS-12% PAGE and fluorography.

Primary mouse EFs were established from E13.5 ATE1$^{-/-}$ and littermate +/+ embryos and immortalized to increase transfection efficiency. Cells were transiently transfected with pcDNA3flagDHFRhaUbXnsP4flag, which expressed fDHFR$^h$-UbR48-X-nsP4$^f$ (and the main text) from the PCMV promoter. Cells were labeled with 35S-EXPRESS label (New England Nuclear) for 10 min at 37° C., followed by a chase for 0, 1, and 2 hr in the presence of cycloheximide, preparation of extracts, precipitation with anti-flag antibody, SDS-10% PAGE, autoradiography, and quantitation using PhosphorImager™ software. In other pulse-chases, ATE1$^{-/-}$ EFs were co-transfected with a plasmid expressing X-nsP4$^f$ (fDHFRh-UbR48-X-nsP4 f) and either pCDNA3yATE1, expressing S. cerevisiae ATE1, or pCDNA3yATE1C23A, which expressed ATE1C23SA, bearing Cys→Ala mutation at position 23.

EXAMPLE 9

Arginylation of N-Terminal Cysteine-Containing Polypeptides

To measure the N-terminal arginylation directly, either purified Ub-X-βgal proteins (X=Met, Arg, Glu, Cys) or purified human α-lactalbumin (bearing N-terminal Glu) were added to +/+ and ATE1$^{-/-}$ immortalized embryonic fibroblast (EF) cell extracts supplemented with ATP, total E. coli tRNA and a mixture of E. coli aminoacyl-tRNA synthetases. SDS-PAGE and fluorography were used to detect covalent conjugation of $^3$H-Arg to test proteins in these extracts. Ub-X-βgals are rapidly deubiquitylated in vivo and in cell-free extracts, yielding X-βgal test proteins. As expected, Asp-βgal, Glu-βgal and α-lactalbumin were arginylated in the extracts from +/+ EF cells, whereas Arg-βgal and Met-βgal, bearing a primary destabilizing and a stabilizing N-terminal residue, respectively, were not arginylated. Crucially, no arginylation of Asp-βgal, Glu-βgal and α-lactalbumin could be detected in ATE1$^{-/-}$ EF extracts, even after prolonged fluorographic exposures. Identical results were obtained with extracts from +/+ and ATE$^{-/-}$ embryos. In addition to being consistent with the conclusions from pulse-chase analyses in EF cells, these findings confirmed the absence of R-transferase activity from ATE1$^{-/-}$ embryos.

The N-terminal Cys, of Cys-βgal, was not arginylated in either +/+ or ATE1$^{-/-}$ extracts, in contrast to N-terminal Asp and Glu, suggesting that the previously observed arginylation of N-terminal Cys, and the demonstrated ATE1 dependence of the in vivo degradation of Cys-bearing N-end rule substrates in mouse cells involved a modification of N-terminal Cys prior to its arginylation. In this interpretation, the absence of arginylation of Cys-βgal in an extract from +/+ mouse cells could be caused, for example, by inactivation of a Cys-modifying enzyme in the extract. A comparison of Asp and Cys structures suggested that either the Cys sulfinic acid residue (CysO$_2$, an oxidized derivative of Cys) or the cysteic acid residue (CysO$_3$, a further oxidized Cys derivative), may be sufficiently close in structure and charge distribution to Asp to serve as a substrate of R-transferases. Consistent with this possibility, a protease called Asp-N cleaves peptide bonds N-terminal to either the Asp or CysO$_3$ residues. Another class of enzymes, aspartate aminotransferases, can utilize either Asp or oxidized Cys as substrates.

This example illustrates that degradation of a test protein bearing N-terminal Cys is tRNA-dependent (implying the involvement of R-transferase), similarly to the degradation of otherwise identical proteins bearing N-terminal Asp, Glu, Asn or Gln, and in contrast to degradation of otherwise identical proteins bearing primary destabilizing N-terminal residues. The normally short-lived Cys-bearing N-end rule substrates are stabilized in mouse ATE1$^{-/-}$ cells, although the ATE1-encoded R-transferases that are absent from these cells cannot arginylate N-terminal Cys upon their expression in ate1Δ S. cerevisiae.

EXAMPLE 10

Generation of RGS4

To produce RGS4, mouse L cells were transiently transfected with pCDNA3RGS4flagHis$_6$, which expressed mouse RGS4-flag-His$_6$ from the PCMV promoter and was constructed from the pcDNA3RGS4 plasmid. Cell extracts were prepared 30 hr later; RGS4-flag-His$_6$ was purified using Ni-NTA Magnetic Agarose Beads (Qiagen), then treated with 25 mM iodoacetamide in 7 M urea, followed by SDS-PAGE, the transfer onto Immobilon-P membrane, and sequencing by Edman-degradation, using the 476A sequencer (Perkin-Elmer). For mass spectrometry, RGS4-flag-His$_6$ was treated with 90 mM iodoacetic acid in 8 M urea for 50 min at -20° C., then cleaved with CNBr in 55% HCOOH under argon atmosphere for 12 hr in the dark, followed by reverse phase HPLC and on-line, fragmentation-based mass spectrometric sequencing of peptides.

EXAMPLE 11

Arginylation of N-Terminal Cysteine-Containing RGS4

The existence of amino-terminal arginylated Cys residues as CysO$_2$ or CysO$_3$ was verified and confirmed with mouse RGS4, a GTPase-activating (GAP) protein that bears N-terminal Cys and was previously shown to be arginylated and degraded by the N-end rule pathway in rabbit reticulocyte extracts. RGS4-His$_6$ was transiently expressed in mouse L cells, purified, treated with iodoacetamide to alkylate Cys residues (thereby making them identifiable by the sequencing procedure used), and was N-terminally sequenced by Edman degradation. The results indicated the presence of two RGS4 proteins, an arginylated and unarginylated one, the former being a major species. Remarkably, whereas the expected Cys residue at position 12 of arginylated RGS4 could be identified as alkylated Cys, the expected (alkylated) Cys residue at position 2 (position 1 in the unarginylated RGS4) could not be identified by the Edman procedure, indicating that a residue at this position existed as a derivative of Cys prior to alkylation, and thereby precluded it. To determine the identity of a residue at position 2, the purified, alkylated RGS4 was cleaved with cyanogen bromide (CNBr), followed by HPLC fractionation and on-line mass spectrometric sequencing of CNBr-produced peptides. Mass spectra derived from the arginylated N-terminal peptide of RGS4 demonstrated that the mass of a residue at position 2 was increased by 48 (±0.1) Da in comparison to the expected mass of Cys-2 (see U.S. Publ. No. 2004-0023311-A1). These results identified residue 2 as a cysteic acid (CysO$_3$) residue.

EXAMPLE 12

Rescue of the Destabilizing Activity of Cysteine in Mouse ATE1$^{-/-}$ Cells Verification and confirmation of the fact that the yeast R-transferase should be able to rescue the destabilizing activity of Cys in mouse ATE1$^{-/-}$ cells, owing to the presence of Cys-oxidation activity in these cells was obtained by the present example. Pulse-chase assays were carried out with mouse ATE1$^{-/-}$ EF cells that expressed X-nsP4$^f$ proteins (X=Met, Asp, Cys) and either the wild-type S. cerevisiae ATE1 (R-transferase) or ATE1$^{C23SA}$, an enzymatically impaired missense mutant. The metabolic stability of long-lived Met-nsP4$^f$ (bearing a stabilizing N-terminal residue) was unchanged in the presence of yeast ATE1. In contrast, both Asp-nsP4$^f$ and Cys-nsP4$^f$, which were long-lived in mouse ATE1$^{-/-}$ EF cells, became short-lived in the presence of yeast ATE1. The complementation by yeast R-transferase required its enzymatic activity, since ATE1$^{C23SA}$, a catalytically impaired missense mutant, had a significantly weaker effect. In addition to supporting the Cys-oxidation/arginylation hypothesis, these results suggested that the oxidation of N-terminal Cys is an enzymatic (rather than uncatalyzed) reaction, since the intracellular solvent conditions, including redox potential, are likely to be similar in mammalian and yeast cells. The fact of stoichiometric oxidation of N-terminal Cys in mouse cells indicated the same conclusion.

These results show that S. cerevisiae R-transferase, which cannot arginylate N-terminal Cys, can rescue the in vivo arginylation and degradation of Cys-bearing N-end rule substrates in mouse ATE1$^{-/-}$ cells. Such a cell-based system can be used to identify modulators of cysteine oxygenase activity, which is necessary for degradation of proteins having an N-terminal cysteine residue.

In contrast to most of the destabilizing residues, including Asp and Glu, Cys can be exposed at the N-terminus of a protein substrate by Met-aminopeptidases, which cleave off the N-terminal Met of a newly formed protein if the side chain of a second residue is small enough; only Cys, Ala, Thr, and Ser of the mammalian N-end rule satisfy this condition. Two Cys-bearing mouse proteins, RGS4 and RGS16, were recently identified as N-end rule substrates. A mammalian genome encodes a few hundred proteins containing the N-terminal Met-Cys sequence. However, given the constraints of N-degron organization, the presence of Cys at the N-terminus of a protein is not, by itself, sufficient to render this protein an N-end rule substrate. In addition, the oxidation (and subsequent arginylation) of N-terminal Cys may compete with its other known modifications, including acetylation and palmitoylation. N-end rule substrates that bear the arginylation-dependent destabilizing N-terminal residues (Asn, Gln, Asp, Glu, and Cys) can also be produced through cleavages anywhere in a protein's polypeptide chain. For example, the conditional cleavage of a subunit of the mammalian cohesin complex at the metaphase-anaphase transition is predicted to produce a putative N-end rule substrate whose degradation would require N-terminal arginylation. Since the failure to degrade, through the N-end rule pathway, a cohesin fragment has been shown to impair the fidelity of chromosome segregation in S. cerevisiae, mouse ATE1$^{-/-}$ cells may exhibit an increased chromosome instability.

Discussion

Figure 2:
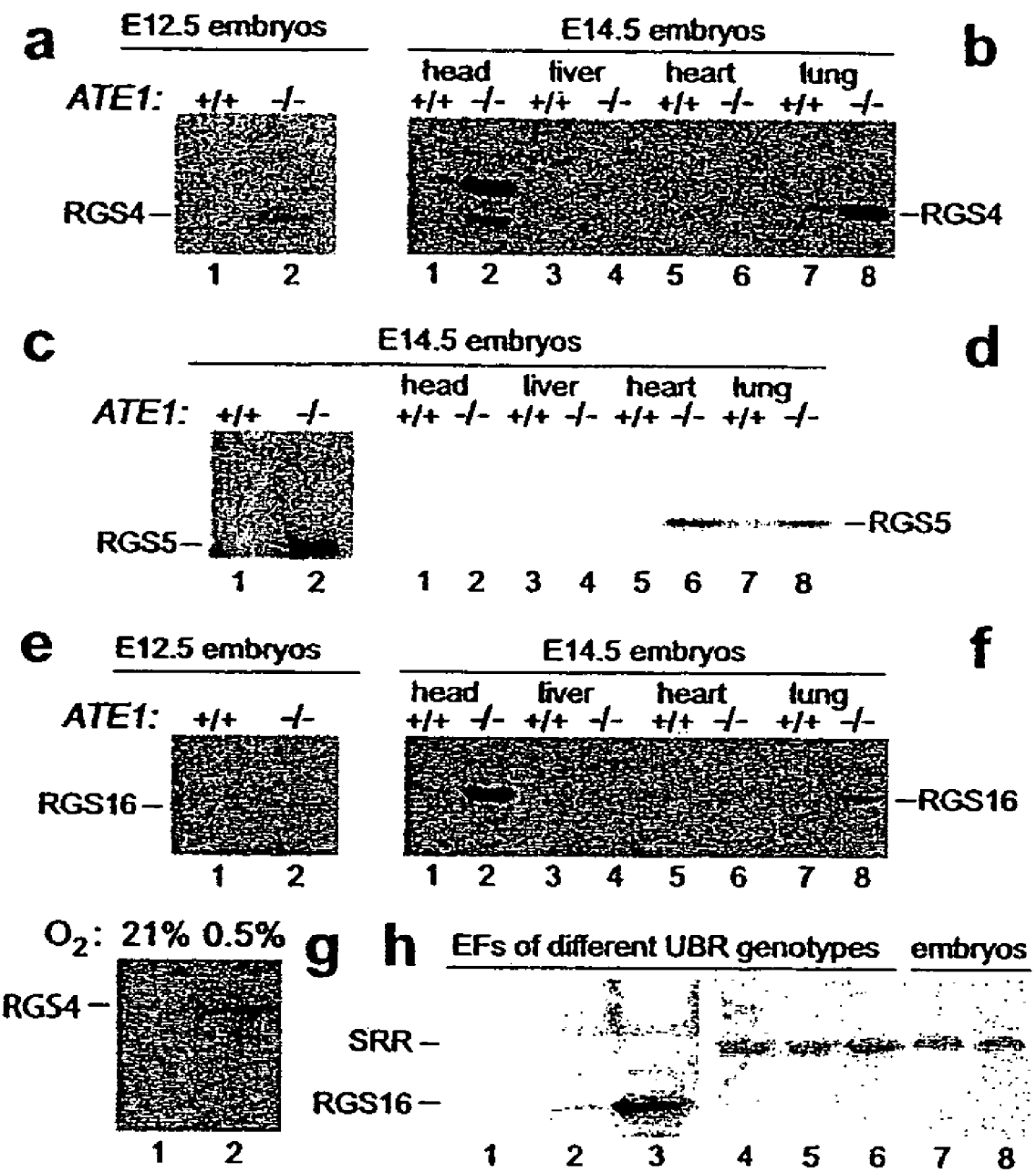
FIG. 2 shows the results of immunoassays with strongly increased levels of RGS4, RGS5 and RGS16 proteins in ATE1$^{-/-}$ embryos.

We showed here that the oxidation of N-terminal Cys in a polypeptide is essential for arginylation of Cys by ATE1-encoded Arg-tRNA-protein transferases (R-transferases) (FIG. 1c-j). Most importantly, we also discovered that the arginylation branch of the N-end rule pathway (FIG. 1a) is a sensor of nitric oxide (NO) that functions through its ability to destroy specific regulatory proteins bearing N-terminal Cys, at the rates controlled by NO, and apparently by oxygen as well (FIGS. 2-4). The first examples of such regulators, RGS4, RGS5 and RGS16, are also the first physiological substrates of mammalian N-end rule pathway. These proteins down-regulate specific Gα subunits of G proteins by increasing their GTPase activity. Through the conditional destruction of RGS4, RGS5 and RGS16, the N-end rule pathway is thus involved in regulation of signaling by G protein-coupled receptors.

The above "unification" of a Ub-dependent proteolytic pathway and NO signaling opens up new vistas for understanding both. Most of the previously known regulation by NO was based on changes in the functional (e.g., enzymatic) activity of NO-modified proteins. In contrast, a Cys-containing N-degron of a protein makes possible the NO-mediated control of circuits that contain this protein, through its NO-dependent degradation by the N-end rule pathway. The observed stabilization of RGS4 in cells grown in low oxygen (FIG. 2g) suggests an involvement of oxygen or its derivatives in this NO-dependent regulation. That would also be expected from the NO results alone (FIGS. 3 and 4), given multiple links between the in vivo chemistries of NO and oxygen. Our in vitro assay for NO-dependent arginylation of N-terminal Cys (FIG. 4) should eventually yield a detailed understanding of chemical transformations that result in oxidation of this uniquely positioned Cys residue.

The pathway of control by NO (FIG. 1a) targets proteins that bear N-terminal Cys followed by a basic residue. This motif is present in about 30 proteins encoded by the mouse (and human) genome, including RGS4, RGS5, and RGS16. More than half of non-RGS proteins in this set are of entirely unknown functions, while the rest are barely characterized. The N-terminal Cys residues of RGS4, RGS5 and RGS16 can be modified through palmitoylation as well. The two modifications are expected to be mutually exclusive, and in addition act in opposite ways, in that palmitoylation increases the activity of RGSs as down-regulators of G proteins, whereas NO-dependent arginylation and destruction of RGSs reduce their activity by decreasing their levels in a cell.

RGS4 is a physiological inhibitor of angiogenesis and other tubulogenesis pathways. Up-regulation of RGS4 perturbs cardiovascular homeostasis in mice and is a molecular correlate of human heart failure. Mouse ATE1$^{-/-}$ embryos, which lack R-transferases and thus lack arginylation, die before E17 with cardiovascular defects. Our findings that the levels of RGS4, RGS5 and RGS16 are greatly increased in the hearts and other organs of ATE1$^{-/-}$ embryos (FIG. 2), and that NO is required for proteolytic down-regulation of these RGSs (FIGS. 3 and 4) are likely to account, in part, for the known role of NO, at physiologically optimal levels, in suppressing pathological changes in the heart. The functions of NO in cardiovascular homeostasis include stimulation of cGMP formation by guanylyl cyclase and regulation of cardiac contractility through S-nitrosylation of the calcium release channel. Our results revealed an entirely different, mutually nonexclusive mechanism of NO signaling in the heart and other organs: the control of regulatory proteins bearing N-terminal Cys through their NO-dependent, arginylation-mediated degradation by the N-end rule pathway. Thus, pharmacological manipulation of activities or expression of R-transferases may provide an alternative, more selective route to clinically beneficial effects that are currently achieved through drugs that alter the levels of NO.

Mammalian R-transferases are strong sequelogs of yeast (fungal) ATE1 R-transferases. However, while the inactivation of mouse ATE1 results in embryonic lethality, a deletion of *S. cerevisiae* ATE1 renders cells unable to degrade reporters with N-terminal Asp or Glu, but has not been found to cause any other abnormal phenotype. Our findings suggest that one function of arginylation in this and other organisms might be to serve as a sensor of nitrosative/oxidative stress. It remains to be determined whether the discovered signaling by NO proceeds exclusively through oxidation of Cys-containing N-degrons (FIG. 1a), or whether NO can also function at other steps of the N-end rule pathway, for example through S-nitrosylation of its Ub ligases or R-transferases.

A remarkable preponderance of circuits relevant to the findings of this work involve arginine. Specifically: (i) Arg is a direct precursor of NO (FIG. 1a); (ii) the levels of Arg are tightly controlled, and are often down-regulated by invading pathogens; (iii) Arg is a part of Arg-tRNA (a co-substrate of R-transferase), suggesting a connection between the N-end rule pathway and regulation of translation; (iv) Arg is a primary destabilizing residue, and is also conjugated to N-end rule substrates bearing N-terminal Asp, Glu or oxidized Cys (FIG. 1a). Finally, some Arg residues in proteins undergo methylation or deimination, the latter a conversion of positively charged Arg to uncharged citrulline. It remains to be determined whether methylation or deimination of Arg in vivo involve N-terminal Arg, and whether a set of circuits that has now been shown to connect the N-end rule pathway and the signaling by NO holds yet another Arg-linked surprise.

REFERENCES

Each of the following publications is incorporated herein by reference.

1. Bachmair, A., Finley, D. & Varshavsky, A. In vivo half-life of a protein is a function of its amino-terminal residue. *Science* 234, 179-186 (1986).
2. Varshavsky, A. The N-end rule: functions, mysteries, uses. *Proc. Natl. Acad Sci. USA* 93, 12142-12149 (1996).
3. Varshavsky, A. The N-end rule and regulation of apoptosis. *Nature Cell Biol.* 5, 373-376 (2003).
4. Kwon, Y. T. et al. Female lethality and apoptosis of spermatocytes in mice lacking the UBR2 ubiquitin ligase of the N-end rule pathway. *Mol. Cell. Biol.* 23, 8255-8271 (2003).
5. Bachmair, A. & Varshavsky, A. The degradation signal in a short-lived protein. *Cell* 56, 1019-1032 (1989).
6. Suzuki, T. & Varshavsky, A. Degradation signals in the lysine-asparagine sequence space. *EMBO J.* 18, 6017-6026 (1999).
7. Hershko, A., Ciechanover, A. & Varshavsky, A. The ubiquitin system. *Nature Med.* 10, 1073-1081 (2000).
8. Pickart, C. Back to the future with ubiquitin. *Cell* 116, 181-190 (2004).
9. Baker, R. T. & Varshavsky, A. Yeast N-terminal amidase: a new enzyme and component of the N-end rule pathway. *J. Biol. Chem.* 270, 12065-12074 (1995).
10. Kwon, Y. T. et al. Altered activity, social behavior, and spatial memory in mice lacking the NTAN1 amidase and the asparagine branch of the N-end rule pathway. *Mol. Cell. Biol.* 20, 4135-4148 (2000).
11. Kwon, Y. T., Kashina, A. S. & Varshavsky, A. Alternative splicing results in differential expression, activity, and localization of the two forms of arginyl-tRNA-protein transferase, a component of the N-end rule pathway. *Mol. Cell. Biol.* 19, 182-193 (1999).
12. Kwon, Y. T. et al. An essential role of N-terminal arginylation in cardiovascular development. *Science* 297, 96-99 (2002).
13. Xie, Y. & Varshavsky, A. The E2-E3 interaction in the N-end rule pathway: the RING-H2 finger of E3 is required for the synthesis of multiubiquitin chain. *EMBO J.* 18, 6832-6844 (1999).
14. Du, F., Navarro-Garcia, F., Xia, Z., Tasaki, T. & Varshavsky, A. Pairs of dipeptides synergistically activate the binding of substrate by ubiquitin ligase through dissocia- 15. Kwon, Y. T., Xia, Z., Davydov, I. V., Lecker, S. H. & Varshavsky, A. Construction and analysis of mouse strains lacking the ubiquitin ligase UBR1 (E3-alpha) of the N-end rule pathway. *Mol. Cell. Biol.* 21, 8007-8021 (2001).

16. Turner, G. C., Du, F. & Varshavsky, A. Peptides accelerate their uptake by activating a ubiquitin-dependent proteolytic pathway. *Nature* 405, 579-583 (2000).

17. Rao, H., Uhlmann, F., Nasmyth, K. & Varshavsky, A. Degradation of a cohesin subunit by the N-end rule pathway is essential for chromosome stability. *Nature* 410, 955-960 (2001).

18. Ditzel, M. et al. Degradation of DIAP1 by the N-end rule pathway is essential for regulating apoptosis. *Nature Cell Biol.* 5, 467-473 (2003).

19. Kitamura, K. et al. Phosphorylation of Mei2 and Ste11 by Pat1 kinase inhibits sexual differentiation via ubiquitin proteolysis and 14-3-3 protein in fission yeast. *Dev. Cell* 1, 389-399 (2001).

20. Yoshida, S., Ito, M., Gallis, J., Nishida, I. & Watanabe, A. A delayed leaf senescence mutant is defective in arginyl-tRNA-protein arginyl-transferase, a component of the N-end rule pathway in *Arabidopsis*. *Plant J.* 32, 129-137 (2002).

21. Ignarro, L. J. Nitric oxide as a unique signaling molecule in the vascular system: a historical overview. *J. Physiol. Pharmacol.* 53, 503-514 (2002).

22. Boehning, D. & Snyder, S. H. Novel neural modulators. *Annu. Rev. Neurosci.* 26, 105-131 (2003).

23. Nathan, C. Specificity of a third kind: reactive oxygen and nitrogen intermediates in cell signaling. *J. Clin. Invest.* 111, 769-778 (2003).

24. Regulski, M., Stasiv, Y., Tully, T. & Enikolopov, G. Essential function of nitric oxide synthase in *Drosophila*. *Curr. Biol.* 14, R881-R882 (2004).

25. Hess, D. T., Matsumoto, A., Nudelman, R. & Stamler, J. S. S-nitrosylation: spectrum and specificity. *Nature Cell Biol.* 3, E46-E49 (2001).

26. Eu, J. P., Sun, J., Xu, L., Stamler, J. S. & Meissner, G. The skeletal muscle calcium release channel: coupled O2 sensor and NO signaling functions. *Cell* 102, 499-509 (2000).

27. Gu, Z. et al. S-nitrosylation of matrix metalloproteinases: signaling pathway to neuronal cell death. *Science* 297, 1186-1190 (2002).

28. Palacios-Callender, M., Quintero, M., Hollis, V. M., Springett, R. J. & Moncada, S. Endogenous NO regulates superoxide production at low oxygen concentrations by modifying the redox state of cytochrome oxidase. *Proc. Natl. Acad. Sci. USA* 101, 7630-7635 (2004).

29. Pittner, J., Liu, R., Brown, R., Wolgast, M. & Persson, A. E. G. Visualization of nitric oxide production and intracellular calcium in juxtamedullary afferent arteriolar endothelial cells. *Acta Physiol. Scand.* 179, 309-317 (2003).

30. Jaffrey, S. R., Erdjument-Bromage, H., Ferris, C. D., Tempst, P. & Snyder, S. H. Protein S-nitrosylation: a physiological signal for neuronal nitric oxide. *Nature Cell Biol.* 3, 193-197 (2001).

31. Gonda, D. K. et al. Universality and structure of the N-end rule. *J. Biol. Chem.* 264, 16700-16712 (1989).

32. Wieland, T. & Mittman, C. Regulators of G-protein signalling: multifunctional proteins with impact on signalling in the cardiovascular system. *Pharmacol. Therapeut.* 97, 95-115 (2003).

33. Balzi, E., Choder, M., Chen, W., Varshavsky, A. & Goffeau, A. Cloning and functional analysis of the arginyl-tRNA-protein transferase gene ATE1 of *Saccharomyces cerevisiae*. *J Biol. Chem.* 265, 7464-7471 (1990).

34. Varshavsky, A. 'Spalog' and 'sequelog': neutral terms for spatial and sequence similarity. *Curr. Biol.* 14, R181-R183 (2004).

35. Berman, D. M. & Gilman, A. G. Mammalian RGS proteins: Barbarians at the gate. *J. Biol. Chem.* 273, 1269-1272 (1998).

36. De Vries, L., Zheng, B., Fischer, T., Elenko, E. & Farquhar, M. G. The regulator of G proteins signaling family. *Annu. Rev. Pharmacol. Toxicol.* 40, 235 (2000).

37. Krumins, A. M. et al. Differentially regulated expression of endogenous RGS4 and RGS7. *J. Biol. Chem.* 279, 2593-2599 (2004).

38. Davydov, I. V. & Varshavsky, A. RGS4 is arginylated and degraded by the N-end rule pathway in vitro. *J. Biol. Chem.* 275, 22931-22941 (2000).

39. Jones, T. L. Z. Role of palmitoylation in RGS protein function. *Meth. Enzymol.* 389, 33-55 (2004).

40. Smotrys, J. E. & Linder, M. E. Palmitoylation of intracellular signaling proteins: regulation and function. *Annu. Rev. Biochem.* 73, 559-587 (2004).

41. Kempf, T. & Wollert, K. C. Nitric oxide and the enigma of heart hypertrophy. *BioEssays* 26, 608-615 (2004).

42. Khan, S. A. et al. Neuronal nitric oxide synthase negatively regulates xanthine oxidoreductase inhibition of cardiac excitation-contraction coupling. *Proc. Natl. Acad. Sci. USA* 101, 15944-15948 (2004).

43. DiAntonio, A. & Hicke, L. Ubiquitin-dependent regulation of the synapse. *Annu. Rev. Neurosci.* 27, 223-246 (2004).

44. Wang, Y. M. & Ingoglia, N. A. N-terminal arginylation of sciatic nerve and brain proteins following injury. *Neurochem. Res.* 22, 1453-1459 (1997).

45. Morris, D. W. et al. Confirming RGS4 as a susceptibility gene for schizophrenia. *Am. J Med. Genet.* 125B, 50-53 (2004).

46. Liu, L., Zeng, M., Hausladen, A., Heitman, J. & Stamler, J. S. Protection from nitrosative stress by yeast flavohemoglobin. *Proc. Natl. Acad. Sci. USA* 97, 4672-4676 (2000).

47. Wong, C. M., Zhou, Y., Ng, R. W. M., Kung, H. F. & Jin, D. Y. Cooperation of yeast peroxiredoxins Tsa1p and Tsa2p in the cellular defense against oxidative and nitrosative stress. *J. Biol. Chem.* 277, 5385-5394 (2002).

48. Darwin, K. H., Ehrt, S., Gutierez-Ramos, J. C., Weich, N. & Nathan, C. F. The proteasome of *Mycobacterium tuberculosis* is required for resistance to nitric oxide. *Science* 302, 1963-1966 (2003).

49. Pieters, J. & Ploegh, H. Chemical warfare and microbial defense. *Science* 302, 1900-1902 (2003).

50. Ausubel, F. M. et al. (eds.) *Current Protocols in Molecular Biology*. (Wiley-Interscience, New York, 2002).

51. Papaioannou, V. E. & Behringer, R. R. *Mouse Phenotypes. A handbook of mutational analysis*. (Cold Spring Harbor Laboratory Press, Cold Spring Harbor, N.Y., 2005).

52. Nagy, A., Gertsenstein, M., Vintersten, K. & Behringer, R. *Manipulating the Mouse Embryo: A Laboratory Manual*. (Cold Spring Harbor Laboratory Press, Cold Spring Harbor, N.Y., 2002).

53. Hiol, A. et al. Palmitoylation regulates regulators of G-protein signaling (RGS) 16 function. I. Mutation of amino-terminal cysteine residue on RGS16 prevents its targeting to lipid rafts and palmitoylation of an internal cysteine residue. *J. Biol. Chem.* 278, 19301-19308 (2003).

54. Harlow, E. & Lane, D. Using Antibodies: a laboratory manual. (Cold Spring Harbor Laboratory Press, Cold Spring Harbor, N.Y., 1999).

55. Suzuki, T. & Varshavsky, A. Degradation signals in the lysine-asparagine sequence space. *EMBO J.* 18, 6017-6026 (1999).
56. Sissler, M., Eriani, G., Martin, F., Giege, R. & Florentz, C. Mirror image alternative interaction patterns of the same tRNA with either class I arginyl-tRNA synthetase or class II aspartyl-tRNA synthetase. *Nuc. Acids Res.* 25, 4899-4906 (1997).

EXAMPLE 1

REFERENCES

1. Bachmair, A., Finley, D. & Varshavsky, A. In vivo half-life of a protein is a function of its amino-terminal residue. *Science* 234, 179-186 (1986).
2. Varshavsky, A. The N-end rule: functions, mysteries, uses. *Proc. Natl. Acad. Sci. USA* 93, 12142-12149 (1996).
3. Varshavsky, A. The N-end rule and regulation of apoptosis. *Nature Cell Biol.* 5, 373-376 (2003).
4. Kwon, Y. T. et al. Female lethality and apoptosis of spermatocytes in mice lacking the UBR2 ubiquitin ligase of the N-end rule pathway. *Mol. Cell. Biol.* 23, 8255-8271 (2003).
5. Bachmair, A. & Varshavsky, A. The degradation signal in a short-lived protein. *Cell* 56, 1019-1032 (1989).
6. Suzuki, T. & Varshavsky, A. Degradation signals in the lysine-asparagine sequence space. *EMBO J.* 18, 6017-6026 (1999).
7. Hershko, A., Ciechanover, A. & Varshavsky, A. The ubiquitin system. *Nature Med.* 10, 1073-1081 (2000).
8. Pickart, C. Back to the future with ubiquitin. *Cell* 116, 181-190 (2004).
9. Baker, R. T. & Varshavsky, A. Yeast N-terminal amidase: a new enzyme and component of the N-end rule pathway. *J. Biol. Chem.* 270, 12065-12074 (1995).
10. Kwon, Y. T. et al. Altered activity, social behavior, and spatial memory in mice lacking the NTAN1 amidase and the asparagine branch of the N-end rule pathway. *Mol. Cell. Biol.* 20, 4135-4148 (2000).
11. Kwon, Y. T., Kashina, A. S. & Varshavsky, A. Alternative splicing results in differential expression, activity, and localization of the two forms of arginyl-tRNA-protein transferase, a component of the N-end rule pathway. *Mol. Cell. Biol.* 19, 182-193 (1999).
12. Kwon, Y. T. et al. An essential role of N-terminal arginylation in cardiovascular development. *Science* 297, 96-99 (2002).
13. Du, F., Navarro-Garcia, F., Xia, Z., Tasaki, T. & Varshavsky, A. Pairs of dipeptides synergistically activate the binding of substrate by ubiquitin ligase through dissociation of its autoinhibitory domain. *Proc. Natl. Acad. Sci. USA* 99, 14110-14115 (2002).
14. Tasaki, T. et al. A family of mammalian E3 ubiquitin ligases that contain the UBR box motif and recognize N-degrons. *Mol. Cell. Biol. (in press)* (2005).
15. Gonda, D. K. et al. Universality and structure of the N-end rule. *J. Biol. Chem.* 264, 16700-16712 (1989).
16. Turner, G. C., Du, F. & Varshavsky, A. Peptides accelerate their uptake by activating a ubiquitin-dependent proteolytic pathway. *Nature* 405, 579-583 (2000).
17. Ditzel, M. et al. Degradation of DIAP1 by the N-end rule pathway is essential for regulating apoptosis. *Nature Cell Biol.* 5, 467-473 (2003).
18. Rao, H., Uhlmann, F., Nasmyth, K. & Varshavsky, A. Degradation of a cohesin subunit by the N-end rule pathway is essential for chromosome stability. *Nature* 410, 955-960 (2001).
19. Ignarro, L. J. Nitric oxide as a unique signaling molecule in the vascular system: a historical overview. *J. Physiol. Pharmacol.* 53, 503-514 (2002).
20. Boehning, D. & Snyder, S. H. Novel neural modulators. *Annu. Rev. Neurosci.* 26, 105-131 (2003).
21. Hess, D. T., Matsumoto, A., Kim, S.-O., Marshall, H. E. & Stamler, J. S. Protein S-nitrosylation: purview and parameters. *Nature Rev. Mol. Cell Biol.* 6, 150-166 (2005).
22. Nathan, C. Specificity of a third kind: reactive oxygen and nitrogen intermediates in cell signaling. *J. Clin. Invest.* 111, 769-778 (2003).
23. Eu, J. P., Sun, J., Xu, L., Stamler, J. S. & Meissner, G. The skeletal muscle calcium release channel: coupled $O_2$ sensor and NO signaling functions. *Cell* 102, 499-509 (2000).
24. Packer, M. A. et al. Nitric oxide negatively regulates mammalian adult neurogenesis. *Proc. Natl. Acad Sci. USA* 100, 9566-9571 (2003).
25. Feng, Q. et al. Development of heart failure and congenital septal defects in mice lacking endothelial nitric oxide synthase. *Circulation* 106, 873-879 (2002).
26. Barouch, L. A. et al. Nitric oxide regulates the heart by spatial confinement of nitric oxide synthase isoforms. *Nature* 416, 337-340 (2002).
27. van Coelln, R., Dawson, V. L. & Dawson, T. M. Parkin-associated Parkinson's disease. *Cell Tissue Res.* 318, 175-184 (2004).
28. Yao, D. et al. Nitrosative stress linked to sporadic Parkinson's disease: S-nitrosylation of parkin regulates its E3 ubiquitin ligase activity. *Proc. Natl. Acad. Sci. USA* 101, 10810-10814 (2004).
29. Tanaka, K., Suzuki, T., Hattori, N. & Mizuno, Y. Ubiquitin, proteasome and parkin. *Biochim. Biophys. Acta* 1695, 226-238 (2004).
30. Wieland, T. & Mittman, C. Regulators of G-protein signalling: multifunctional proteins with impact on signalling in the cardiovascular system. *Pharmacol. Therapeut.* 97, 95-115 (2003).
31. Rogers, J. S. et al. RGS4 reduces contractile dysfunction and hypertrophic gene induction in Gaq-overexpressing mice. *J. Mol. Cell. Cardiol.* 33, 209-218 (2001).
32. Albig, A. R. & Schiemann, W. P. Identification and characterization of regulator of G protein signaling 4 (RGS4) as a novel inhibitor of tubulogenesis: RGS4 inhibits mitogen-activated protein kinases and vascular endothelial growth factor signaling. *Mol. Biol. Cell* 16, 609-625 (2005).
33. Balzi, E., Choder, M., Chen, W., Varshavsky, A. & Goffeau, A. Cloning and functional analysis of the arginyl-tRNA-protein transferase gene ATE1 of Saccharomyces cerevisiae. *J. Biol. Chem.* 265, 7464-7471 (1990).
34. Varshavsky, A. 'Spalog' and 'sequelog': neutral terms for spatial and sequence similarity. *Curr. Biol.* 14, R181-R183 (2004).
35. Berman, D. M. & Gilman, A. G. Mammalian RGS proteins: Barbarians at the gate. *J. Biol; Chem.* 273, 1269-1272 (1998).
36. Smotrys, J. E. & Linder, M. E. Palmitoylation of intracellular signaling proteins: regulation and function. *Annu. Rev. Biochem.* 73, 559-587 (2004).
37. Krumins, A. M. et al. Differentially regulated expression of endogenous RGS4 and RGS7. *J. Biol. Chem.* 279, 2593-2599 (2004).

38. Davydov, I. V. & Varshavsky, A. RGS4 is arginylated and degraded by the N-end rule pathway in vitro. *J. Biol. Chem.* 275, 22931-22941 (2000).
39. Mülsch, A., Lurie, D. J., Seimenis, I., Fichtlscherer, B. & Foster, M. A. Detection of nitrosyl-iron complexes by proton-electron-double-resonance imaging. DNIC as endogenous NO carrier. *Free Radic. Biol. Med.* 27, 636-646 (1999).
40. Becker, K., Savvides, S. N., M., K., Schirmer, R. H. & Karplus, P. A. Enzyme inactivation through sulfhydryl oxidation by physiologic NO-carriers. *Nature Struct. Biol.* 5, 267-271 (1998).
41. Kempf, T. & Wollert, K. C. Nitric oxide and the enigma of heart hyperthrophy. *BioEssays* 26, 608-615 (2004).
42. Bedford, M. T. & Richard, S. Arginine methylation: an emerging regulator of protein function. *Mol. Cell* 18, 263-272 (2005).
43. Vossenaar, E. R., Zendman, A. J. W., van Venrooij, W. J. & Pruijn, G. J. M. PAD, a growing family of citrullinating enzymes: genes, features and involvement in disease. *BioEssays* 25, 1106-1118 (2003).

Although the invention has been described with reference to the above examples, it will be understood that modifications and variations are encompassed within the spirit and scope of the invention. Accordingly, the invention is limited only by the following claims.

What is claimed is:

1. A method of identifying an agent that modulates arginine-tRNA protein transferase mediated N-end rule pathway mediated arginylation of an amino terminal (N-terminal) cysteine (Cys) residue of a peptide, comprising:
   a) contacting at least one sample comprising a peptide consisting of the amino sequence Cys-His-Ser-Gly-Ala-Trp-Leu (SEQ ID NO:1) or a fusion protein comprising said peptide fused to a reporter polypeptide, with at least one test agent, under conditions suitable for the N-terminal Cys of the peptide to act as a substrate for an N-end rule pathway reaction; and
   b) detecting a change in the N-end rule pathway substrate activity of the N-terminal Cys of the peptide in the presence of the test agent as compared to the absence of the test agent; and
   c) correlating the change in the N-end rule pathway substrate activity with a modulation of the N-end rule pathway substrate activity,
   thereby identifying the test agent as an agent that modulates N-end rule pathway mediated arginylation of an N-terminal Cys residue of said peptide.

2. The method of claim 1, wherein the peptide further comprises a regulator of G protein signaling (RGS) protein.

3. The method of claim 1, wherein the peptide is a synthetic peptide.

4. The method of claim 1, wherein the peptide is located at the N-terminal of said fusion protein.

5. The method of claim 4, wherein the reporter polypeptide is fused to the C-terminus of the peptide.

6. The method of claim 5, wherein the reporter polypeptide comprises a selectable marker protein or a detectable label.

7. The method of claim 6, wherein the selectable marker protein is an antibiotic resistance protein and the fusion protein is within a test cell from said sample.

8. The method of claim 6, wherein the detectable label is a fluorescent protein, a luminescence generating protein, or an enzyme.

9. The method of claim 8, wherein the fluorescent protein is Aequorea green fluorescent protein, the luminescence generating protein is luciferase, or the enzyme is β-galactosidase.

10. The method of claim 7, wherein the fusion protein is inducible.

11. The method of claim 1, wherein the peptide having the N-terminal Cys is located in an internal peptide portion of said fusion protein, and wherein said method further comprises contacting the fusion protein with a protease that cleaves the protein to generate the peptide having the N-terminal Cys-(basic amino acid residue) motif.

12. The method of claim 1, wherein the sample is a cell-free sample.

13. The method of claim 1, wherein the sample is a cell, or an extract of a cell.

14. The method of claim 13, wherein the cell is a cell of a plant or a cell of an animal.

15. The method of claim 13, wherein the cell expresses an R-transferase.

16. The method of claim 15, wherein the R-transferase is endogenous to the cell.

17. The method of claim 1, wherein detecting the change in the N-end rule pathway substrate activity of the N-terminal Cys of the peptide comprises:
   a) measuring S-nitrosylation levels of the N-terminal Cys;
   b) measuring oxidation of the N-terminal Cys; or
   c) measuring arginylation of the N-terminal Cys.

18. The method of claim 1, wherein detecting the change in the N-end rule pathway substrate activity of the N-terminal Cys of the peptide is performed using mass spectroscopy or capillary electrophoresis.

19. The method of claim 1, wherein the method is performed in a high throughput format.

20. The method of claim 19, wherein the step of contacting comprises contacting each of a plurality of samples with at least one test agent.

21. The method of claim 20, wherein the plurality of samples are different.

22. The method of claim 20, wherein the plurality of samples are the same and at least one of the test agents is different.

23. The method of claim 22, wherein the different test agents comprise agents of a library of test agents.

24. The method of claim 23, wherein the library of test agents comprises a combinatorial library of test agents.

25. The method of claim 23, wherein the combinatorial library comprises a random library, a biased library, or a variegated library of test agents.

26. The method of claim 14, wherein the plant is infected with a pathogen.

27. The method of claim 14, wherein the animal has a disorder associated with abnormal protein degradation.

28. A method of identifying an agent that modulates arginine-tRNA protein transferase mediated N-end rule pathway arginylation of an amino terminal (N-terminal) cysteine (Cys) residue of a polypeptide, comprising:
   a) contacting at least one test agent with at least a first cell that expresses a reporter protein comprising an N-terminal cysteine residue wherein the N-terminus of the protein comprises a peptide consisting of the sequence Cys-His-Ser-Gly-Ala-Trp-Leu (SEQ ID NO:1) fused to said reporter protein, wherein the half-life of the reporter protein is affected by arginylation of the N-terminal residue of the protein; and
   b) measuring the level of the reporter protein expressed in the presence as compared to the absence of the test agent, wherein a change in the level of reporter protein expressed is indicative of modulation of N-terminal arginylation activity, correlating the change in the level of reporter protein with modulation of N-terminal arginylation activity, thereby identifying an agent that modulates N-terminal arginylation activity by the N-end rule pathway.

29. The method of claim 28, wherein the cell is a cultured mammalian cell, a yeast cell, or a bacterial cell.

30. The method of claim 28, wherein the reporter protein is expressed as a cleavable fusion protein comprising a reporter protein and a ubiquitin domain functionally linked to the reporter protein.

31. The method of claim 28, wherein the reporter protein is a selectable marker protein, a fluorescent protein, a luminescence generating protein, or an enzyme.

32. The method of claim 28, wherein the expression of the reporter protein is inducible.

33. The method of claim 28, wherein the reporter protein has a half-life in the cell of less than about an hour in the absence of the test agent.

34. The method of claim 28, wherein the reporter protein has a half-life in the cell of less than about 10 minutes in the absence of the test agent.

35. The method of claim 28, further comprising:
c) contacting at least a second cell that expresses a second reporter protein, wherein the half-life of the second reporter protein is affected by N-terminal arginylation of the protein, with at least one potential modulator of arginine tRNA protein transferase-1 (ATE 1) gene product activity; and d) measuring the level of second reporter protein expressed within the second cell relative to the level of reporter protein expressed within the first cell.

36. The method of claim 35, wherein the first cell and the second cell are the same cell.

* * * * *

UNITED STATES PATENT AND TRADEMARK OFFICE
CERTIFICATE OF CORRECTION

PATENT NO. : 7,575,881 B2
APPLICATION NO. : 11/228157
DATED : August 18, 2009
INVENTOR(S) : Hu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 349 days.

Signed and Sealed this

Seventh Day of September, 2010

David J. Kappos
*Director of the United States Patent and Trademark Office*